(12) United States Patent
Greene et al.

(10) Patent No.: US 7,723,021 B2
(45) Date of Patent: May 25, 2010

(54) METHODS FOR TREATING LENTIVIRUS INFECTIONS

(75) Inventors: Warner C. Greene, Hillsborough, CA (US); Kimberly S. Stopak, San Francisco, CA (US); Carlos M. deNoronha, Hillsborough Court, CA (US); Ya-Lin Chiu, San Francisco, CA (US); Vanessa B. Soros, San Francisco, CA (US); Wesley M. Yonemoto, San Francisco, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 0 days.

(21) Appl. No.: 11/671,991

(22) Filed: Feb. 6, 2007

(65) Prior Publication Data

US 2007/0134653 A1 Jun. 14, 2007

Related U.S. Application Data

(62) Division of application No. 10/865,663, filed on Jun. 9, 2004.

(60) Provisional application No. 60/477,549, filed on Jun. 10, 2003, provisional application No. 60/505,738, filed on Sep. 24, 2003.

(51) Int. Cl.
*C12Q 1/00* (2006.01)
(52) U.S. Cl. .......................................................... 435/4
(58) Field of Classification Search ........................ None
See application file for complete search history.

(56) References Cited

U.S. PATENT DOCUMENTS

| 6,051,227 | A | 4/2000 | Allison et al. |
| 2003/0035790 | A1 | 2/2003 | Chen et al. |
| 2004/0009951 | A1 | 1/2004 | Malim et al. |
| 2004/0234956 | A1 | 11/2004 | Kabat et al. |
| 2005/0112555 | A1 | 5/2005 | Smith et al. |
| 2005/0112562 | A1 | 5/2005 | Payan et al. |

FOREIGN PATENT DOCUMENTS

| WO | WO 96/36350 A1 | 11/1996 |
| WO | WO 02/36141 A2 | 5/2002 |
| WO | WO 2004/013160 A2 | 2/2004 |
| WO | WO 2005/024422 A2 | 3/2005 |

OTHER PUBLICATIONS

Yu et al., Induction of APOBEC3G Ubiquitination and Degradation by anHIV-1 Vif-Cul5-SCF Complex, Science, 2003, 302(5647):1056-1060.*
Desrosiers, Ronald C. et al.; "Identification of Highly Attenuated Mutants of Simian Immunodeficiency Virus"; 1998, *Journal of Virology*, vol. 72, No. 2, pp. 1431-1437.
Fisher, Amanda G. et al.; "The *sor* Gene of HIV-1 Is Required for Efficient Virus Transmission in Vitro"; 1987, *Science*, vol. 237, pp. 888-893.
Gabuzda, Dana H. et al.; "Role of *vif* in Replication of Human Immunodeficiency Virus Type 1 in CD4$^+$ T Lymphocytes"; 1992, *Journal of Virology*, vol. 66, No. 11, pp. 6489-6495.
Harris, Reuben S. et al.; "DNA Deamination Mediates Innate Immunity to Retroviral Infection"; 2003, *Cell*, vol. 113, pp. 803-809.
Harris, Reuben S. et al.; "Correction: DNA Deamination Mediates Innate Immunity to Retroviral Infection"; 2004, *Cell*, vol. 116, pp. 629.
LeCossier, Denise et al.; "Hypermutation of HIV-1 DNA in the Absence of the Vif Protein"; 2003, *Science*, vol. 300, pp. 1112.
Mangeat, Bastain et al.; "Broad antiretroviral defence by human APOBEC3G through lethal editing of nascent reverse transcripts"; 2003, *Nature*, vol. 424, pp. 99-103.
Mariani R. et al.; "The Murine Homologue of the VIF Cellular Co-factor, APOBEC3G/CEM15, is a Potent Inhibitor of HIV-1 Replication Whose Activity is Not Blocked by HIV-1 or SIV VIF"; 2003, *10th Conference on Retroviruses and Opportunistic Infections*, abstract No. 72, 1 page.
Pomerantz, Roger J.; "HIV: A tough viral nut to crack"; 2002, *Nature*, vol. 418, pp. 594-595.
Sheehy, Ann M. et al.; "Isolation of a human gene that inhibits HIV-1 infection and is suppressed by the viral Vif protein"; 2002, *Nature*, vol. 418, pp. 646-649.
Sova, Pavel et al.; "Efficiency of Viral DNA Synthesis during Infection of Permissive and Nonpermissive Cells with vif-Negative Human Immunodeficiency Virus Type 1"; 1993, *Journal of Virology*, vol. 67, No. 10, pp. 6322-6326.
von Schwedler, Uta et al.; "*vif* is Crucial for Human Immunodeficiency Virus Type 1 Proviral DNA Synthesis in Infected Cells"; 1993, *Journal of Virology*, vol. 67, No. 8, pp. 4945-4955.
Zhang, Hui et al.; "The cytidine deaminase CEM15 Induces hypermutation in newly synthesized HIV-1 DNA"; *Nature*, vol. 424, pp. 94-98.
Kao, Sandra et al.; "The HIV-1 VIF Protein Blocks Packaging of APOBEC3G (CEM15), a Cellular Inhibitor of Virus Infectivity"; 2003, *Abstracts of papers presented at the 2003 meeting on Retroviruses* (May 20-25, 2003), p. 203, 1 page abstract.
Khan, Mohammad et al.; "Sequences in the 5'-Ultranslated Region of the Viral RNA are Required for Packaging of VIF into Virus Particles"; 2003, *Abstracts of papers presented at the 2003 meeting on Retroviruses* (May 20-25, 2003), 1 page abstract.
Mehle, Andrew et al.; "VIF Overcomes the Innate Antiviral Activity of APOBEC3G by Promoting Its Degradation in the Ubiquitin-Proteasome Pathway"; 2004, *The Journal of Biological Chemistry*, vol. 279, No. 9, pp. 7792-7798.
Rose, Kristine et al.; "Antiviral Potency of APOBEC3G and its Neutralization by the HIV-1 Encoded Viral Infectivity Factor, VIF"; 2003, *Abstracts of papers presented at the 2003 meeting on Retroviruses* ((May 20-25, 2003), 1 page abstract.

(Continued)

*Primary Examiner*—Robert B Mondesi
*Assistant Examiner*—Nicole Kinsey White
(74) *Attorney, Agent, or Firm*—Townsend and Townsend and Crew LLP; Siegfried J. W. Ruppert

(57) ABSTRACT

The present invention provides methods of identifying an agent that inhibits an activity of a lentiviral Vif protein. The present invention provides methods of identifying an agent that increases the level of active APOBEC3G in a cell. The present invention provides agents identified by a subject screening method; and further provides methods for treating lentivirus infections.

65 Claims, 22 Drawing Sheets

OTHER PUBLICATIONS

Sheehy, Ann M. et al.; "The antiretroviral enzyme APOBEC3G is degraded by the proteasome in response to HIV-1 VIF"; 2003, *Nature Medicine*, vol. 9, No. 11, pp. 1404-1407.

Stopak, Kim et al.; "HIV-1 VIF is Recruited to a High Molecular Weight Ribonucleoprotein Complex Containing APOBEC3G"; 2003, *Abstracts of papers presented at the 2003 meeting on Retroviruses* ((May 20-25, 2003), 1 page abstract.

Xu, Hongzhan et al.; "A single amino acid substitution in human APOBEC3G antiretroviral enzyme confers resistance to HIV-1 virion infectivity factor-induced depletion"; 2004, *PNAS*, vol. 101, No. 15, pp. 5652-5657.

Zhang, Hui et al.; "A Cytidine Deaminase, CEM15/APOBEC3G, Induces Hypermutation in Newly-Synthesized HIV-1 DNA"; 2003, *Abstracts of papers presented at the 2003 meeting on Retroviruses* ((May 20-25, 2003), 1 page abstract.

Gaddis, Nathan Clay; "Investigation of the Role of VIF in the HIV-1 Life Cycle"; Catalogued in University of Pennsylvania library on Feb. 24, 2003, 163 pages.

U.S. Appl. No. 60/419,982, filed Oct. 21, 2002.
U.S. Appl. No. 60/401,293, filed Aug. 5, 2002.
U.S. Appl. No. 11/671,951, filed Feb. 6, 2007.
U.S. Appl. No. 60/473,357, filed May 23, 2003.
U.S. Appl. No. 10/865,663, filed Jun. 9, 2004.
Judgement in re: Patent Interference No. 105,686 dated Sep. 2, 2009, 2 pages.

* cited by examiner

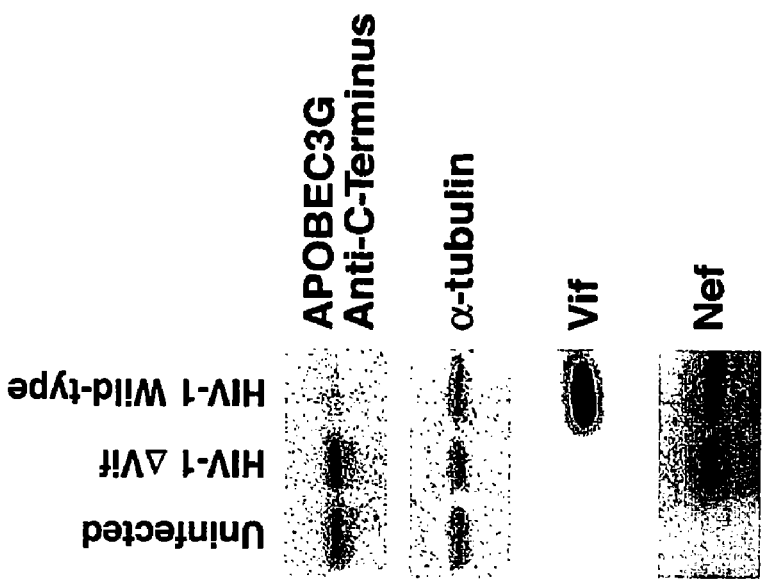
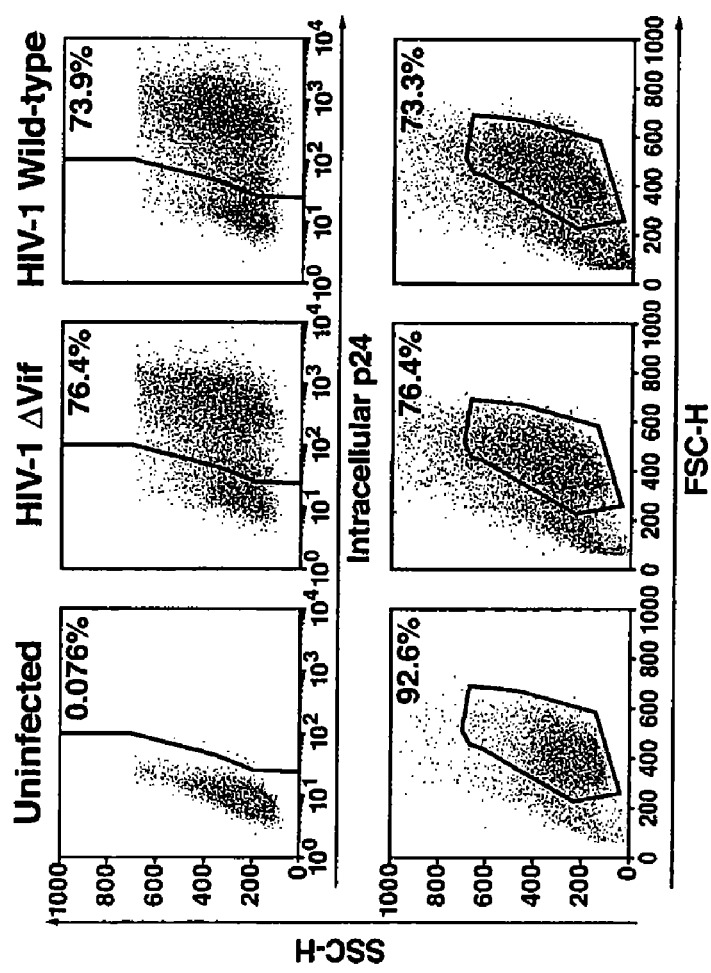

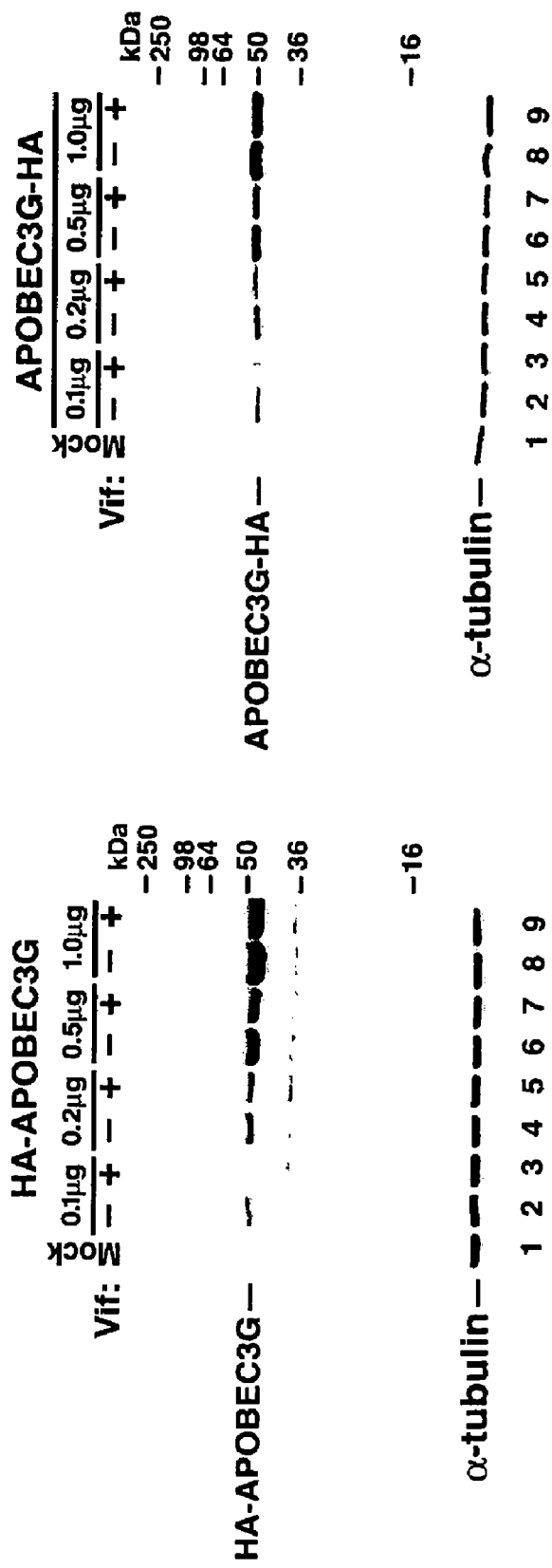

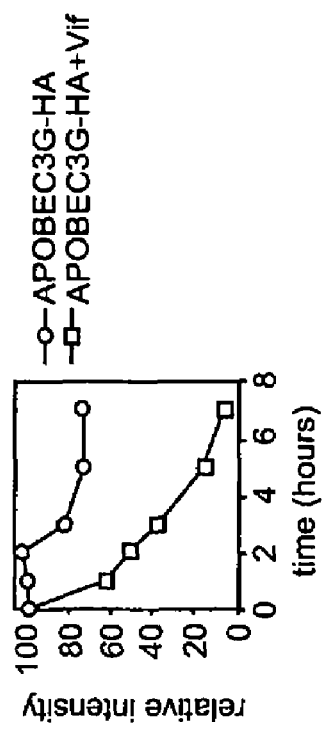
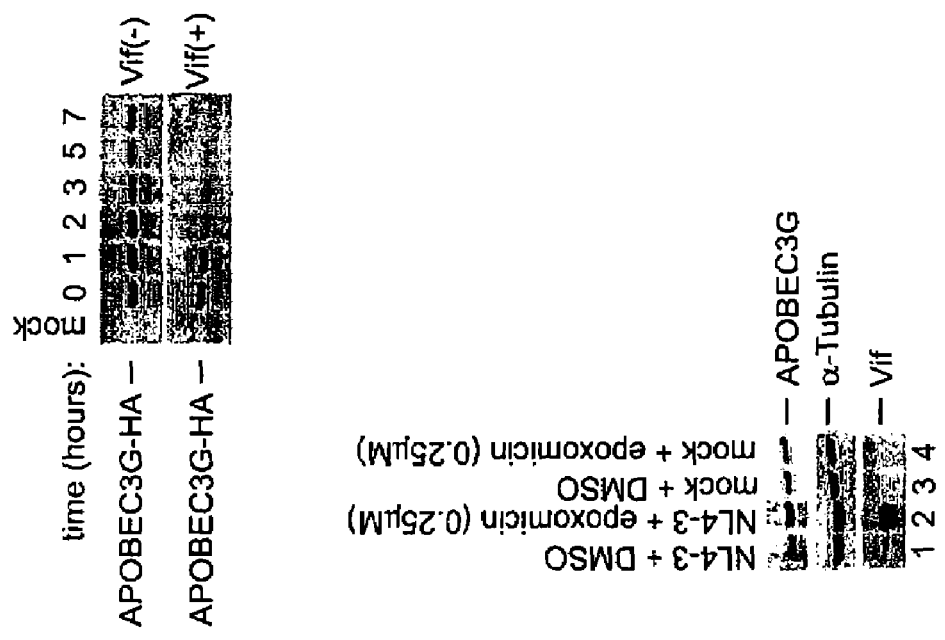
FIG. 8A
FIG. 8B

METHODS FOR TREATING LENTIVIRUS INFECTIONS

CROSS-REFERENCE

This application is a divisional application of application Ser. No. 10/865,663, filed Jun. 9, 2004, and claims the benefit of U.S. Provisional Patent Application No. 60/477,549 filed Jun. 10, 2003, and U.S. Provisional Patent Application No. 60/505,738, filed Sep. 24, 2003, which applications are incorporated herein by reference in their entirety.

STATEMENT REGARDING FEDERALLY SPONSORED RESEARCH

This invention was made with government support under grant nos. P01 HD40543, R01 CA86814, and 2P30 A127763-1 awarded by the National Institutes of Health. The government has certain rights in this invention.

FIELD OF THE INVENTION

This invention is in the field of treating lentivirus infections, particularly immunodeficiency virus infections.

BACKGROUND OF THE INVENTION

Human immunodeficiency virus (HIV) is the etiologic agent of acquired immunodeficiency syndrome (AIDS). HIV infection leads to depletion of $CD4^+$ T lymphocytes. AIDS is characterized by various pathological conditions, including immune incompetence, opportunistic infections, neurological dysfunctions, and neoplastic growth.

HIV-1 relies on Vif (virion infectivity factor), a protein encoded by HIV-1 and many related primate lentiviruses, to evade the potent innate antiviral function of APOBEC3G (apolipoprotein B mRNA-editing enzyme, catalytic polypeptide-like 3G, also known as CEM15). APOBEC3G is a DNA cytidine deaminase that is incorporated into virions and produces extensive hypermutation in newly synthesized viral DNA formed during reverse transcription.

Several drugs have been approved for treatment of AIDS, including azidovudine (AZT), didanosine (dideoxyinosine, ddI), d4T, zalcitabine (dideoxycytosine, ddC), nevirapine, lamivudine (epivir, 3TC), saquinavir (Invirase), ritonavir (Norvir), indinavir (Crixivan), and delavirdine (Rescriptor). However, none of the available drugs used to combat HIV is completely effective, and treatment frequently gives rise to drug-resistant virus.

Despite the availability of a number of drugs to combat HIV infections, there is a need in the art for additional drugs that inhibit HIV replication, and which are suitable for treating HIV and other lentiviral infections. The present invention addresses this need by providing methods for identifying agents that target the HIV Vif protein, as well as agents that interfere with Vif action in a manner that preserves the potent innate anti-lentiviral properties of APOBEC3G.

Literature

Fisher et al. (1987) *Science* 237, 888-893; von Schwedler et al. (1993) *J Virol* 67, 4945-4955; Desrosiers et al. (1998) *J Virol* 72, 1431-1437; Gabuzda et al. (1992) *J Virol* 66, 6489-6495; Sova and Volsky (1993) *J Virol* 67, 6322-6326; Harris et al. (2003) (2003) *Cell* 113:803-809; Harris et al. (2004) *Cell* 116:629; Lecossier et al. (2003) *Science* 300:1112; Mangeat et al. (2003) *Nature* 424:99-103; Zhang et al. (2003) *Nature* 424:94-98.

SUMMARY OF THE INVENTION

The present invention provides methods of identifying an agent that inhibits an activity of a lentiviral Vif protein. The present invention provides methods of identifying an agent that increases the level of active APOBEC3G in a cell. The present invention provides agents identified by a subject screening method; and further provides methods for treating lentivirus infections.

BRIEF DESCRIPTION OF THE DRAWINGS

FIGS. 3A and 3B depict intracellular depletion of APOBEC3G induced by HIV wild type but not HIVΔVif viruses following infection of human H9 cells.

FIGS. 7A-C depict HIV-1 Vif induction of APOBEC3G degradation.

FIGS. 8A-C depict the effect of Vif on the half-life of APOBEC3G; and the effect of proteasome inhibitors on depletion of intracellular APOBEC3G.

DEFINITIONS

Figure 1B:
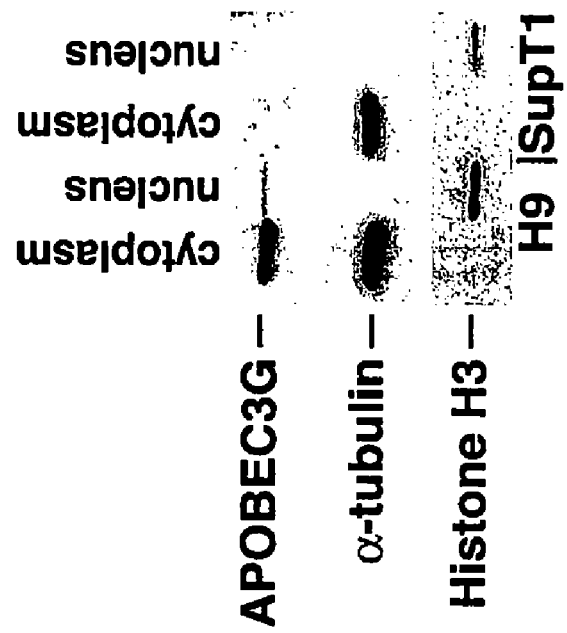
FIGS. 1A and 1B depict expression and localization of APOBEC3G.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In the context of lentivirus infection, the term "treatment" encompasses prevention of establishment of a systemic infection following initial contact with the virus; and prophylactic treatment of an individual not yet infected with the virus.

The terms "individual," "host," "subject," and "patient," used interchangeably herein, refer to a mammal, including, but not limited to, murines, felines, simians, humans, mammalian farm animals, mammalian sport animals, and mammalian pets. The term includes mammals that are susceptible to infection by a lentivirus that encodes Vif. In many embodiments, treatment of humans is of interest.

By "genetic transformation" is meant a permanent or transient genetic change induced in a cell following incorporation of new DNA (i.e., DNA exogenous to the cell). Genetic change can be accomplished either by incorporation of the new DNA into the genome of the host cell, or by transient or stable maintenance of the new DNA as an episomal element. Where the cell is a mammalian cell, a permanent genetic change is generally achieved by introduction of the DNA into the genome of the cell.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as $CD4^+$ T lymphocytes, glial cells, macrophages, tumor cells, peripheral blood mononuclear cells (PBMC), and the like. The term "biological sample" encompasses a clinical sample, and also includes cells in culture, cell supernatants, tissue samples, organs, bone marrow, and the like.

The term "lentivirus" as used herein, refers to human immunodeficiency virus-1 (HIV-1); human immunodeficiency virus-2 (HIV-2); simian immunodeficiency virus (SIV); and feline immunodeficiency virus (FIV).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a Vif protein" includes a plurality of such proteins and reference to "the agent" includes reference to one or more agents and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of identifying an agent that inhibits an activity of a lentiviral Vif protein. The invention further provides methods of identifying an agent that increases the level of active APOBEC3G in a cell; as well as methods of identifying an agent that converts an inactive form of APOBEC3G to an active form of APOBEC3G. The present invention provides agents identified by a subject screening methods; and further provides methods for treating lentivirus infections.

Human immunodeficiency virus type 1 (HIV-1) relies on Vif (virion infectivity factor), a protein encoded by HIV-1 and many related primate lentiviruses, to evade the potent innate antiviral function of APOBEC3G (apolipoprotein B mRNA-editing enzyme, catalytic polypeptide-like 3G, also known as CEM15). APOBEC3G is a DNA cytidine deaminase that is incorporated into virions and produces extensive hypermutation in newly synthesized viral DNA formed during reverse transcription.

The present invention is based in part on the following observations: 1) Vif impairs the incorporation of native APOBEC3G protein into virions by targeting it for degradation within infected cells (including, e.g., T cells, macrophages, glial cells, etc.) infected with a Vif-encoding lentivirus; 2) Vif alone is sufficient to induce the loss of APOBEC3G, indicating that Vif does not require the activity of other viral proteins; 3) Vif either directly or indirectly assembles with APOBEC3G; 4) APOBEC3G and Vif co-fractionate in a >700 kD complex in infected H9 cells, and this large APOBEC3G complex disassembles following treatment with RNAse; 5) APOBEC3G is polyubiquitylated; 6) Vif targets modified forms of APOBEC3G protein, such as polyubiquitylated APOBEC3G, for degradation; 7) Vif inhibits translation of APOBEC3G mRNA; 8) APOBEC3G is found in a high molecular weight (HMW) complex in cells permissive for HIV infection; 9) certain factors can increase the level of APOBEC3G protein in a cell; 10) Low molecular weight (LMW) APOBEC3G complexes exhibit cytidine deaminase activity, while HMW APOBEC3G complexes do not.

Screening Methods

The present invention provides methods of identifying an agent that inhibits a lentivirus Vif activity. The methods generally involve contacting a sample containing a Vif protein and an APOBEC3G protein with a test agent; and determining the effect, if any, of the test agent on a Vif activity. A test agent that affects Vif activity is a candidate agent for treating lentiviral infections.

The present invention further provides methods of identifying an agent that increases the level of active APOBEC3G protein in a cell. The methods generally involve contacting a cell with a test agent; and determining the effect, if any, of the test agent on the level of active APOBEC3G protein in the cell. A test agent of interest increases the level of active APOBEC3G in a cell, regardless of the mechanism by which the increase is achieved. For example, an agent that increases a level of active APOBEC3G in a cell includes i) an agent that increases production of active APOBEC3G by the cell, regardless of the mechanism; ii) an agent that reduces formation of an inactive form of APOBEC3G in a cell; iii) an agent that induces a shift from an inactive form of APOBEC3G to an active form of APOBEC3G in a cell; and the like.

The present invention provides methods of identifying an agent that converts an inactive form of APOBEC3G protein to an active form of an APOBEC3G protein in a cell. The methods generally involve contacting a cell with a test agent; and determining the effect, if any, of the test agent on converting an inactive form of APOBEC3G to an active form of APOBEC3G.

As used herein, the term "active APOBEC3G" refers to a form of APOBEC3G that is enzymatically active and induces one or more mutations in a lentivirus genome. An "active" form of APOBEC3G is a form that can induce mutations in a lentivirus genome. In general, active APOBEC3G is a low molecular weight form of APOBEC3G, e.g., a form that exists in a low molecular weight complex. In some embodiments, a low molecular weight form of APOBEC3G is a form of APOBEC3G that exists in a complex that has a molecular weight in a range of from about 50 kD to about 100 kD, as determined by size-exclusion fast performance liquid chromatography (FPLC). An agent of interest that increases the level of APOBEC3G is in many embodiments an agent that increases a level of APOBEC3G that induces mutations into a lentivirus genome, such that the active APOBEC3G induces a sufficient number of mutations such that viral replication is inhibited and/or production of infectious virus is reduced.

As used herein, the term "inactive APOBEC3G" refers to a form of APOBEC3G that is relatively inactive, e.g., is a form that does not induce mutations in a lentivirus genome in the cytoplasm of a cell that would result in disabling the lentivirus, e.g., a form that does not induce a number of mutations in a lentivirus genome that would be sufficient to adversely affect production of infectious virus; or that is not incorporated into a lentivirus virion. In some embodiments, an inactive form of APOBEC3G is a form that exists in a high molecular weight complex. In some embodiments, a high molecular weight form of APOBEC3G is a form of APOBEC3G that exists in a complex that has a molecular weight in a range of greater than about 700 kD, as determined by size-exclusion FPLC.

As used herein, the term "Vif activity" includes, but is not limited to, Vif binding to APOBEC3G; Vif-mediated reduction of intravirion incorporation of endogenous APOBEC3G protein; Vif association with a high-molecular weight complex comprising APOBEC3G and cellular RNA; Vif inhibition of translation of APOBEC3G mRNA; and Vif induction of APOBEC3G degradation.

A subject assay for identifying agents that inhibit Vif activity can be designed in a number of ways. In some embodiments, the assay provides for determining the effect of a test agent on the level of APOBEC3G protein in a cell in the presence of Vif. In other embodiments, the assay provides for determining the effect of a test agent on Vif association with APOBEC3G or an APOBEC3G high molecular weight complex. These embodiments are described in detail below.

A subject assay for identifying agents that increase the level of active APOBEC3G protein in a cell can be designed in a number of ways. In some embodiments, a subject assay for identifying an agent that increases the level of active APOBEC3G involves determining the effect of a test agent on the level of APOBEC3G protein that induces a C→U mutation in minus strand DNA, resulting in a G→A mutation in viral plus strand DNA. In other embodiments, a subject assay for identifying an agent that increases the level of active APOBEC3G involves determining the effect of the agent on packaging of APOBEC3G into a lentivirus particle.

Methods of identifying an agent that converts an inactive form of APOBEC3G protein to an active form of an APOBEC3G protein in a cell can be designed in a number of ways. For example, in some embodiments, a method of identifying an agent that converts an inactive form of APOBEC3G to an active form of APOBEC3G involves contacting a cell with a test agent; and determining the molecular weight of a complex with which APOBEC3G is associated in the cell. Generally, an agent of interest is a test agent that converts a high molecular weight APOBEC3G-containing complex to a low molecular weight APOBEC3G-containing complex. In other embodiments, a method of identifying an agent that converts an inactive form of APOBEC3G to an active form of APOBEC3G involves contacting a cell with a test agent; and determining the effect, if any, of the test agent on the number of APOBEC3G-induced mutations in a lentivirus genome present in the cell.

The subject screening methods are carried out in vitro. In some embodiments, the methods are cell-based methods. In other embodiments, the methods are cell-free methods.

The terms "candidate agent," "agent," "substance," "test agent," and "compound" are used interchangeably herein. Candidate agents encompass numerous chemical classes, and are generally synthetic, semi-synthetic, or naturally-occurring inorganic or organic molecules.

In some embodiments, a candidate agent is a small organic compound having a molecular weight of more than 50 daltons and less than about 2,500 daltons.

Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

In other embodiments, a candidate agent has a molecular weight of greater than 2,500 daltons. In these embodiments, a candidate agent may be a peptide, an oligopeptide, a polypeptide, a carbohydrate, a polysaccharide, a lipid, a lipopolysaccharide, a glycoprotein, a proteoglycan, a lipoprotein, or other macromolecule.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

A candidate agent is assessed for any cytotoxic activity it may exhibit toward the cell used in the assay, using well-known assays, such as trypan blue dye exclusion, an MTT ([3-(4,5-dimethylthiazol-2-yl)-2,5-diphenyl-2H-tetrazolium bromide]) assay, and the like. Agents that do not exhibit significant cytotoxic activity are considered candidate agents.

Assays of the invention usually include one or more controls. Thus, a test sample includes a test agent, and a control sample has all the components of the test sample except for the test agent. Generally a plurality of assay mixtures is run in parallel with different agent concentrations to obtain a differential response to the various concentrations. Typically, one of these concentrations serves as a negative control, i.e. at zero concentration or below the level of detection. Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as nuclease inhibitors, anti-microbial agents, etc. may be used. The components may be added in any order. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

The screening methods may be designed a number of different ways, where a variety of assay configurations and protocols may be employed, as are known in the art. For example, one of the components may be bound to a solid support, and the remaining components contacted with the support bound component. As another example, a protein whose activity is being assayed is in some embodiments an endogenous protein (e.g., a protein that is normally produced by the cell); and in other embodiments, a protein whose activity is being assayed is encoded on an expression construct and introduced into the cell, such the encoded protein is produced in the cell. The above components of the method may be combined at substantially the same time or at different times.

Where the assay is a binding assay, following the contact and incubation steps, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the presence of bound complexes will then be detected.

In many embodiments, for safety reasons, where a subject assay method involves testing for viral infectivity, encapsidation of APOBEC3G in a viral particle, etc., instead of using an infectious lentivirus, a subject assay will employ a construct that includes nucleotide sequences encoding viral structural proteins (e.g., Gag) and other proteins necessary for encapsidation of a viral particle; however, the viral particles so produced will not be pathogenic for laboratory personnel. Thus, in the present application, the term "lentivirus-infected cell" and similar terms are understood to include cells infected with pathogenic virus, as well as (e.g., for testing purposes) cells transfected with viral constructs that do not lead to production of viral particles that are pathogenic for humans.

Furthermore, it should be understood that a subject method that involves determining the effect of a test agent on the number of APOBEC3G-induced mutations in a lentivirus genome need not be carried out using the entire lentivirus genome. Instead, a portion of a lentivirus genome can be used to determine the effect of a test agent on the number of APOBEC3G-induced mutations in a lentivirus genome. Thus, the term "lentivirus nucleic acid," as used herein, thus includes all or a portion of a lentivirus genome, where the nucleic acid may be single stranded or double stranded. The term "lentivirus nucleic acid" includes nucleic acids that comprise, in addition to a lentivirus nucleotide sequence, a heterologous nucleotide sequence (e.g., non-lentivirus nucleotide sequences, such as nucleotide sequences encoding detectable markers; non-lentivirus control elements; and the like). The term "lentivirus nucleic acid" includes nucleic acids that comprise naturally-occurring lentivirus nucleotide sequences; variants of lentivirus nucleotide sequences; and synthetic lentivirus nucleotide sequences. The term "lentivirus nucleic acid" includes a nucleic acid that comprises lentivirus minus strand DNA. In many embodiments, for assays involving determining the number of mutations in a lentivirus genome, and in particular determining the number of APOBEC3G-induced mutation in a lentivirus genome, a lentivirus nucleic acid that includes lentivirus minus strand DNA is used.

In some embodiments, a test agent of interest is one that reduces a Vif activity by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to the level of the Vif activity in a control in the absence of the test agent.

In other embodiments, a test agent of interest is one that increases the level of active APOBEC3G in a cell by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, at least about 2-fold, at least about 5-fold, at least about 10-fold, or at least about 25-fold, or more, when compared to the level of active APOBEC3G in a cell in the absence of the test agent.

In other embodiments, a test agent of interest is one that increases the number of mutations (e.g., APOBEC3G-induced mutations) in a lentivirus nucleic acid by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, at least about 2-fold, at least about 5-fold, at least about 10-fold, or at least about 25-fold, or more, when compared to the number of mutations in the lentivirus nucleic acid in the absence of the test agent.

In other embodiments, a test agent of interest is one that converts at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, or at least about 90%, or more, of an enzymatically inactive form of APOBEC3G to an enzymatically active form of APOBEC3G in a eukaryotic cell, when compared to the level of inactive APOBEC3G in the cell in the absence of the test agent.

Level of APOBEC3G

In some embodiments, a subject screening method involves determining the effect of a test agent on the level of APOBEC3G protein in a cell in the presence of Vif protein. Thus, in some embodiments, the method involves contacting a cell that produces Vif and APOBEC3G with a test agent; and determining the effect, if any, of the test agent on the level of APOBEC3G protein in the cell.

In these embodiments, a test agent of interest increases the level of APOBEC3G in the presence of Vif protein by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, at least about 2-fold, at least about 4-fold, at least about 5-fold, at least about 10-fold, at least about 15-fold, at least about 20-fold, or more, compared the level of APOBEC3G in the presence of Vif protein and in the absence of the test agent.

The APOBEC3G protein that is produced by the cell may have the amino acid sequence that is provided under GenBank Accession No. NP_068594, or fragments or variants thereof. For example, the APOBEC3G protein can have truncations of one to 50 amino acids from the amino terminus and/or the carboxyl terminus of the sequence provided under NP_068594. The APOBEC3G protein that is used can vary from the sequence provided under NP-068594 by from one to about 20 amino acids, e.g., the sequence can include from one to about 20 amino acid substitutions. Typically, the APOBEC3G protein that is used retains cytidine deaminase activity of the native, naturally-occurring protein. Suitable APOBEC3G proteins also include fusion proteins that include APOBEC3G and a heterologous protein (a "fusion partner") fused in-frame to the amino terminus or carboxyl terminus of the APOBEC3G protein. Suitable fusion partners include peptides and polypeptides that provide ease of purification, e.g., $(His)_n$, e.g., 6His, and the like; provide an epitope tag, e.g., glutathione-S-transferase (GST), hemagglutinin (HA; e.g., CYPYDVPDYA; SEQ ID NO:1), FLAG (e.g., DYKDDDDK; SEQ ID NO:2), c-myc (e.g., CEQKLI-SEEDL; SEQ ID NO:3), and the like; peptides and polypeptides provide a detectable signal, e.g., an enzyme that generates a detectable product (e.g., β-galactosidase, luciferase, horse radish peroxidase, alkaline phosphatase, etc.), or a protein that is itself detectable, e.g., a fluorescent protein (e.g., a green fluorescent protein), etc.; and the like. In some embodiments, an APOBEC3G protein comprises the amino acid sequence set forth in SEQ ID NO:4.

The Vif protein that is produced by the cell can have the amino acid sequence of any known lentivirus Vif protein. For example, the amino acid sequences of HIV-1 Vif proteins are provided under GenBank Accession Nos. AAP33677; AAN74526; AAN74517; AAP29646; AAD10945; AAD10937; AAD10929; etc.

In many embodiments, the effect of a test agent on APOBEC3G protein levels in the presence of Vif is determined by introducing expression vectors, which include (typically on separate vectors) Vif and APOBEC3G coding sequences, into suitable eukaryotic cells in in vitro culture, generating genetically modified cells that produce Vif and APOBEC3G proteins; contacting the genetically modified cells with a test agent; and determining the effect, if any, of the test agent on the level of APOBEC3G protein produced by the genetically modified cell.

Expression vectors that are suitable for expression in eukaryotic cells are constructed to include a coding region for a Vif protein (for production of Vif protein in the cell) or a coding region for APOBEC3G (for production of APOBEC3G in the cell). An expression vector comprising a Vif or an APOBEC3G coding region will generally include regulatory sequences ("control sequences" or "control regions") which are necessary to effect the expression of a Vif- or an APOBEC3G-coding polynucleotide to which they are operably linked. Expression vectors typically comprise a transcription initiation region, a promoter region, a Vif- or an APOBEC3G-coding nucleotide sequence, and a transcriptional termination region. Suitable promoters include constitutive promoters and inducible promoters, a number of which are well known in the art. Expression vectors generally have convenient restriction sites located near the promoter sequence to provide for the insertion of nucleic acid sequences encoding Vif or APOBEC3G proteins. A selectable marker operative in the expression host may be present.

Expression vectors are introduced into eukaryotic cells using any convenient means, including calcium phosphate precipitation; electroporation; infection (where the expression vectors are packaged into viral particles); liposome-mediated transfection; and the like. Suitable cells are eukaryotic cells, typically mammalian cells, including primary cells, immortalized cell lines, etc., including, but not limited to, COS cells, 293T cells, Jurkat cells, H9 cells, and the like.

Whether a test agent inhibits Vif-induced reduction of APOBEC3G protein levels can be determined by any known method for determining the level of a particular protein in a cell. In some embodiments, the assay is an immunological assay, using a APOBEC3G-specific antibody. Such methods include, but are not limited to, immunoprecipitating APOBEC3G from a cellular extract, and analyzing the immunoprecipitated APOBEC3G by sodium dodecyl sulfate polyacrylamide gel electrophoresis (SDS-PAGE); detecting a detectable fusion partner in a cell that produces a fusion protein that includes APOBEC3G and a fusion partner that provides a detectable signal; standard SDS-PAGE and immunoblotting (e.g., transfer of proteins from a gel generated during SDS-PAGE to a membrane, and probing the membrane with detectably labeled antibodies) of APOBEC3G from cells producing APOBEC3G.

In other embodiments, the assay is an assay that detects a fusion partner of a APOBEC3G fusion protein. Thus, e.g., where the APOBEC3G is part of a fusion protein that includes APOBEC3G, and, as a fusion partner, a protein that provides a detectable signal, the assay detects the fusion partner. Fusion partners include, but are not limited to, a green fluorescent protein (GFP); a fluorescent protein from an Anthozoa species (see, e.g., Matz et al. (1999) *Nat. Biotechnol.* 17:969-973); luciferase; β-galactosidase; and the like. A construct that includes a nucleotide sequence that encodes the APOBEC3G fusion protein is introduced into a eukaryotic cell. The level of APOBEC3G protein that is produced in the cell is determined by detecting the fusion partner. Immunological assays (protein blots, ELISAs, etc.) are used where the fusion partner is an immunological tag. Enzymatic assays are used where the fusion partner is an enzyme (e.g., β-galactosidase, luciferase, horse radish peroxidase, etc.) that produces a detectable product. Fluorimetric assays are used to detect fusion partners that are fluorogenic. A luminometer is used to detect fusion partners that yield a luminescent product. The fusion partner is detected by any known method appropriate to the fusion partner. The fusion partner is detected in a cell extract, using an assay appropriate to the fusion partner (e.g., an enzymatic assay, an immunological assay, etc.); or the fusion partner is detected in an intact cell, e.g., using flow cytometry. For example, where the fusion partner provides a fluorescent signal, the level of APOBEC3G is in some embodiments determined using a flow cytometer.

The following is one non-limiting example of a suitable assay for identifying agents that reduce Vif-induced degradation of APOBEC3G. Mammalian cells (e.g., an immortalized cell line) are stably transfected with an expression vector that includes a coding sequence for a luciferase-APOBEC3G fusion protein, such that the cells synthesize the luciferase-APOBEC3G (luc-APOBEC3G) fusion protein. A substrate for luciferase is provided in the cell medium, such that the substrate enters the cell, and is acted on by the luciferase portion of the luciferase-APOBEC3G to yield a luminescent product. The level of luciferase in the cell is detected using a luminometer, and the level of luc-APOBEC3G is expressed as relative light units. The cells are transfected with an expression vector that includes a coding sequence for Vif to yield a Vif/luc-APOBEC3G cell. Because Vif induces degradation of luc-APOBEC3G, the presence of Vif protein in the Vif/luc-APOBEC3G cell reduces the level of luc-APOBEC3G, compared to the level of luc-APOBEC3G in the absence of Vif. When the Vif/luc-APOBEC3G cell is contacted with a test agent that reduces Vif-induced APOBEC3G degradation, the level of luc-APOBEC3G increases relative to the level of luc-APOBEC3G in the Vif/luc-APOBEC3G cell in the absence of the test agent.

Thus, in some embodiments, a method of identifying an agent that reduces Vif-induced APOBEC3G degradation involves contacting a cell, which cell produces Vif and an APOBEC3G protein fused to a protein that provides a detectable signal, with a test agent (and, if necessary, a substrate for the protein that provides a detectable signal); and determining the effect, if any, of the test agent on the level of APOBEC3G in the cell. In some embodiments, a method of identifying an agent that reduces Vif-induced APOBEC3G degradation involves contacting a cell that produces Vif and an APOBEC3G-luciferase protein with a test agent and a substrate for luciferase; and determining the effect, if any, of the test agent on the level of APOBEC3G-luciferase in the cell, compared to the level of APOBEC3G-luciferase in the cell in the absence of the test agent. An agent that increases the level of APOBEC3G-luciferase protein in the cell by at least about 5%, at least about 10%, at least about 20%, at least about 30%, at least about 50%, at least about 75%, at least about 100%, at least about 2.5-fold, at least about 3-fold, at least about 4-fold, at least about 5-fold, at least about 10-fold, at least about 20-fold, or at least about 50-fold, or more, is an agent that inhibits Vif-induced APOBEC3G degradation.

Methods of Identifying Agents that Increase a Level of Active APOBEC3G in a Cell In some embodiments, the invention provides methods of identifying an agent that increases a level of active APOBEC3G in a cell. In these embodiments, a subject screening method involves determining the effect of a test agent on the level of active APOBEC3G protein in a cell. The method generally involves contacting a cell that produces APOBEC3G with a test agent; and determining the effect, if any, of the test agent on the level of active APOBEC3G protein in the cell.

In these embodiments, a test agent of interest is one that increases the level of active APOBEC3G in a cell by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, at least about 2-fold, at least about 5-fold, at least about 10-fold, or at least about 25-fold, or more, when compared to the level of active APOBEC3G in a cell in the absence of the test agent.

In some embodiments, a test agent of interest is one that increases production (e.g., synthesis) of active APOBEC3G in a cell by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, at least about 2-fold, at least about 5-fold, at least about 10-fold, or at least about 25-fold, or more, when compared to the level of production of active APOBEC3G in the cell in the absence of the test agent.

In other embodiments, a test agent of interest is one that increases the number of mutations (e.g., APOBEC3G-induced mutations) in a lentivirus nucleic acid by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, at least about 2-fold, at least about 5-fold, at least about 10-fold, or at least about 25-fold, or more, when compared to the number of mutations in the lentivirus nucleic acid in the absence of the test agent.

In some embodiments, a test agent of interest is one that increases the number of C→U mutations in a minus strand of a lentivirus by at least about 5%, at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, at least about 2-fold, at least about 5-fold, at least about 10-fold, or at least about 25-fold, or more, when compared to the number of C→U mutations in a minus strand of a lentivirus in the absence of the test agent.

In some embodiments, a test agent of interest is one that increases the proportion of lentivirus particles produced by a cell that have encapsidated APOBEC3G by at least about 5%, at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, at least about 2-fold, at least about 5-fold, at least about 10-fold, or at least about 25-fold, or more, when compared to the proportion of lentivirus particles produced by a cell that have encapsidated APOBEC3G in the absence of the test agent.

In some embodiments, a test agent of interest is one that decreases the infectivity of lentiviruses produced by a cell by at least about 5%, at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, or at least about 90%, or more, when compared to the infectivity of the viruses produced by the cell in the absence of the test agent.

In other embodiments, a test agent of interest is one that promotes disassembly of an inactive high molecular weight APOBEC3G complex, to yield an active low molecular weight APOBEC3G complex. In these embodiments, a test agent of interest is one that promotes disassembly of at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, or at least about 90%, or more, of an inactive high molecular weight APOBEC3G complex to an enzymatically active low molecular weight APOBEC3G complex in a eukaryotic cell, when compared to the level of inactive high molecular weight APOBEC3G complex in the cell in the absence of the test agent.

In some embodiments, a test agent of interest is one that converts at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, or at least about 90%, or more, of an enzymatically inactive form of APOBEC3G to an enzymatically active form of APOBEC3G in a eukaryotic cell, when compared to the level of inactive APOBEC3G in the cell in the absence of the test agent.

In some embodiments, the cell is one that produces endogenous APOBEC3G. In other embodiments, the effect of a test agent on the level of active APOBEC3G protein in a cell is determined by introducing an expression vector, which includes an APOBEC3G coding sequence, into suitable eukaryotic cells in in vitro culture, generating genetically modified cells that produce APOBEC3G protein; contacting the genetically modified cells with a test agent; and determining the effect, if any, of the test agent on the level of active APOBEC3G protein produced by the genetically modified cell.

The level of active APOBEC3G in a cell can be determined in various ways. In some embodiments, a subject assay for identifying an agent that increases production of active APOBEC3G in a cell involves determining the effect of the agent on the level of APOBEC3G production. In some embodiments, a subject assay for identifying an agent that increases the level of active APOBEC3G involves determining the effect of a test agent on the level of APOBEC3G protein that induces a C→U mutation in a minus strand, resulting in a G→A mutation in viral reverse transcripts and/ or that induces a C→T mutation in a DNA copy. In other embodiments, a subject assay for identifying an agent that increases the level of active APOBEC3G involves determining the effect of the agent on packaging of APOBEC3G into a lentivirus particle. In other embodiments, a subject assay for identifying an agent that increases the level of active APOBEC3G involves determining the effect of the agent viral infectivity. In other embodiments, a subject assay involves determining the effect of a test agent on converting an inactive high molecular weight APOBEC3G complex to an active low molecular weight APOBEC3G complex.

Where a subject assay for identifying an agent that increases the level of active APOBEC3G in a cell involves determining the effect of a test agent on the level of synthesis of APOBEC3G by the cell, the assay can be conducted in a number of ways. For example, synthesis of APOBEC3G by the cell can be detected using a cell that produces APOBEC3G; contacting the cell with a test agent; and detecting the level of APOBEC3G protein using an immunoblot assay with antibody specific for APOBEC3G, or an ELISA assay with antibody specific for APOBEC3G. The cells are typically lysed to release the APOBEC3G. As another example, synthesis of APOBEC3G by the cell can be detected using a cell that includes an expression construct that comprises a nucleotide sequence that encodes APOBEC3G under control of an APOBEC3G promoter; contacting the cell with the test agent; and detecting the level of APOBEC3G protein using an immunoblot assay with antibody specific for APOBEC3G, or an ELISA assay with antibody specific for APOBEC3G. As another non-limiting example, synthesis of APOBEC3G by the cell can be detected using a cell that includes an expression construct that comprises a nucleotide sequence that encodes a fusion protein comprising all or a portion of APOBEC3G and a detectable heterologous protein that provides for a detectable signal (e.g., luciferase, β-galactosidase, a green fluorescent protein, an epitope tag such as hemagglutinin, and the like), under the control of an APOBEC3G promoter; contacting the cell with the test agent; and detecting the level of APOBEC3G protein by detecting the heterologous protein, using standard assays well known in the art.

In some embodiments, the level of APOBEC3G in the cytoplasm is detected. In some embodiments, it is advantageous to increase the level of active APOBEC3G in the cytoplasm of a cell that is not yet infected with a lentivirus. Should such a cell become infected with a lentivirus, the increased level of active APOBEC3G in the cytoplasm of the cell will result in an increased number of APOBEC3G-induced mutations in the lentivirus genome, and thereby reduce the level of infectious virus produced by the cell. In these embodiments, a test agent of interest increases the level of active APOBEC3G in the cytoplasm of an uninfected cell (e.g., a cell not infected by a lentivirus) by at least about 5%, at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, at least about 2-fold, at least about 5-fold, at least about 10-fold, or at least about 25-fold, or more, when compared to the level of active APOBEC3G in the cytoplasm of the uninfected cell in the absence of the test agent. Whether a test agent increases the level of active APOBEC3G in the cytoplasm can be determined using any known assay (e.g., a cytidine deaminase assay). Whether a test agent increases the level of active APOBEC3G in the cytoplasm is readily determined by, e.g., immunoblotting nuclear and cytoplasmic fraction with APOBEC3G-specific antibody, as described in the Examples.

Where a subject assay for identifying an agent that increases the level of active APOBEC3G involves determining the effect of a test agent on the level of APOBEC3G protein that induces a C→U mutation in a lentivirus minus strand, resulting in a G→A mutation in viral reverse transcripts and/or that induces a C→T mutation in a DNA copy, the assay can be conducted in a number of ways. For example, the number of C→U mutations induced in a lentivirus minus strand is determined by detecting polymerase chain reaction (PCR) products amplified using Taq polymerase or Pfu polymerase, using as a template a cDNA copy of a lentivirus RNA produced by a cell in the presence or absence of a test agent. Taq polymerase will copy templates containing uracil; Pfu polymerase does not readily copy templates containing uracil. PCR performed with Taq polymerase will yield a product of the expected size (based on the location of the primers used); while PCR performed with Pfu polymerase will be produced at a much lower level than the Taq-produced product. As another example, PCR products amplified using Taq polymerase and, as template, a cDNA copy of a lentivirus RNA produced by a cell in the presence or absence of a test agent, are sequenced, and the presence of G→A substitutions is detected. Thus, e.g., in some embodiments, the level of active APOBEC3G in a cell is determined by detecting the number of G→A substitutions in a cDNA copy of a lentivirus RNA produced by a cell in the presence or absence of a test agent. Where a test agent increases the level of active APOBEC3G in a cell, the number of G→A substitutions in a cDNA copy of a lentivirus RNA produced by the cell in the presence of the test agent would be expected to be higher than the number of G→A substitutions in a cDNA copy of a lentivirus RNA produced by the cell in the absence of the test agent.

In some embodiments, the number of APOBEC3G-induced mutations in a lentivirus nucleic acid is determined using an in vitro cytidine deaminase assay. For example, a radiolabeled oligonucleotide substrate for deamination is incubated with test samples lacking or containing APOBEC3G. A suitable substrate contains a target deoxycytidine(s) for APOBEC3G action. APOBEC3G deaminates a cytosine base, converting it to uracil. Uracil is susceptible to the activity of uracil DNA glycosylase (UDG or UNG). Addition of UDG/UNG to the enzymatic reaction results in the removal of the uracil base from the oligonucleotide, creating an abasic lesion at the site of cytidine deamination. The phosphate-sugar backbone of the oligonucleotide at the abasic site is, in turn, susceptible to alkaline hydrolysis. Addition of NaOH to the reaction thus results in cleavage at the site of deamination. Cleavage is monitored by electrophoresis through acrylamide-urea gels, and APOBEC3G activity is thereby scored by the appearance of a shorter cleavage product derived from the longer substrate oligonucleotide, with cleavage occurring specifically at the site of deamination.

Where a subject assay for identifying an agent that increases the level of active APOBEC3G involves determining the level of virus encapsidation of APOBEC3G protein, the assay can be conducted in a number of ways. For example, a test cell (e.g., cells that are susceptible to infection by a lentivirus, e.g., HIV; e.g., cells that express $CD4^+$, CCR5 and CXCR4 on the cell surface) that produces lentivirus particles is contacted with a test agent; and the amount of APOBEC3G in viral particles is determined by analyzing viral particles in the cell supernatants for the presence of APOBEC3G. For example, viral particles present in the cell supernatant are harvested 24-48 hours after transfection with a viral construct; cellular debris is removed (e.g., by centrifugation); and the viral particles are concentrated. APOBEC3G is detected in viral particles using an immunological assay. For example, APOBEC3G is detected in an immunoblot assay in which viral particles are lysed, the proteins separated on a gel, then transferred to a solid support such as a nylon membrane or other type of membrane, and APOBEC3G is detected on the membrane using an antibody specific for APOBEC3G.

Where a subject assay for identifying an agent that increases the level of active APOBEC3G in a cell involves determining the level of lentivirus infectivity, the assay can be conducted in a number of ways. For example, viral infectivity can be determined using a single-round titration assay on $CD4^+$ cells, and measuring the viral titer in the presence and in the absence of the test agent. A suitable assay may involve contacting a permissive test cell (e.g., cells that are susceptible to infection by a lentivirus, e.g., HIV; e.g., cells that express $CD4^+$, CCR5 and CXCR4 on the cell surface) with supernatant from a lentivirus-producing cell (e.g., a cell transfected with a lentivirus construct), wherein the test cells include a coding sequence for a detectable marker (e.g., luciferase, β-galactosidase, a fluorescent protein (e.g., a green fluorescent protein) and the like) operably linked and under transcriptional control of an HIV long terminal repeat (LTR), such that infection of the cell by an infectious HIV virus particle results in activation of the HIV LTR and production of the detectable marker. Cell supernatants containing viral particles are used to infect the test cells; and infection of the test cells is detected by assaying for the detectable marker. Cell supernatants from lentivirus-producing cells contacted with a test agent are compared with cell supernatants from the same cells not contacted with the test agent. The number of infected test cells is an indication of the infectivity of the viral particles in the cell supernatant. Where the detectable marker is a green fluorescent protein, infectivity can be scored using a fluorescence activated cell sorter. Where the detectable marker is β-galactosidase, infectivity can be scored by 5-bromo-4-chloro-3-indoyl-β-D-galactoside staining. See, e.g., Mangeat et al. ((2003) Nature 424: 99-103. The infectivity of HIV viral particles in the supernatant of HIV infected cells having a high level of active APOBEC3g would be expected to be lower than the infectivity of HIV viral particles in the supernatant of HIV infected cells having a low level of active APOBEC3G.

Where a subject method involves determining the effect of a test agent on converting an inactive high molecular weight APOBEC3G complex to an active low molecular weight APOBEC3G complex, the levels of high molecular weight APOBEC3G complex and low molecular weight APOBEC3G complex in a cell can be determined by, e.g., lysing a cell that has been contacted with a test agent; and performing size exclusion FPLC on the lysate.

Methods of Identifying Agents that Inhibit Vif Binding to APOBEC3G

In some embodiments, the invention provides methods of identifying an agent that inhibits the interaction of a Vif polypeptide with APOBEC3G or an APOBEC3G complex. The methods generally involve contacting a Vif polypeptide and an APOBEC3G polypeptide or an APOBEC3G complex with a test agent, and determining the effect, if any, of the test agent on the interaction of Vif with APOBEC3G polypeptide or APOBEC3G complex. In some embodiments, methods of identifying an agent that inhibits the interaction of Vif polypeptide with an APOBEC3G polypeptide or an APOBEC3G complex are cell-based methods. In other embodiments, methods of identifying an agent that inhibits the interaction of a Vif polypeptide with an APOBEC3G polypeptide or an APOBEC3G complex are cell-free methods.

Formation of a binding complex between Vif and an APOBEC3G polypeptide or an APOBEC3G complex can be detected using any known method. Suitable methods include:

a yeast two-hybrid method; a FRET assay; a BRET assay; a fluorescence quenching assay; a fluorescence anisotropy assay; an immunological assay; and an assay involving binding of a detectably labeled protein to an immobilized protein (e.g., GST-Vif).

Immunological assays, and assays involving binding of a detectably labeled protein to an immobilized protein can be arranged in a variety of ways. Immunoprecipitation assays can be designed, wherein the Vif/APOBEC3G polypeptide complex is detected by precipitating the complex with antibody specific for Vif, antibody specific for APOBEC3G, or antibody specific for a fusion partner of a Vif fusion protein and/or an antibody specific for a fusion partner of an APOBEC3G fusion polypeptide. In some embodiments, a APOBEC3G protein or a Vif protein is immobilized directly on an insoluble support. In other embodiments, a APOBEC3G protein or a Vif protein is fused or bound to a second protein, and the second protein is immobilized on an insoluble support. Insoluble supports include, but are not limited to, plastic surfaces (e.g., polystyrene, and the like) such as a multi-well plate; beads, including magnetic beads, plastic beads, and the like; membranes (e.g., polyvinylpyrrolidone, nitrocellulose, and the like); etc.

In other embodiments, the assay is a binding assay which detects binding of Vif to immobilized APOBEC3G, or which detects binding of a APOBEC3G to immobilized Vif protein. In some embodiments, the Vif polypeptide is labeled with a detectable label, and binding to an immobilized APOBEC3G polypeptide is detected. In other embodiments, the APOBEC3G polypeptide is labeled with a detectable label, and binding to immobilized Vif polypeptide is detected. In other embodiments, the Vif polypeptide is immobilized, and binding of the APOBEC3G polypeptide to the Vif polypeptide is detected using an antibody specific for the APOBEC3G polypeptide, where the antibody is either directly labeled or a secondary antibody that is labeled is used. In other embodiments, the APOBEC3G polypeptide is immobilized, and binding of the Vif polypeptide to the APOBEC3G polypeptide is detected using an antibody specific for the Vif polypeptide, where the antibody is either directly labeled or a secondary antibody that is labeled is used.

Formation of a binding complex between a Vif polypeptide and an APOBEC3G polypeptide can also be detected using fluorescence resonance energy transfer (FRET), bioluminescence resonance energy transfer (BRET), anisotropy measurements, and fluorescence quenching measurements.

FRET involves the transfer of energy from a donor fluorophore in an excited state to a nearby acceptor fluorophore. For this transfer to take place, the donor and acceptor molecules must in close proximity (e.g., less than 10 nanometers apart, usually between 10 and 100 Å apart), and the emission spectra of the donor fluorophore must overlap the excitation spectra of the acceptor fluorophore. In these embodiments, a fluorescently labeled Vif protein serves as a donor and/or acceptor in combination with a second fluorescent protein or dye, e.g., a fluorescent protein as described in Matz et al., Nature Biotechnology (October 1999) 17:969-973; a green fluorescent protein (GFP), including a "humanized" GFP; a GFP from *Aequoria victoria* or fluorescent mutant thereof, e.g., as described in U.S. Pat. Nos. 6,066,476; 6,020,192; 5,985,577; 5,976,796; 5,968,750; 5,968,738; 5,958,713; 5,919,445; 5,874,304, the disclosures of which are herein incorporated by reference; a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); other fluorescent dyes, e.g., coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum dye, etc., chemilumescent dyes, e.g., luciferases.

BRET is a protein-protein interaction assay based on energy transfer from a bioluminescent donor to a fluorescent acceptor protein. The BRET signal is measured by the amount of light emitted by the acceptor to the amount of light emitted by the donor. The ratio of these two values increases as the two proteins are brought into proximity. The BRET assay has been amply described in the literature. See, e.g., U.S. Pat. Nos. 6,020,192; 5,968,750; and 5,874,304; and Xu et al. (1999) *Proc. Natl. Acad. Sci. USA* 96:151-156. BRET assays may be performed by analyzing transfer between a bioluminescent donor protein and a fluorescent acceptor protein. Interaction between the donor and acceptor proteins can be monitored by a change in the ratio of light emitted by the bioluminescent and fluorescent proteins. In this application, the Vif protein serves as donor and/or acceptor protein.

Fluorescent Vif can be produced by generating a construct comprising a Vif and a fluorescent fusion partner, e.g., a fluorescent protein as described in Matz et al. ((1999) *Nature Biotechnology* 17:969-973), a green fluorescent protein from any species or a derivative thereof; e.g., a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); a GFP from *Aequoria victoria* or fluorescent mutant thereof, e.g., as described in U.S. Pat. Nos. 6,066,476; 6,020,192; 5,985,577; 5,976,796; 5,968,750; 5,968,738; 5,958,713; 5,919,445; 5,874,304. Generation of such a construct, and production of a Vif/fluorescent protein fusion protein is well within the skill level of those of ordinary skill in the art.

Alternatively, binding may be assayed by fluorescence anisotropy. Fluorescence anisotropy assays are amply described in the literature. See, e.g., Jameson and Sawyer (1995) *Methods Enzymol.* 246:283-300.

In some embodiments, a subject method involves detecting Vif binding to a high molecular weight complex (>700 kD) comprising APOBEC3G and cellular RNA. In these embodiments, the screening methods are typically cell-based methods. Cells are genetically modified with expression vectors that provide for production of Vif and APOBEC3G in a suitable eukaryotic cell, as described above. After allowing time for production of Vif and APOBEC3G, cells are lysed, and lysates are examined for the presence of Vif in the APOBEC3G complex. Any known method for detecting Vif association with the APOBEC3G complex is suitable. A non-limiting example is size-exclusion fast performance liquid chromatography (FPLC), as described in Example 1.

Active Agents

The present invention further provides agents that reduce or inhibit Vif activity; agents that increase the level of active APOBEC3G in a cell; and agents that convert an inactive high molecular weight APOBEC3G complex to an active low molecular weight APOBEC3G complex. Of particular interest in many embodiments are agents identified using a screening method of the invention. The subject agents are useful for inhibiting lentiviral replication, and are therefore useful for treating lentiviral infections.

In many embodiments, the agent is a small molecule, e.g., a small organic or inorganic compound having a molecular weight of more than 50 and less than about 2,500 daltons. Agents may comprise functional groups necessary for structural interaction with proteins, particularly hydrogen bonding, and may include at least an amine, carbonyl, hydroxyl or carboxyl group, and may contain at least two of the functional chemical groups. The agents may comprise cyclical carbon or heterocyclic structures and/or aromatic or polyaromatic structures substituted with one or more of the above functional groups. Agents are also found among biomolecules including peptides, saccharides, fatty acids, steroids, purines, pyrimidines, derivatives, structural analogs or combinations thereof.

In some embodiments, an active agent is a peptide (e.g., peptide inhibitors of Vif activity; peptides that increase the level of active APOBEC3G; peptides that convert an inactive HMW form of APOBEC3G to an active LMW form of APOBEC3G; etc.). Suitable peptides include peptides of from about 3 amino acids to about 50 amino acids, from about 5 amino acids to about 30 amino acids, from about 10 amino acids to about 25 amino acids, from about 25 amino acids to about 50 amino acids, from about 50 amino acids to about 75 amino acids, or from about 75 amino acids to about 100 amino acids in length. In some embodiments, the peptide is linear; in other embodiments, the peptide is cyclized. In some embodiments, the peptide is modified, e.g., comprises one or more non-peptide moieties covalently or non-covalently linked to the peptide. Suitable non-peptide moieties include, but are not limited to, polyethylene glycol (PEG) moieties; carbohydrate moieties; lipid moieties; fatty acid moieties; polysaccharide moieties; phosphate groups; and the like. In some embodiments, the active peptide is linked to a heterologous peptide, e.g., a heterologous peptide that confers increased stability or residence time in vivo; a heterologous peptide that facilitates crossing a cell membrane; a heterologous peptide that binds to a cell surface receptor; a heterologous peptide that provides for dimerization; a heterologous peptide that provides an epitope tag; a heterologous peptide that provides a detectable signal; and the like.

Peptides can include naturally-occurring and non-naturally occurring amino acids. Peptides may comprise D-amino acids, a combination of D- and L-amino acids, and various "designer" amino acids (e.g., β-methyl amino acids, Cα-methyl amino acids, and Nα-methyl amino acids, etc.) to convey special properties to peptides. Additionally, peptide may be a cyclic peptide. Peptides may include non-classical amino acids in order to introduce particular conformational motifs. Any known non-classical amino acid can be used. Non-classical amino acids include, but are not limited to, 1,2,3,4-tetrahydroisoquinoline-3-carboxylate; (2S,3S)-methylphenylalanine, (2S,3R)-methyl-phenylalanine, (2R,3S)-methyl-phenylalanine and (2R,3R)-methyl-phenylalanine; 2-aminotetrahydronaphthalene-2-carboxylic acid; hydroxy-1,2,3,4-tetrahydroisoquinoline-3-carboxylate; β-carboline (D and L); HIC (histidine isoquinoline carboxylic acid); and HIC (histidine cyclic urea). Amino acid analogs and peptidomimetics may be incorporated into a peptide to induce or favor specific secondary structures, including, but not limited to, LL-Acp (LL-3-amino-2-propenidone-6-carboxylic acid), a β-turn inducing dipeptide analog; β-sheet inducing analogs; β-turn inducing analogs; α-helix inducing analogs; γ-turn inducing analogs; Gly-Ala turn analog; amide bond isostere; tretrazol; and the like.

A peptide may be a depsipeptide, which may be a linear or a cyclic depsipeptide. Kuisle et al. (1999) *Tet. Letters* 40:1203-1206. "Depsipeptides" are compounds containing a sequence of at least two alpha-amino acids and at least one alpha-hydroxy carboxylic acid, which are bound through at least one normal peptide link and ester links, derived from the hydroxy carboxylic acids, where "linear depsipeptides" may comprise rings formed through S—S bridges, or through an hydroxy or a mercapto group of an hydroxy-, or mercapto-amino acid and the carboxyl group of another amino- or hydroxy-acid but do not comprise rings formed only through peptide or ester links derived from hydroxy carboxylic acids. "Cyclic depsipeptides" are peptides containing at least one ring formed only through peptide or ester links, derived from hydroxy carboxylic acids.

Peptides may be cyclic or bicyclic. For example, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride ($CH_2Cl_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Methods for making cyclic peptides are well known in the art.

The term "bicyclic" refers to a peptide in which there exists two ring closures. The ring closures are formed by covalent linkages between amino acids in the peptide. A covalent linkage between two nonadjacent amino acids constitutes a ring closure, as does a second covalent linkage between a pair of adjacent amino acids which are already linked by a covalent peptide linkage. The covalent linkages forming the ring closures may be amide linkages, i.e., the linkage formed between a free amino on one amino acid and a free carboxyl of a second amino acid, or linkages formed between the side chains or "R" groups of amino acids in the peptides. Thus, bicyclic peptides may be "true" bicyclic peptides, i.e., peptides cyclized by the formation of a peptide bond between the N-terminus and the C-terminus of the peptide, or they may be "depsi-bicyclic" peptides, i.e., peptides in which the terminal amino acids are covalently linked through their side chain moieties.

A desamino or descarboxy residue can be incorporated at the terminii of the peptide, so that there is no terminal amino or carboxyl group, to decrease susceptibility to proteases or to restrict the conformation of the peptide. C-terminal functional groups include amide, amide lower alkyl, amide di(lower alkyl), lower alkoxy, hydroxy, and carboxy, and the lower ester derivatives thereof, and the pharmaceutically acceptable salts thereof.

In addition to the foregoing N-terminal and C-terminal modifications, a peptide or peptidomimetic can be modified with or covalently coupled to one or more of a variety of hydrophilic polymers to increase solubility and circulation half-life of the peptide. Suitable nonproteinaceous hydrophilic polymers for coupling to a peptide include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, from about 2,000 to about 40,000 daltons, or from about 5,000 to about 20,000 daltons. The peptide can be derivatized with or coupled to such polymers using any of the methods set forth in Zallipsky, S., Bioconjugate Chem., 6:150-165 (1995); Monfardini, C, et al., Bioconjugate Chem., 6:62-69 (1995); U.S. Pat. Nos. 4,640,835; 4,496,689; 4,301,144; 4,670,417; 4,791,192; 4,179,337 or WO 95/34326.

An active peptide (e.g., peptide inhibitors of Vif activity; peptides that increase the level of active APOBEC3G; peptides that convert an inactive HMW form of APOBEC3G to an active LMW form of APOBEC3G; etc.) will in some embodiments be conjugated to decapeptides comprised of Arginine residues to allow uptake across the plasma membrane by protein transduction. Such modifications allow peptides to enter cells (e.g., cross the plasma membrane) with high efficiency.

In some embodiments, an active peptide (e.g., peptide inhibitors of Vif activity; peptides that increase the level of active APOBEC3G; peptides that convert an inactive HMW form of APOBEC3G to an active LMW form of APOBEC3G; etc.) is a peptide aptamer. Peptide aptamers are peptides or small polypeptides that act as dominant inhibitors of protein function. Peptide aptamers specifically bind to target proteins, blocking their function ability. Kolonin and Finley (1998) *Proc. Natl. Acad. Sci. USA* 95:14266-14271. Due to the highly selective nature of peptide aptamers, they may be used not only to target a specific protein, but also to target specific functions of a given protein (e.g. a protein binding function). Further, peptide aptamers may be expressed in a controlled fashion by use of promoters which regulate expression in a temporal, spatial or inducible manner.

Peptide aptamers that bind with high affinity and specificity to a target protein may be isolated by a variety of techniques known in the art. Peptide aptamers can be isolated from random peptide libraries by yeast two-hybrid screens (Xu et al., (1997) *Proc. Natl. Acad. Sci. USA* 94:12473-12478). They can also be isolated from phage libraries (Hoogenboom et al., *Immunotechnology* (1998) 4:1-20) or chemically generated peptides/libraries.

Agents that increase the level of active APOBEC3G in a eukaryotic cell include agents that prevent or reduce inclusion of APOBEC3G in high molecular weight complexes; agents that mediate disassembly of a high molecular weight APOBEC3G complex; and agents that increase production of active APOBEC3G protein by a cell.

Agents that increase production of active APOBEC3G include, but are not limited to, antibodies, e.g., antibodies to CD3 (e.g., Orthoclone OKTe® (muromonab-CD3); etc.); cytokines, e.g., IL-2 (e.g., Proleukin® IL-2 (aldesleukin)); IL-15; phorbol esters, e.g., prostratin (12-deoxyphorbol-13-acetate), phorbol-12-myristate-13-acetate, etc.; lectins, e.g., phytohemagglutinin; mitogens; etc. Combinations of two or more of the foregoing agents will in some embodiments be used to increase the level of active APOBEC3G.

Agents that promote conversion of an inactive high molecular weight APOBEC3G complex to an active low molecular weight APOBEC3G complex include agents that disrupt protein-protein interactions; RNAse; peptide fragments of APOBEC3G that inhibit APOBEC3G homodimerization; peptide fragments of APOBEC3G that inhibit association of APOBEC3G with RNA; peptide fragments of APOBEC3G that inhibit association of APOBEC3G with other polypeptides present in a high molecular weight APOBEC3G complex; short interfering RNA (siRNA) or antisense RNA targeting the RNA in the HMW APOBEC3G complex; siRNA or antisense RNA targeting mRNA that encodes a protein component of the HMW APOBEC3G complex; and the like.

Peptide agents that inhibit APOBEC3G homodimerization and/or that inhibit formation of HMW APOBEC3G complexes and/or that promote conversion of an inactive high molecular weight APOBEC3G complex to an active low molecular weight APOBEC3G complex and/or that inhibit a Vif activity include, but are not limited to, peptides corresponding to the amino terminus of APOBEC3G; and peptides corresponding to the carboxyl terminus of APOBEC3G. Exemplary, non-limiting peptides that are suitable for use include, e.g., peptides comprising from about 5 to about 10, from about 10 to about 15, from about 15 to about 20, from about 20 to about 30, or from about 30 to about 40, contiguous amino acids of the amino-terminal forty amino acids of APOBEC3G. For example, a suitable peptide comprises from about 5 to about 10, from about 10 to about 15, from about 15 to about 20, from about 20 to about 30, or from about 30 to about 40, contiguous amino acids of the following peptide: NH$_2$-MKPHFRNTVE RMYRDTFSYN FYNRPILSRR NTVWLCYEVK-COOH (SEQ ID NO:5); and variants thereof. Other exemplary peptides include peptides comprising from about from about 5 to about 10, from about 10 to about 15, from about 15 to about 20, from about 20 to about 25 contiguous amino acid of the following peptide: NH$_2$-CPFQP WDGLDEHSQD LSGRLRAILQ NQEN-COOH (SEQ ID NO:6), up to the entire length of a peptide having the sequence set forth in SEQ ID NO:6; and variants of any of the foregoing peptides (e.g., peptides that differ in amino acid sequence by from about 1 amino acid to about 10 amino acids from a foregoing peptide). Also suitable for use are any of the above-mentioned peptides in a cyclized form; and any of the above-mentioned peptides that have one or more modifications, e.g., modification by addition of one or more polyethylene glycol moieties covalently linked to the peptide (e.g., PEGylated peptides), modification by addition of one or more carbohydrate moieties, etc., as discussed above.

Peptide agents that that reduce Vif-induced degradation of APOBEC3G include peptides comprising from about 5 to about 100 contiguous amino acids of the amino-terminal portion of APOBEC3G, e.g., peptides that comprise from about 5 to about 10, from about 10 to about 20, from about 20 to about 30, from about 30 to about 40, from about 40 to about 50, from about 50 to about 60, from about 60 to about 70, from about 70 to about 80, from about 80 to about 90, or from about 90 to about 100 contiguous amino acids of the amino-terminal portion of APOBEC3G. For example, a suitable peptide agent that reduces Vif-induced degradation of APOBEC3G includes a peptide comprising from about 5 to about 10, from about 10 to about 20, from about 20 to about 30, from about 30 to about 40, from about 40 to about 50, from about 50 to about 60, from about 60 to about 70, from about 70 to about 80, from about 80 to about 90, or from about 90 to about 100 contiguous amino acids of a peptide having the sequence set forth in SEQ ID NO:7. Also suitable for use are variants of any of the foregoing peptides (e.g., peptides that differ in amino acid sequence by from about 1 amino acid to about 10 amino acids from a foregoing peptide). Also suitable for use are any of the above-mentioned peptides in a cyclized form; and any of the above-mentioned peptides that have one or more modifications, e.g., modification by addition of one or more polyethylene glycol moieties covalently linked to the peptide (e.g., PEGylated peptides), modification by addition of one or more carbohydrate moieties, etc., as discussed above.

Method of Treating a Lentivirus Infection

The present invention provides methods of treating a lentivirus infection in an individual. In some embodiments, the methods generally involve administering to an individual having a lentivirus infection, or at risk of having a lentivirus infection, a subject agent in an amount effective to inhibit Vif activity in a lentivirus-infected cell in the individual, thereby treating the lentivirus infection. In other embodiments, the methods generally involve administering to an individual having a lentivirus infection, or at risk of having a lentivirus infection, an effective amount of an agent that increases the level of active APOBEC3G in a cell that is susceptible to lentivirus infection. In other embodiments, the methods generally involve administering to an individual having a lentivirus infection, or at risk of having a lentivirus infection, an effective amount of an agent that converts a HMW APOBEC3G complex to a LMW APOBEC3G complex in a cell that is susceptible to lentivirus infection.

In some embodiments, a therapeutically effective amount of an agent that inhibits Vif activity is an amount that reduces lentivirus load in the individual and/or reduces lentivirus replication in a lentivirus-infected cell in the individual by at least about 10%, at least about 20%, at least about 30%, at least about 40%, at least about 50%, at least about 60%, at least about 70%, at least about 80%, at least about 90%, or at least about 95% or more, compared to the lentivirus load or lentivirus replication in a lentivirus-infected cell of the individual not treated with the agent.

In some embodiments, a therapeutically effective amount of an agent that increases the level of active APOBEC3G protein in a cell that is susceptible to lentivirus infection is an amount that reduces lentivirus load in the individual and/or reduces lentivirus replication in a lentivirus-infected cell in the individual by at least about 10%, at least about 20%, at least about 30%, at least about 40%, at least about 50%, at least about 60%, at least about 70%, at least about 80%, at least about 90%, or at least about 95% or more, compared to the lentivirus load or lentivirus replication in a lentivirus-infected cell of the individual not treated with the agent.

In some embodiments, a therapeutically effective amount of an agent that converts a HMW APOBEC3G complex to a LMW APOBEC3G complex in a cell that is susceptible to lentivirus infection is an amount that reduces lentivirus load in the individual and/or reduces lentivirus replication in a lentivirus-infected cell in the individual by at least about 10%, at least about 20%, at least about 30%, at least about 40%, at least about 50%, at least about 60%, at least about 70%, at least about 80%, at least about 90%, or at least about 95% or more, compared to the lentivirus load or lentivirus replication in a lentivirus-infected cell of the individual not treated with the agent.

In some embodiments, a therapeutically effective amount of an agent that inhibits Vif activity is an amount that increases the CD4$^+$ T cell count in an individual by at least about 10%, at least about 20%, at least about 30%, at least about 40%, at least about 50%, at least about 60%, at least about 70%, at least about 80%, at least about 90%, at least about 100%, at least about 2.5-fold, at least about 3-fold, at least about 3.5-fold, at least about 4-fold, at least about 5-fold, or at least about 10-fold, or more, compared to the CD4$^+$ T cell count of the individual not treated with the agent. In some embodiments, a therapeutically effective amount of an agent that inhibits Vif activity is an amount that restores the CD4$^+$ T cell count to within a normal range. In human blood, the number of CD4$^+$-T cells which is considered to be in a normal range is from about 600 to about 1500 CD4$^+$-T cells/mm$^3$ blood.

In some embodiments, a therapeutically effective amount of an agent that increases the level of active APOBEC3G in a cell is an amount that increases the CD4$^+$ T cell count in an individual by at least about 10%, at least about 20%, at least about 30%, at least about 40%, at least about 50%, at least about 60%, at least about 70%, at least about 80%, at least about 90%, at least about 100%, at least about 2.5-fold, at least about 3-fold, at least about 3.5-fold, at least about 4-fold, at least about 5-fold, or at least about 10-fold, or more, compared to the CD4$^+$ T cell count of the individual not treated with the agent. In some embodiments, a therapeutically effective amount of an agent that increases the level of active APOBEC3G in a cell is an amount that restores the CD4$^+$ T cell count to within a normal range.

In some embodiments, a therapeutically effective amount of an agent that converts a HMW APOBEC3G complex to a LMW APOBEC3G complex in a cell that is susceptible to lentivirus infection is an amount that increases the CD4$^+$ T cell count in an individual by at least about 10%, at least about 20%, at least about 30%, at least about 40%, at least about 50%, at least about 60%, at least about 70%, at least about 80%, at least about 90%, at least about 100%, at least about 2.5-fold, at least about 3-fold, at least about 3.5-fold, at least about 4-fold, at least about 5-fold, or at least about 10-fold, or more, compared to the CD4$^+$ T cell count of the individual not treated with the agent. In some embodiments, a therapeutically effective amount of an agent that converts a HMW APOBEC3G complex to a LMW APOBEC3G complex in a cell that is susceptible to lentivirus infection is an amount that restores the CD4$^+$ T cell count to within a normal range.

Treating a lentivirus infection, includes, but is not limited to, preventing lentivirus infection, reducing the probability of lentivirus infection, reducing the spread of lentivirus from an infected cell to a susceptible cell, reducing viral load in an lentivirus-infected individual, reducing an amount of virally-encoded polypeptide(s) in an lentivirus-infected individual, and increasing CD4 T cell count in an lentivirus-infected individual.

The amount of subject agent which is administered will vary with the nature of the drug. As one non-limiting example, a subject agent can be administered in the range of about 0.2 mg/kg/day to about 20 mg/kg/day. The determination of how large a dose is to be used may be determined using an animal model (e.g., a non-human primate model) and relating the dosage based on pharmacokinetics, e.g. with equations predictive of interspecies scaling. Usually, the lowest effective dose will be used.

Any of a variety of methods can be used to determine whether a treatment method is effective. For example, methods of determining whether the methods of the invention are effective in reducing lentivirus load, and/or treating an lentivirus infection, are any known test for indicia of lentivirus infection, including, but not limited to, measuring viral load, e.g., by measuring the amount of lentivirus in a biological sample, e.g., using a polymerase chain reaction (PCR) with primers specific for a lentivirus polynucleotide sequence; detecting and/or measuring a polypeptide encoded by lentivirus, e.g., p24, gp120, reverse transcriptase, using, e.g., an immunological assay such as an enzyme-linked immunosorbent assay (ELISA) with an antibody specific for the polypeptide; and measuring the CD4$^+$ T cell count in the individual.

Methods of assaying an lentivirus infection (or any indicia associated with an lentivirus infection) are known in the art, and have been described in numerous publications such as *HIV Protocols* (*Methods in Molecular Medicine*, 17) N. L. Michael and J. H. Kim, eds. (1999) Humana Press.

Formulations, Dosages, and Routes of Administration

In general, an active agent (e.g., an agent that inhibits a Vif activity; an agent that increases the level of active APOBEC3G in a cell; an agent that converts a HMW APOBEC3G complex to a LMW APOBEC3G complex; etc.) is prepared in a pharmaceutically acceptable composition for delivery to a host. The terms "active agent," "drug," "agent," "therapeutic agent," and the like are used interchangeably herein. Pharmaceutically acceptable carriers preferred for use with a subject agent may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising a subject agent may also be lyophilized using means well known in the art, for subsequent reconstitution and use according to the invention.

Formulations

An active agent (e.g., an agent that inhibits a Vif activity; an agent that increases the level of active APOBEC3G in a cell; an agent that converts a HMW APOBEC3G complex to a LMW APOBEC3G complex; etc.) is administered to an individual in need thereof in a formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

In the subject methods, an active agent (e.g., an agent that inhibits a Vif activity; an agent that increases the level of active APOBEC3G in a cell; an agent that converts a HMW APOBEC3G complex to a LMW APOBEC3G complex; etc.) may be administered to the host using any convenient means capable of resulting in the desired reduction in a Vif activity and/or increase in the level of active APOBEC3G. Thus, an active agent (e.g., an agent that inhibits a Vif activity; an agent that increases the level of active APOBEC3G in a cell; an agent that converts a HMW APOBEC3G complex to a LMW APOBEC3G complex; etc.) can be incorporated into a variety of formulations for therapeutic administration. More particularly, an active agent (e.g., an agent that inhibits a Vif activity; an agent that increases the level of active APOBEC3G in a cell; an agent that converts a HMW APOBEC3G complex to a LMW APOBEC3G complex; etc.) can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, an active agent (e.g., an agent that inhibits a Vif activity; an agent that increases the level of active APOBEC3G in a cell; an agent that converts a HMW APOBEC3G complex to a LMW APOBEC3G complex; etc.) may be administered in the form of its pharmaceutically acceptable salts, or it may also be used alone or in appropriate association, as well as in combination, with other pharmaceutically active compounds. The following methods and excipients are merely exemplary and are in no way limiting.

For oral preparations, an active agent (e.g., an agent that inhibits a Vif activity; an agent that increases the level of active APOBEC3G in a cell; an agent that converts a HMW APOBEC3G complex to a LMW APOBEC3G complex; etc.) can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent (e.g., an agent that inhibits a Vif activity; an agent that increases the level of active APOBEC3G in a cell; an agent that converts a HMW APOBEC3G complex to a LMW APOBEC3G complex; etc.) can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. An active agent (e.g., an agent that inhibits a Vif activity; an agent that increases the level of active APOBEC3G in a cell; an agent that converts a HMW APOBEC3G complex to a LMW APOBEC3G complex; etc.) can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the active agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an active agent, calculated in an amount sufficient to produce the desired effect in association with a pharmaceutically acceptable diluent, carrier or vehicle. The specifications for a given active agent will depend in part on the particular compound employed and the effect to be achieved, and the pharmacodynamics associated with each compound in the host.

Other modes of administration will also find use with the subject invention. For instance, an active agent (e.g., an agent that inhibits a Vif activity; an agent that increases the level of active APOBEC3G in a cell; an agent that converts a HMW APOBEC3G complex to a LMW APOBEC3G complex; etc.)

can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An active agent (e.g., an agent that inhibits a Vif activity; an agent that increases the level of active APOBEC3G in a cell; an agent that converts a HMW APOBEC3G complex to a LMW APOBEC3G complex; etc.) can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

An active agent (e.g., an agent that inhibits a Vif activity; an agent that increases the level of active APOBEC3G in a cell; an agent that converts a HMW APOBEC3G complex to a LMW APOBEC3G complex; etc.) will in some embodiments be formulated for vaginal delivery. A subject formulation for intravaginal administration is formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

A subject formulation comprising an active agent includes one or more of an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

Tablets comprising an active agent may be coated with a suitable film-forming agent, e.g., hydroxypropylmethyl cellulose, hydroxypropyl cellulose or ethyl cellulose, to which a suitable excipient may optionally be added, e.g., a softener such as glycerol, propylene glycol, diethylphthalate, or glycerol triacetate; a filler such as sucrose, sorbitol, xylitol, glucose, or lactose; a colorant such as titanium hydroxide; and the like.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range is one which provides up to about 1 μg to about 100 mg, e.g., from about 1 μg to about 25 μg, from about 25 μg to about 50 μg, from about 50 μg to about 100 μg, from about 100 μg to about 250 μg, from about 250 μg to about 500 μg, from about 500 μg to about 1 mg, from about 1 mg to about 25 mg, from about 25 mg to about 50 mg, or from about 50 mg to about 100 mg, of an active agent (e.g., an agent that inhibits a Vif activity; an agent that increases the level of active APOBEC3G in a cell; an agent that converts a HMW APOBEC3G complex to a LMW APOBEC3G complex; etc.) can be administered in a single dose. Alternatively, a target dosage of an active agent (e.g., an agent that inhibits a Vif activity; an agent that increases the level of active APOBEC3G in a cell; an agent that converts a HMW APOBEC3G complex to a LMW APOBEC3G complex; etc.) can be considered to be about in the range of about 0.1-1000 μM, about 0.5-500 μM, about 1-100 μM, or about 5-50 μM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, a single dose of an active agent is administered. In other embodiments, multiple doses of an active agent are administered. Where multiple doses are administered over a period of time, an active agent is administered twice daily (qid), daily (qd), every other day (qod), every third day, three times per week (tiw), or twice per week (biw) over a period of time. For example, an active agent is administered qid, qd, qod, tiw, or biw over a period of from one day to about 2 years or more. For example, an active agent is administered at any of the aforementioned frequencies for one week, two weeks, one month, two months, six months, one year, or two years, or more, depending on various factors.

As one non-limiting example, where an active agent increases the level of APOBEC3G, the agent is in some embodiments an anti-CD3 antibody, such as Orthoclone OKT3® (muromonab-CD3). In these embodiments, suitable dosage of OKT3 is about 5 mg/day, administered in a single bolus injection intravenously, for a period of from about 10 days to about 14 days.

Routes of Administration

An active agent (e.g., an agent that inhibits a Vif activity; an agent that increases the level of active APOBEC3G in a cell; an agent that converts a HMW APOBEC3G complex to a LMW APOBEC3G complex; etc.) is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, transdermal, subcutaneous, intradermal, topical application, intravenous, vaginal, nasal, and other parenteral routes of administration. Suitable routes of administration also include oral and rectal routes. Routes of administration may be combined, if desired, or adjusted depending upon the agent and/or the desired effect. The composition can be administered in a single dose or in multiple doses.

An active agent (e.g., an agent that inhibits a Vif activity; an agent that increases the level of active APOBEC3G in a cell; an agent that converts a HMW APOBEC3G complex to a LMW APOBEC3G complex; etc.) can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, vaginal, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as the number of viral particles per unit blood. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, and primates (e.g., humans, chimpanzees, and monkeys), that are susceptible to lentivirus infection. In many embodiments, the hosts will be humans.

Combination Therapies

A subject agent can be administered to an individual in combination (e.g., in the same formulation or in separate formulations) with at least a second therapeutic agent ("combination therapy"). The subject agent can be administered in admixture with a second therapeutic agent or can be administered in a separate formulation. When administered in separate formulations, a subject agent and a second therapeutic agent can be administered substantially simultaneously (e.g., within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, or about 72 hours, or more. Effective amounts of a therapeutic agent are as described above.

Therapeutic agents that can be administered in combination therapy, such as anti-inflammatory, anti-viral, anti-fungal, anti-mycobacterial, antibiotic, amoebicidal, trichomonocidal, analgesic, anti-neoplastic, anti-hypertensives, anti-microbial and/or steroid drugs, to treat antiviral infections. In some embodiments, patients with a viral or bacterial infection are treated with a combination of one or more subject agents with one or more of the following; beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide™), trisodium phosphonoformate (Foscamet™), famcyclovir, pencyclovir, valacyclovir, nucleic acid/replication inhibitors, interferon, zidovudine (AZT, Retrovirm), zidovudine/lamivudine (Combivir), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), lopinavir/ritonavir (Kaletra), trizivir, rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof. Anti-HIV agents are those in the preceding list that specifically target a function of one or more HIV proteins.

In some embodiments, a subject agent is administered in combination therapy with two or more anti-HIV agents. For example, a subject agent can be administered in combination therapy with one, two, or three nucleoside reverse transcriptase inhibitors (e.g., Combivir, Epivir, Hivid, Retrovir, Videx, Zerit, Ziagen, etc.). A subject agent can be administered in combination therapy with one or two non-nucleoside reverse transcriptase inhibitors (e.g., Rescriptor, Sustiva, Viramune, etc.). A subject agent can be administered in combination therapy with one or two protease inhibitors (e.g., Agenerase, Crixivan, Fortovase, Invirase, Kaletra, Norvir, Viracept, etc.). A subject agent can be administered in combination therapy with a protease inhibitor and a nucleoside reverse transcriptase inhibitor. A subject agent can be administered in combination therapy with a protease inhibitor, a nucleoside reverse transcriptase inhibitor, and a non-nucleoside reverse transcriptase inhibitor. A subject agent can be administered in combination therapy with a protease inhibitor and a non-nucleoside reverse transcriptase inhibitor. Other combinations of a subject inhibitor with one or more of a protease inhibitor, a nucleoside reverse transcriptase inhibitor, and a non-nucleoside reverse transcriptase inhibitor are contemplated.

Kits, Containers, Devices, Delivery Systems

Kits with unit doses of the active agent, e.g. in oral, vaginal, rectal, transdermal, or injectable doses (e.g., for intramuscular, intravenous, or subcutaneous injection), are provided. In such kits, in addition to the containers containing the unit doses will be an informational package insert describing the use and attendant benefits of the drugs in treating an HIV infection. Suitable active agents and unit doses are those described herein above.

In many embodiments, a subject kit will further include instructions for practicing the subject methods or means for obtaining the same (e.g., a website URL directing the user to a webpage which provides the instructions), where these instructions are typically printed on a substrate, which substrate may be one or more of: a package insert, the packaging, formulation containers, and the like.

In some embodiments, a subject kit includes one or more components or features that increase patient compliance, e.g., a component or system to aid the patient in remembering to take the active agent at the appropriate time or interval. Such components include, but are not limited to, a calendaring system to aid the patient in remembering to take the active agent at the appropriate time or interval.

The present invention provides a delivery system comprising an active agent that inhibits a Vif activity, an agent that increases the level of active APOBEC3G in a cell, or an active agent that converts a HMW APOBEC3G complex to a LMW APOBEC3G (enzymatically active) complex. In some embodiments, the delivery system is a delivery system that provides for injection of a formulation comprising an active agent subcutaneously, intravenously, or intramuscularly. In other embodiments, the delivery system is a vaginal delivery system.

In some embodiments, an active agent is packaged for oral administration. The present invention provides a packaging unit comprising daily dosage units of an active agent. For example, the packaging unit is in some embodiments a conventional blister pack or any other form that includes tablets, pills, and the like. The blister pack will contain the appropriate number of unit dosage forms, in a sealed blister pack with a cardboard, paperboard, foil, or plastic backing, and enclosed in a suitable cover. Each blister container may be numbered or otherwise labeled, e.g., starting with day 1.

In some embodiments, a subject delivery system comprises an injection device. Exemplary, non-limiting drug delivery devices include injections devices, such as pen injectors, and needle/syringe devices. In some embodiments, the invention provides an injection delivery device that is pre-loaded with a formulation comprising an effective amount of an active agent that inhibits a Vif activity or that increases the level of active APOBEC3G in a cell or that converts a HMW APOBEC3G complex to a LMW APOBEC3G complex. For example, a subject delivery device comprises an injection device pre-loaded with a single dose of an active agent that inhibits a Vif activity, or that increases the level of active APOBEC3G, or that converts a HMW APOBEC3G complex to a LMW APOBEC3G complex. A subject injection device can be re-usable or disposable.

Pen injectors are well known in the art. Exemplary devices which can be adapted for use in the present methods are any of a variety of pen injectors from Becton Dickinson, e.g., BD™ Pen, BD™ Pen II, BD™ Auto-Injector; a pen injector from Innoject, Inc.; any of the medication delivery pen devices discussed in U.S. Pat. Nos. 5,728,074, 6,096,010, 6,146,361, 6,248,095, 6,277,099, and 6,221,053; and the like. The medication delivery pen can be disposable, or reusable and refillable.

The present invention provides a vaginal delivery system for vaginal delivery of an active agent (e.g., an agent that inhibits a Vif activity; an agent that increases the level of active APOBEC3G in a cell; an agent that converts a HMW APOBEC3G complex to a LMW APOBEC3G complex; etc.) to the vagina of an individual. The delivery system comprises a device for insertion into the vagina. In some embodiments, the delivery system comprises an applicator for delivery of a formulation into the vagina; and a container that contains a formulation comprising an active agent (e.g., an agent that inhibits a Vif activity; an agent that increases the level of active APOBEC3G in a cell; an agent that converts a HMW APOBEC3G complex to a LMW APOBEC3G complex; etc.). In these embodiments, the container (e.g., a tube) is adapted for delivering a formulation into the applicator. In other embodiments, the delivery system comprises a device that is inserted into the vagina, which device includes an active agent (e.g., an agent that inhibits a Vif activity; an agent that increases the level of active APOBEC3G in a cell; an agent that converts a HMW APOBEC3G complex to a LMW APOBEC3G complex; etc.). For example, the device is coated with, impregnated with, or otherwise contains a formulation comprising the active agent.

In some embodiments, the vaginal delivery system is a tampon or tampon-like device that comprises a subject formulation. Drug delivery tampons are known in the art, and any such tampon can be used in conjunction with a subject drug delivery system. Drug delivery tampons are described in, e.g., U.S. Pat. No. 6,086,909 If a tampon or tampon-like device is used, there are numerous methods by which an active agent (e.g., an agent that inhibits a Vif activity; an agent that increases the level of active APOBEC3G in a cell; an agent that converts a HMW APOBEC3G complex to a LMW APOBEC3G complex; etc.) can be incorporated into the device. For example, the drug can be incorporated into a gel-like bioadhesive reservoir in the tip of the device. Alternatively, the drug can be in the form of a powdered material positioned at the tip of the tampon. The drug can also be absorbed into fibers at the tip of the tampon, for example, by dissolving the drug in a pharmaceutically acceptable carrier and absorbing the drug solution into the tampon fibers. The drug can also be dissolved in a coating material which is applied to the tip of the tampon. Alternatively, the drug can be incorporated into an insertable suppository which is placed in association with the tip of the tampon.

In other embodiments, the drug delivery device is a vaginal ring. Vaginal rings usually consist of an inert elastomer ring coated by another layer of elastomer containing an active agent (e.g., an agent that inhibits a Vif activity; an agent that increases the level of active APOBEC3G in a cell; an agent that converts a HMW APOBEC3G complex to a LMW APOBEC3G complex; etc.) to be delivered. The rings can be easily inserted, left in place for the desired period of time (e.g., up to 7 days), then removed by the user. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered.

In other embodiments, a subject vaginal delivery system is a vaginal sponge. The active agent is incorporated into a silicone matrix which is coated onto a cylindrical drug-free polyurethane vaginal sponge, as described in the literature.

Pessaries, tablets and suppositories are other examples of drug delivery systems which can be used in the present invention. These systems have been described extensively in the literature.

Bioadhesive microparticles constitute still another drug delivery system suitable for use in the present invention. This system is a multi-phase liquid or semi-solid preparation which does not seep from the vagina as do many suppository formulations. The substances cling to the wall of the vagina and release the drug (e.g., an agent that inhibits a Vif activity; an agent that increases the level of active APOBEC3G in a cell; an agent that converts a HMW APOBEC3G complex to a LMW APOBEC3G complex; etc.) over a period of time. Many of these systems were designed for nasal use but can be used in the vagina as well (e.g. U.S. Pat. No. 4,756,907). The system may comprise microspheres with an active agent; and a surfactant for enhancing uptake of the drug. The microparticles have a diameter of 10-100 pm and can be prepared from starch, gelatin, albumin, collagen, or dextran.

Another system is a container comprising a subject formulation (e.g., a tube) that is adapted for use with an applicator. The active agent (e.g., an agent that inhibits a Vif activity; an agent that increases the level of active APOBEC3G in a cell; an agent that converts a HMW APOBEC3G complex to a LMW APOBEC3G complex; etc.) is incorporated into creams, lotions, foams, paste, ointments, and gels which can be applied to the vagina using an applicator. Processes for preparing pharmaceuticals in cream, lotion, foam, paste, ointment and gel formats can be found throughout the literature. An example of a suitable system is a standard fragrance free lotion formulation containing glycerol, ceramides, mineral oil, petrolatum, parabens, fragrance and water such as the product sold under the trademark JERGENS™ (Andrew Jergens Co., Cincinnati, Ohio). Suitable nontoxic pharmaceutically acceptable systems for use in the compositions of the present invention will be apparent to those skilled in the art of pharmaceutical formulations and examples are described in Remington's Pharmaceutical Sciences, 19th Edition, A. R. Gennaro, ed., 1995. The choice of suitable carriers will depend on the exact nature of the particular vaginal dosage form desired, e.g., whether the active ingredient(s) is/are to be formulated into a cream, lotion, foam, ointment, paste, solution, or gel, as well as on the identity of the active ingredient(s). Other suitable delivery devices are those described in U.S. Pat. No. 6,476,079.

Subjects Suitable for Treatment

The methods of the present invention are suitable for treating individuals who have a lentiviral infection; who are at risk of contracting a lentiviral infection; and who were treated for a lentiviral infection, but who relapsed. Such individuals include, but are not limited to, individuals with healthy, intact immune systems, but who are at risk for becoming HIV infected ("at-risk" individuals). At-risk individuals include, but are not limited to, individuals who have a greater likelihood than the general population of becoming HIV infected. Individuals at risk for becoming HIV infected include, but are not limited to, individuals at risk for HIV infection due to sexual activity with HIV-infected individuals; intravenous drug users; individuals who may have been exposed to HIV-infected blood, blood products, or other HIV-contaminated body fluids; and babies who are being nursed by HIV-infected mothers. Individuals suitable for treatment include individuals infected with, or at risk of becoming infected with, HIV-1 and/or HIV-2 and/or HIV-3, or any variant thereof.

Individuals suitable for treatment with the methods of the invention also include individuals who have a lentiviral infection that is refractory to treatment with other anti-viral therapies.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec., second(s); min, minute(s); h or hr, hour(s); and the like.

Example 1

HIV-1 Vif Blocks the Antiviral Activity of APOBEC3G

Experimental Procedures

Plasmids

The pNL4-3 and pNL4-3 ΔVif (also known has p-NLND) expression vectors have been previously described. Adachi et al. (1991). Arch Virol 117, 45-58; and Sakai et al. (1993) *J Virol* 67, 1663-1666. pcDNA3.1 APOBEC3G-HA and APOBEC3G expression vectors were produced by excising an APOBEC3G-HA cassette using the XhoI/EcoRI restriction sites present in the NG/C15 retroviral vector (Sheehy et al. (2002) *Nature* 418, 646-650) and then cloning of the fragment into the same restriction enzyme sites in pcDNA3.1. To prepare the pCMV4-HA-APOBEC3G vector, APOBEC3G cDNA was amplified by PCR from an H9 cDNA library and then inserted into the HindIII and XbaI sites of the pCMV4 vector. GST-Vif was prepared by polymerase chain reaction (PCR) amplification of the Vif coding region present in a pNL4-3 vector followed by insertion of this amplicon into the EcoRI and NheI sites of the pBC vector (Chatton et al. (1995) *Biotechniques* 18, 142-145). The sequences of each insert prepared using PCR were confirmed by DNA sequencing.

Cell Lines, Spinoculation, and Preparation of Highly Purified Virions

H9, Supt-1, Jurkat, and 293T cells were maintained using standard tissue culture techniques. Fresh human peripheral blood lymphocytes (PBLs) were maintained in complete RPMI media (10% FBS) supplemented with IL-2 (5 ug/L) (Roche Diagnostics). A portion of PBLs was activated with phytohemagglutinin (PHA) (5 μg/ml) for 24 hours prior to use. HIV-1 wt and HIV-1 ΔVif viruses were pseudotyped with the vesicular stomatitis virus-G (VSV-G) envelope by calcium phosphate mediated cotransfection of 293T cells with expression vector DNAs encoding VSV-G and pNL4-3 or pNL4-3 ΔVif. After 48 hours of culture, virus-containing supernatants were harvested, clarified by centrifugation at 500×g for 5 minutes and filtered through 0.2 micron-pore-sized filters. The virus-containing supernatant was then incubated with 0.4×10⁶ H9 cells/well in 48 well plates and centrifuged at low speed for 90 minutes at 34° C. The cells were then washed with phosphate-buffered saline (PBS) and incubated in complete medium for 40 hours at 37° C. The cells were then pelleted by centrifugation at 500×g for 5 min., washed in PBS, and lysed for immunoblotting and nuclear-cytoplasmic fractionation studies. Highly purified virions were obtained from the virus-containing supernatant using the discontinuous step iodixanol gradient purification method previously described (Dettenhofer and Yu (1999) *J Virol* 73, 1460-1467. Fractions from the iodixanol gradient were then subjected to an additional round of ultracentrifugation for 90 minutes at 4° C., and the pellets were resuspended in 30 µl of Laemmli loading buffer prior to analysis by sodium dodecyl sulfate-polyacrylamide gel electrophoresis (SDS-PAGE).

Antibodies, Immunoblotting Analysis, Intracellular Anti-p24 Immunostaining, and FPLC Anti-APOBEC3G antibody was prepared by immunizing and boosting rabbits with a synthetic peptide corresponding to the C terminal 16 amino acids of human APOBEC3G [(C)-QDLSGRLRAILQNQEN; SEQ ID NO:8]. Serum was obtained after 42 days and tested for immunoreactivity with H9 cellular lysates. As a negative control, the same lysates were tested for immunoreactivity with pre-immune serum from the same rabbits (Antibody Solutions). Polyclonal anti-Vif antiserum (Goncalves et al. (1994) *J Virol* 68, 704-712). Rabbit anti-Nef antiserum has been previously described (Bresnahan et al., 1998). Mouse monoclonal anti-p24 Gag ascites was a generous gift from BeckmanCoulter. Other antibodies used included rabbit anti-HA (Santa Cruz); mouse anti-HA (12CA5, Roche); and mouse anti-ubiquitin (Santa Cruz). Lysis buffers used for immunoblotting and fast protein liquid chromatography (FPLC) were (1) 100-400 mM NaCl, 50 mM Hepes, 0.2% NP40, 0-5 mM EDTA, 0.1 mM PMS, plus complete protease inhibitor cocktail (Roche)(1 tablet per 50 ml buffer) or (2) 50 mM Hepes, pH 7.2, 135 mM NaCl, 1% Triton X-100, 0.5% deoxycholate, 10% glycerol, 1 mM EDTA, 1× protease inhibitor cocktail (Calbiochem). The FPLC running buffer consisted of 50 mM Hepes, pH 7.4; 250 mM NaCl; 0.1% NP40, 1 mM DTT; and 10% glycerol. Intracellular anti-24 immunostaining of H9 cells was performed as previously described (Eckstein et al. (2001) *J. Exp. Med.* 194:1407-1419). Cell lysates for FPLC analysis were centrifuged twice in a microfuge at maximum speed for 10 minutes and then applied to a calibrated Superose 6 HR 10/30 or Superose 12 HR 10/30 pre-packed gel filtration column (AKTA, Amersham Pharmacia Biotech). One ml samples were collected from the column for subsequent analysis.

Protein Expression Assays 293T cells were transfected with the indicated amounts of expression vector DNA using the calcium phosphate method. Lysis buffers used for immunoblotting were (1) 100-400 mM NaCl, 50 mM Hepes, 0.2% NP40, 0-5 mM EDTA, 0.1 mM PMSF, plus complete protease inhibitor cocktail (Roche)(1 tablet/50 ml buffer) or (2) 50 mM Hepes, pH 7.2, 135 mM NaCl, 1% Triton X-100, 0.5% deoxycholate, 10% glycerol, 1 mM EDTA, 1× protease inhibitor cocktail (Calbiochem). Samples were analyzed using standard SDS-PAGE techniques.

For the proteasome inhibitor experiments in transiently transfected cells, 293T cells were transiently transfected with 0.1 µg of APOBEC3G-HA DNA, 2 µg of control vector DNA and 2 µg of either pcDNA3.1 Vif DNA vector or an additional 2 µg of control vector DNA. Twenty-four hours after transfection, the cells were treated with the indicated inhibitor and harvested 15 hours later. For the proteasome inhibitor experiments using infected H9 cells, H9 cells were infected by spinoculation as described above. Forty-four hours after infection, the cells were treated for 16 hours with either dimethylsulfoxide (DMSO) (0.1%) or 0.25 µM epoxomicin. All of the inhibitors (ALLN, MG132, epoxomicin, Calpain Inhibitor III, and clasto-Lactacystin-β-Lactone) were purchased from CalBiochem and were dissolved in DMSO.

Intracellular anti-24 Gag immunostaining of H9 cells was performed as described (Eckstein et al., 2001, supra). Briefly, H9 cells were harvested, washed and permeabilized by incubation at room temperature for 30 min in PermeaFix (Ortho Diagnostic Systems, Raritan, N.J.). After two additional washes, the cells were incubated with FITC-conjugated anti-p24-Gag antibody (Coulter) for 30 min at room temperature. After additional wash steps, the cells were then analyzed by flow cytometry.

To analyze subcellular distribution of the APEBEC3G, H9 or transfected 293T cells were washed and suspended in swelling buffer (10 mM HEPES pH 7.9, 1.5 mM $MgCl_2$, 10 mM KCL, protease inhibitor cocktail and PMSF). The cells were allowed to swell for 10 min on ice before being vortexed in the presence of 0.4% NP-40. The lysate was layered on top of 1 ml of 1% sucrose in swelling buffer and then centrifuged at 3150 RPM in a Beckman GS-6R centrifuge.

Northern Analysis

RNA was extracted from $10^7$ infected or uninfected H9 or Supt-1 cells using the Qiagen RNAeasy RNA extraction kit. The RNA was then separated on a 1% formaldehyde-agarose gel, transferred to a nitrocellulose membrane and probed with a $^{32}P$-labeled APOBEC3G cDNA. Hybridizing bands on the membrane were then visualized using autoradiography.

Pulse-Chase and Pulse Radiolabeling Experiments

HEK 293 cells were co-transfected with 1 µg of APOBEC3G-HA expression vector and 8 µg of either Vif or control expression vectors. The transfected HEK 293 cells were pre-incubated for one hour in labeling media (DMEM without methionine and cysteine (Cellgro) plus 10% dialyzed FBS). Each sample was subsequently pulse-labeled for 30 min in labeling media containing 250 µCi EasyTag™ EXPRESS $^{35}S$ Protein Labeling Mix containing radiolabeled methionine and cysteine (PerkinElmer). The initial pulse-labeled (t=0) samples were harvested. The remaining radiolabeled samples were incubated with chase media (DMEM plus 10% FBS with 4.02 mM methionine (20×) and 3 mM cysteine (15×)) and harvested at various time points. For the pulse-label experiment, each sample was pulse-labeled for 15 min and then harvested immediately.

The harvested cell pellets were lysed in Buffer A (50 mM HEPES, 135 mM NaCl, 1% Triton X-100, 0.5% sodium deoxycholate, 10% glycerol, 1 mM EDTA, (pH 7.2) plus protease inhibitor cocktail set I (Calbiochem)) for 15 minutes on ice. The cell lysates were clarified at 14,000×g, at 4° C. for 10 min. Protein determinations were performed using the BCA Protein Assay Reagents (Pierce). Immunoprecipitations (IP) were set up at equal protein concentration/volume in the presence of anti-HA monoclonal antibodies (262K Mab, Cell Signaling Technology) and incubated on ice. All subsequent spin/wash steps were performed at 4° C. The IPs were washed four times with Buffer A and eluted with 1×SDS-PAGE sample buffer. The samples were analyzed by SDS-PAGE and the gels fixed for at least 1 hour before treatment with Amplify fluorographic reagent (Amersham Biosciences) and gel drying. The dried gels were subjected to autoradiography and the scanned images were quantified using Scion Image software (version 1.62).

In Vitro Translation

Vif or control GST protein was initially transcribed and translated for 90 min using the Promega TNT T7-coupled Reticulocyte Lysate system according to the manufacturer's instructions. The pre-synthesized Vif or GST was then added to a new transcription/translation mix programmed with APOBEC3G DNA on ice. The reactions were then transferred to a 30° C. water bath and allowed to proceed for 15 or 30 min. The proteins were separated by SDS-PAGE, and the gel was analyzed by autoradiography.

Results

Native APOBEC3G Protein is Selectively Expressed in Nonpermissive T Cells and Principally Localizes in the Cytoplasm To address the question of how Vif overcomes the antiviral activity of APOBEC3G, a rabbit polyclonal antibody was developed, which was directed to the C terminal 16 amino acids of the ~46 kD APOBEC3G protein. Although a previous study demonstrated that APOBEC3G mRNA is expressed in nonpermissive but not in permissive cells (Sheehy et al., 2002, supra), it remained unknown whether APOBEC3G protein was actually expressed in nonpermissive cells. Accordingly, the expression pattern of APOBEC3G protein was assessed by immunoblotting lysates from permissive and nonpermissive cell types with the anti-APOBEC3G antibody. The results are depicted in FIG. 1A.

Figure 1A:
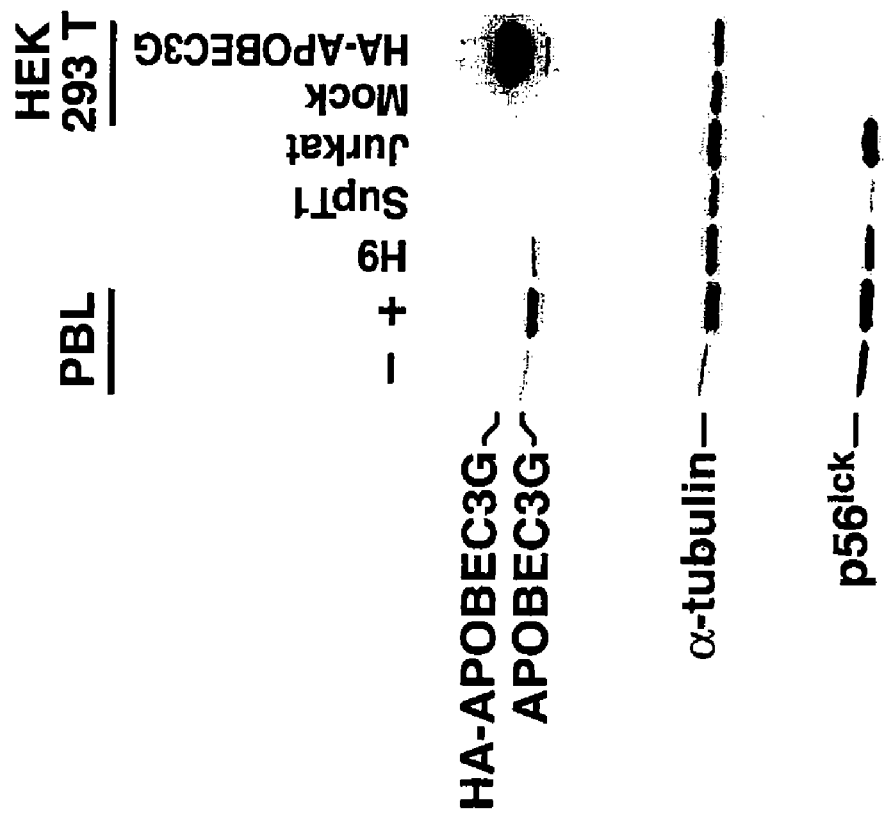

The rabbit anti-APOBEC3G antibody specifically reacted with a ~46 kD protein that was present in nonpermissive PHA-stimulated primary peripheral blood lymphocytes (PBLs) and H9 cells (FIG. 1A, lanes 2 and 3). In contrast, this 46 kD protein was not detected in lysates prepared from permissive Supt-1, Jurkat, or 293T cells (FIG. 1A, lanes 4-6), nor was it detected in nonpermissive cell types when pre-immune serum from the same rabbit was used. The levels of α-tubulin expression were similar between the nonpermissive and permissive cell lysates, confirming equal loading. Of note, PHA stimulation of the PBLs (designated by + symbol) resulted in increased expression of endogenous APOBEC3G (compare lanes 1 and 2). Although α-tubulin was expressed at lower levels in these unstimulated PBL lysates, $p56^{lck}$ was nearly equally expressed in the unstimulated versus PHA-activated PBL lysates, suggesting that APOBEC3G is inducibly expressed in response to mitogen activation of primary PBLs.

To further confirm the specificity of the anti-APOBEC3G antibody, cellular lysates from 293T cells transfected with either control vector DNA (mock) or HA-APOBEC3G expression vector were immunoblotted. The anti-APOBEC3G antibody reacted with a ~50 kD protein present in the lysate from the HA-APOBEC3G transfected cells while lysates from the mock-transfected 293T cells did not exhibit a comparable protein band (FIG. 1A, lanes 6 and 7). Together, these findings demonstrate that the rabbit anti-APOBEC3G antibody specifically reacts with endogenous human APOBEC3G, confirm that endogenous APOBEC3G protein is expressed in nonpermissive cells, and reveal that APOBEC3G protein expression is upregulated following PHA stimulation of primary PBLs.

Next, the intracellular localization of APOEC3G was analyzed by immunoblotting nuclear and cytoplasmic fractions isolated from nonpermissive H9 cells and permissive SupT1 cells. The results are shown in FIG. 1B. Tubulin and histone H3 were employed as cytoplasmic and nuclear markers, respectively, to monitor the purity of these subcellular fractions. The endogenous APOBEC3G protein was not detectably expressed in either the nucleus or the cytoplasm of permissive SupT1 cells. Conversely, in nonpermissive H9 cells, APOBEC3G was readily detected and was principally localized to the cytoplasm. However, small amounts of APOBEC3G were present in the nucleus. Since the expression of tubulin and histone H3 shows that the nuclear and cytoplasmic fractions were not cross contaminated, these findings raise the possibility that the APOBEC3G protein may in fact shuttle into and out of the nucleus. Nevertheless, APOBEC3G is predominantly expressed in the cytoplasmic compartment.

FIGS. 1A and 1B. Characterization of the expression and localization of APOBEC3G. (A) Immunoblot analysis of APOBEC3G expression in nonpermissive and permissive cells. The indicated cell types were lysed and analyzed by SDS-PAGE followed by immunoblotting with anti-APOBEC3G antiserum, anti-tubulin and anti-$p56^{lck}$. To confirm specificity of the antiserum, 293T cells were transfected with a HA-APOBEC3G expression vector. PBL, peripheral blood lymphocytes. (B) Subcellular localization of APOBEC3G. Nuclear and cytoplasmic fractions were prepared from H9 (nonpermissive) or Supt-1 (permissive) cells and analyzed by immunoblotting with antiserum specific for APOBEC3G. Immunoblotting with anti-α-tubulin and anti-Histone H3 confirmed the integrity of the cytoplasmic and nuclear fractions. Note that APOBEC3G is predominantly localized in the cytoplasm although small amounts of this protein are also present in the nucleus.

Vif Prevents Intravirion Incorporation of Endogenous APOBEC3G Protein

Figure 2:
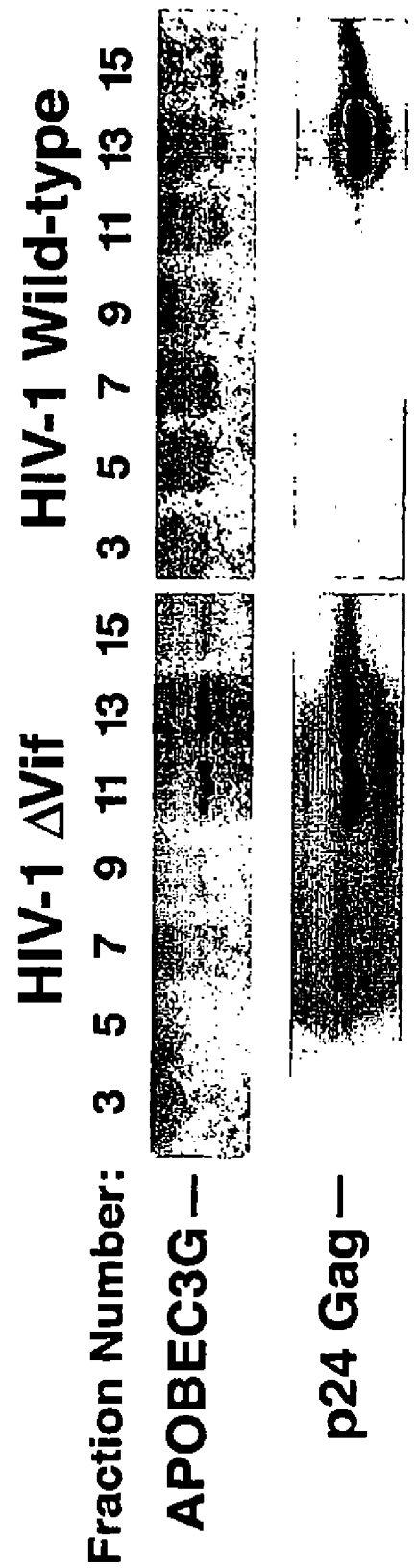
FIG. 2 depicts the inhibitory effect of Vif on incorporation of full-length endogenous APOBEC3G into virions.

Recent studies have demonstrated that APOBEC3G inhibits the infectivity of HIV-1 ΔVif virions produced by nonpermissive cells by causing extensive hypermutation of newly-synthesized HIV-1 DNA transcripts formed during reverse transcription in the subsequent target cell (Harris et al., 2003; Lecossier et al., 2003; Mangeat et al., 2003; Zhang et al., 2003). These findings support the conclusion that an antiviral factor is incorporated into the ΔVif virions and transported to the next target cell (Harris et al., 2003; Lecossier et al., 2003; Mangeat et al., 2003; Zhang et al., 2003, supra). In this regard, APOBEC3G-HA has been detected in virions produced by transfected 293T cells in both the presence and absence of Vif (Sheehy et al., 2002, supra). However, given the unnaturally high levels of APOBEC3G protein that are expressed in transfected 293T cells, this system may not faithfully recapitulate the actual biological events. It was hypothesized that Vif may prevent endogenous APOBEC3G from being incorporated into the virion and tested this possibility in a more physiologically relevant cellular setting. H9 cells were infected with vesicular stomatitis protein-G (VSV-G) pseudotyped HIV-$1_{NL4-3}$ wt or VSV-G-HIV-$1_{NL4-3}$-ΔVif viruses. To isolate highly purified virions, supernatants from infected H9 cells were collected and applied to discontinuous iodixanol gradients. Sequential fractions from these gradients were analyzed for p24Gag content as a marker of HIV-1 wt and Δvif virions. Probing of these fractions revealed the presence of endogenous APOBEC3G in the HIV-1 ΔVif virions (FIG. 2). Conversely, virtually no full-length APOBEC3G protein was present in the HIV-1 wt virions. These findings indicate that Vif expression in the producer cell markedly impairs the incorporation of APOBEC3G protein into newly formed virions.

FIG. 2. Vif prevents incorporation of full-length endogenous APOBEC3G into virions. HIV-1 and HIV-1 ΔVif virions were prepared by spinoculation infection of H9 cells with VSV-G pseudyotyped-HIV-1 or HIV-1 ΔVif viruses. Forty eight hours post-infection, virus-containing supernatants were collected and virions were purified on discontinous step iodixanol gradients. Gradient fractions were immunoblotted with anti-p24 Gag antibody to identify virions and anti-APOBEC3G antiserum to evaluate virion incorporation of this antiviral factor. Note that APOBEC3G is markedly diminished in HIV-1 wt virions compared with HIV-1 ΔVif virions.

Vif Expression is Associated with the Disappearance of Endogenous APOBEC3G Protein in HIV-1-Infected H9 T Cells To further elucidate the mechanism by which HIV-1 Vif prevents the incorporation of APOBEC3G into virions, intracellular levels of endogenous APOBEC3G in H9 cells were analyzed 2 days after infection with HIV-1 wt or HIV-1 ΔVif viruses. For these studies H9 cells were employed that displayed comparable levels of HIV-1 infection (76.4% versus 73.9%) as assessed by intracellular anti-p24-Gag immunostaining (FIG. 3A, top) and equivalent viability as assessed by forward and side light scattering properties (FIG. 3A, bottom).

Next, cellular lysates were prepared from uninfected H9 cells, or H9 cells equivalently infected with HIV-1 wt or HIV-1 ΔVif and analyzed expression of endogenous APOBEC3G protein by immunoblotting with the anti-APOBEC3G antibody (FIG. 3B). A marked reduction was observed in the expression of endogenous APOBEC3G protein in H9 cells infected with HIV-1 wt. Conversely, APOBEC3G expression was readily detected in HIV-1 ΔVif infected H9 cell cultures. This level was very similar to that found in uninfected H9 cells suggesting that HIV-1 infection does not induce APOBEC3G expression. In contrast, α-tubulin levels did not decline in the HIV-1 wt infected sample in comparison to uninfected or HIV-1 ΔVif infected samples (FIG. 3B). Vif was expressed in the HIV-1 wt infected sample, and similar levels of Nef were detected in the two virally infected samples (FIG. 3B). These findings demonstrate that infection of nonpermissive cells with HIV-1 expressing Vif leads to a marked loss of native APOBEC3G protein expression.

FIG. 3. Vif induces an almost complete disappearance of endogenous APOBEC3G in H9 cells infected with HIV-1-wt but not in cells infected with HIV-1 ΔVif (A). Infection of H9 cells. H9 cells were infected with VSV-G pseudotyped HIV-1-wt or HIV-1 ΔVif virus by spinoculation and analyzed by flow cytometry using intracellular Gag expression to monitor the extent of viral infection and by forward and side scattering of light (FSC/SSC) to identify live cells. Note that H9 cells infected with HIV-1 wt and HIV-1 ΔVif were comparably infected and displayed equivalent numbers of cells in the live cell gate. (B) Analysis of endogenous APOBEC3G expression in uninfected H9 cells or H9 cells infected with HIV-1 wt and HIV-1 ΔVif viruses. Cellular lysates from these cultures were immunoblotted with anti-C-terminal APOBEC3G antiserum and with anti-α-tubulin, anti-Vif or anti-Nef antibodies. Note the sharp decline in intracellular APOBEC3G levels in cells infected with HIV-1wt viruses.

APOBEC3G mRNA Levels and Integrity Do Not Change in the Presence of HIV-1 Vif.

Figure 4:
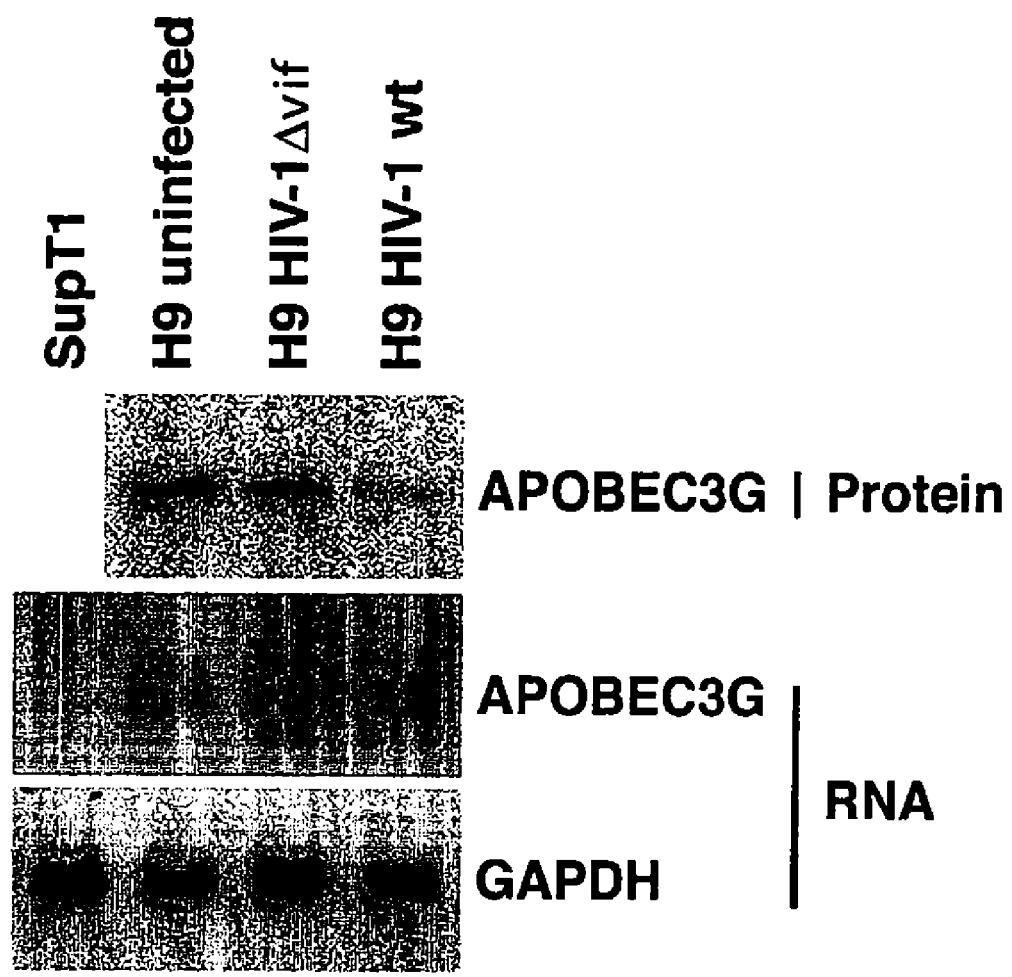
FIG. 4 depicts APOBEC3G mRNA levels in the presence of Vif.

To further dissect the mechanism underlying the apparent disappearance of APOBEC3G protein expression in HIV-1 wt infected H9 cells, the possibility that Vif alters the expression or integrity of APOBEC3G mRNA was considered. RNA and protein were simultaneously prepared from uninfected and infected H9 cells and levels of APOBEC3G mRNA and protein were assessed. As expected, APOBEC3G protein expression was decreased in the H9 cells infected with HIV-1 wt. However, there was no apparent difference in the level of expression of APOBEC3G mRNA among the three samples (FIG. 4). Equivalent RNA loading in these samples was confirmed by hybridization with a DNA probe specific for GAPDH (FIG. 4). These findings show that Vif does not impair APOBEC3G protein expression by interfering with the production or stability of APOBEC3G mRNA.

FIG. 4. Vif does not alter APOBEC3G mRNA expression or integrity. Total RNA was extracted from lysates of H9 cells that were either uninfected or infected with VSV-G pseudotyped HIV-1 or HIV-1 ΔVif viruses and then subjected to Northern blot analysis using a P-labeled APOBEC3G probe. Note that while APOBEC3G protein expression is decreased in H9 cells infected with HIV-1 wt, the level of APOBEC3G mRNA in these same cells is equivalent to that present in cells infected with HIV-1 ΔVif. Radiolabeled GAPDH probes were employed as a control for mRNA loading.

Vif Alone is Sufficient to Reduce Intracellular Levels of APOBEC3G

Figure 5A:
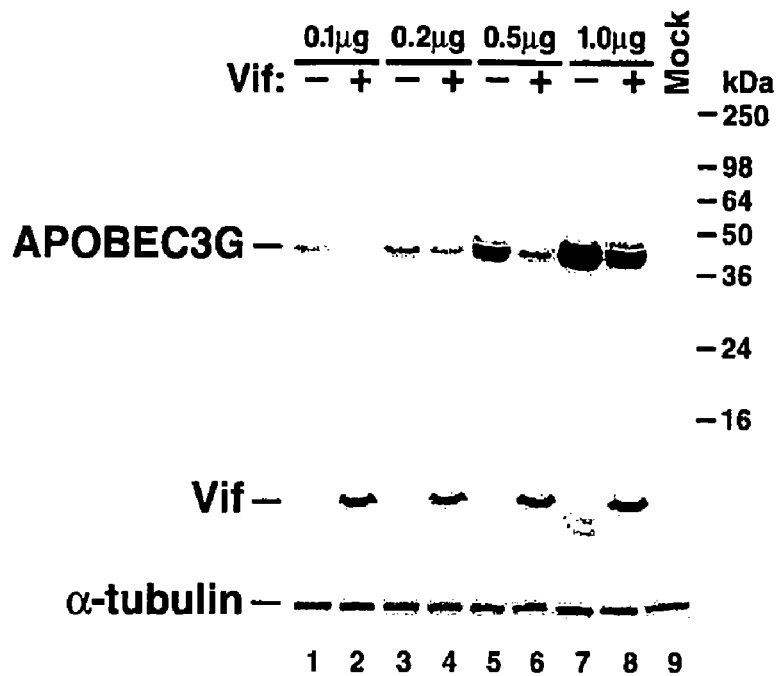
FIGS. 5A-5C depict intracellular depletion of APOBEC3G induced by Vif alone.

The question of whether Vif alone could recapitulate the decline in endogenous APOBEC3G levels observed when H9 cells were infected with virus containing the full complement of HIV-1 proteins was examined. For these studies, 293T cells were transiently transfected with increasing doses of untagged APOBEC3G expression plasmid (0.1-1.0 ug) in the presence of a fixed amount of Vif expression vector (FIG. 5A). The expression of Vif alone reduced the intracellular levels of APOBEC3G protein, although this effect was proportionately less at high APOBEC3G input levels. The levels of Vif expression were comparable in each of the cell lysates from cells transfected with Vif expression vector DNA; and the cellular lysates contained similar amounts of α-tubulin, indicating comparable loading. The Vif-induced decrease of APOBEC3G expression was also not caused by translocation of APOBEC3G into the nucleus since analysis of whole cell lysates revealed the same loss of APOBEC3G. These results demonstrate that Vif is able to act in the absence of other viral components to promote an intracellular decline in APOBEC3G protein expression.

FIG. 5. Intracellular depletion of APOBEC3G by Vif does not require the participation of other viral proteins and Vif physically interacts with APOBEC3G. (A) Expression of Vif in 293T cells is sufficient to promote a decline in intracellular APOBEC3G expression in the absence of other HIV-1 proteins. 293T cells were transfected with graded amounts of APOBEC3G expression vector DNA in the presence or absence of a constant amount of Vif expression vector. Cellular lysates from these cultures were immunoblotted with anti-APOBEC3G antiserum to assess intracellular levels of this protein. Note that Vif alone is sufficient to induce a decline in APOBEC3G expression over the range of APOBEC3G inputs although the effect is most pronounced at the lower levels of APOBEC3G expression. Blotting for α-tubulin expression confirmed loading of comparable amounts of these cellular lysates. (B) APOBEC3G interacts with GST-Vif. Lysates from 293T cells transfected with HA-APOBEC3G expression vector DNA and either GST or GST-Vif mammalian expression vectors were incubated with glutathione-sepharose beads. After washing, the beads were boiled in sample buffer and analyzed by SDS-PAGE followed by immunoblotting. Note that GST-Vif but not GST binds HA-APOBEC3G. (C) GST-Vif is biologically active. Immunoblotting analysis of lysates from 293T cells co-transfected with APOBEC3G-HA expression plasmid and either GST or GST-Vif expression vector. Note that expression of GST-Vif but not GST induced a decline in intracellular APOBEC3G levels.

Vif Physically Assembles with APOBEC3G

Figure 5B:
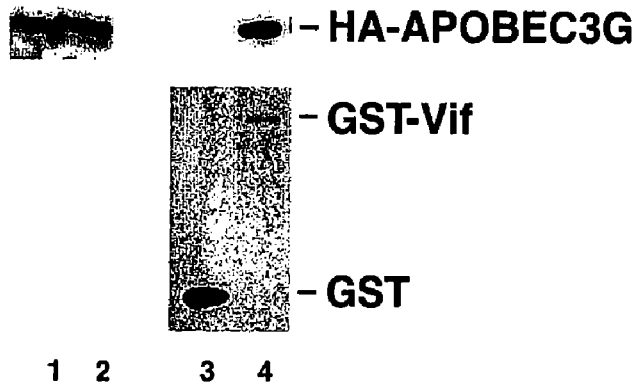
Figure 5C:
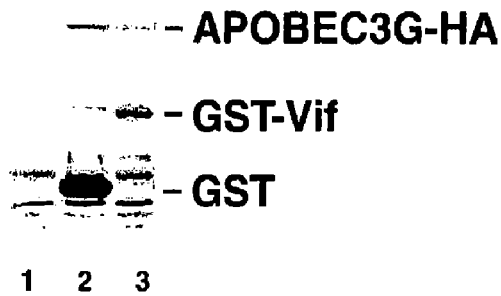

A potential physical interaction of HIV-1 Vif with APOBEC3G was evaluated by using a mammalian GST expression system. HA-APOBEC3G and GST-Vif or control GST expression plasmids were co-transfected into 293T cells (FIG. 5B). Cell lysates were prepared and incubated with glutathione sepharose beads. Subsequent immunoblotting analysis revealed that HA-APOBEC3G was precipitated by GST-Vif but not by GST alone (FIG. 5B). We also confirmed that GST-Vif retained biological activity by monitoring APOBEC3G-HA levels in the presence and absence of GST-Vif. APOBEC3G-HA levels were reduced in the presence of GST-Vif when compared to GST alone (FIG. 5C). These findings indicate that Vif either directly or indirectly assembles with the APOBEC3G protein in living cells and that the chimeric GST-Vif protein retains the ability to impair APOBEC3G expression.

APOBEC3G is Present in a High-Molecular Weight Ribonucleoprotein Complex and Vif Co-Fractionates with this Complex.

Figure 6A:
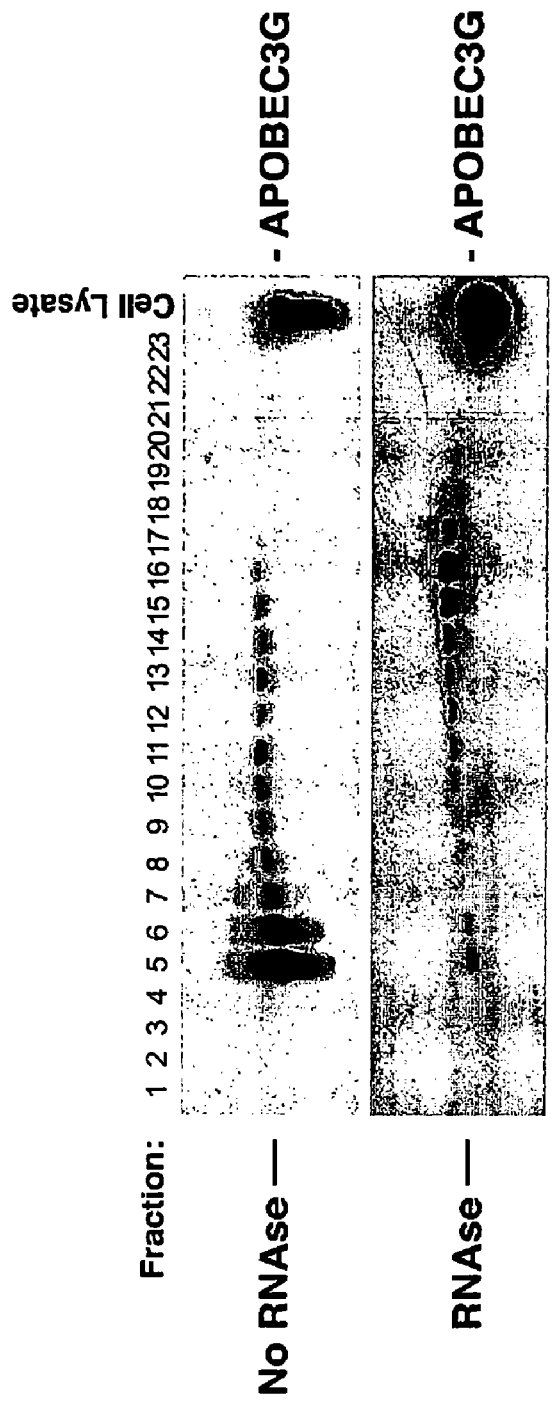
FIGS. 6A and 6B depict Vif association with APOBEC3G/RNA high molecular weight complexes.
Figure 6B:
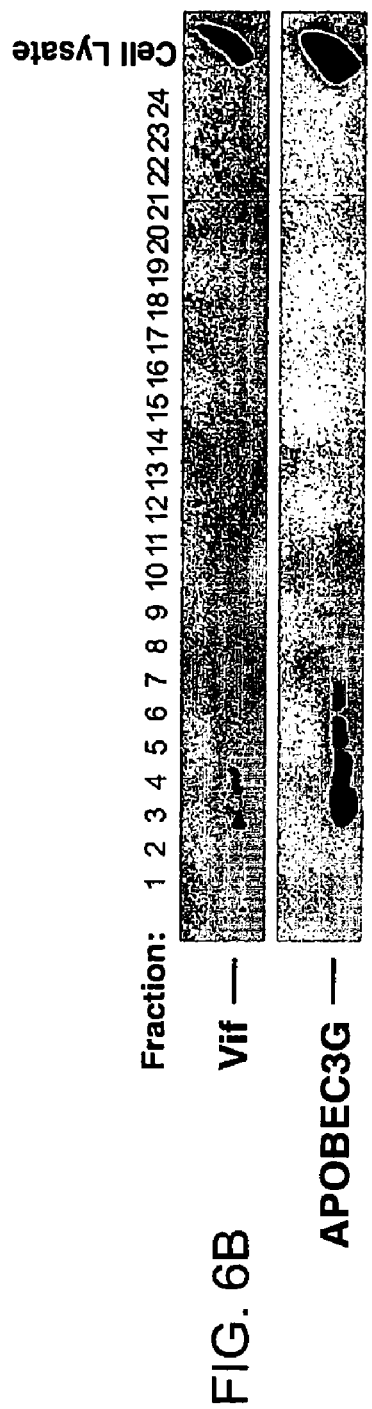

To further discern the mechanism employed by Vif, we investigated whether APOBEC3G resides in a larger complex and, if so, whether Vif could associate with this complex. First, using size-exclusion fast performance liquid chromatography (FPLC) of lysates from transfected 293T cells, it was found that APOBEC3G-HA is present in a high molecular weight complex (>700 kD) (FIG. 6A). Interestingly, pretreating the cellular lysates with RNAse promoted disruption of this high molecular weight APOBEC3G complex (FIG. 6A). Furthermore, size-exclusion FPLC analysis of infected H9 cell lysates revealed that a portion of Vif expressed in these cells co-fractionates with the endogenous high molecular weight APOBEC3G complex. These findings indicate that APOBEC3G assembles into a high molecular weight complex that includes cellular RNAs and that the RNA maintains the integrity of the complex. Furthermore, a portion of Vif present in HIV-1 wt infected H9 cells co-fractionates with the high molecular weight APOBEC3G complex (FIG. 6B), which is consistent with our prior finding indicating that Vif binds directly or indirectly to APOBEC3G (FIG. 5B).

FIG. 6. APOBEC3G assembles in an RNAse-sensitive high molecular weight complex and a portion of Vif co-fractionates with this APOBEC3G complex in infected H9 cells. (A) APOBEC3G assembles in a high-molecular weight RNAse-sensitive complex. Lysates from 293T cells transfected with APOBEC3G-HA were either treated with diluent control or 0.01 mg/ml RNAse on ice for 30 minutes. The lysates were then applied to a Superose 6 column and subjected to FPLC size-exclusion fractionation followed by SDS-PAGE and immunoblotting with anti-HA antibodies. Note that APOBEC3G-HA predominantly resides in a >700 kD complex and that RNAse treatment results in a shift of most of the APOBEC3G to a lower molecular weight complex. (B) Vif and APOBEC3G co-fractionate in infected H9 cells. H9 cells were infected with VSV-G pseudotyped HIV-1 wt virus followed by the preparation of cellular lysates and analysis of lysate proteins on a Superose 12 FPLC column. Fractions were collected and analyzed by immunoblotting with anti-APOBEC3G or anti-Vif antibodies. Note that a portion of Vif co-fractionates with native APOBEC3G in a >700 kD complex.

Vif Induces Proteolytic Degradation of APOBEC3G

It was next determined whether Vif induces APOBEC3G degradation or, alternatively, whether it simply induces proteolytic clipping of APOBEC3G leading to loss of immunoreactivity with the rabbit anti-APOBEC3G antibody. Since this antibody reacts specifically with the C-terminus of APOBEC3G, whether a similar loss of APOBEC3G immunoreactivity occurred when an antibody directed to the N-terminus was employed was examined. For these studies, graded doses of either HA-APOBEC3G or APOBEC3G-HA expression vector DNA together with Vif expression plasmid DNA were co-transfected into 293T cells and tested the cellular lysates for APOBEC3G expression using an anti-HA antibody. Both N- and C-terminally tagged versions of APOBEC3G were expressed at reduced levels in the presence of Vif (FIGS. 7 A&B). These findings support the conclusion that Vif induces degradation of APOBEC3G or extensive proteolysis of APOBEC3G involving both the N and C-termini of the protein.

APOBEC3G is Polyubiquitylated and Vif Promotes Degradation of $(Ub)_n$-APOBEC3G

Figure 7C:
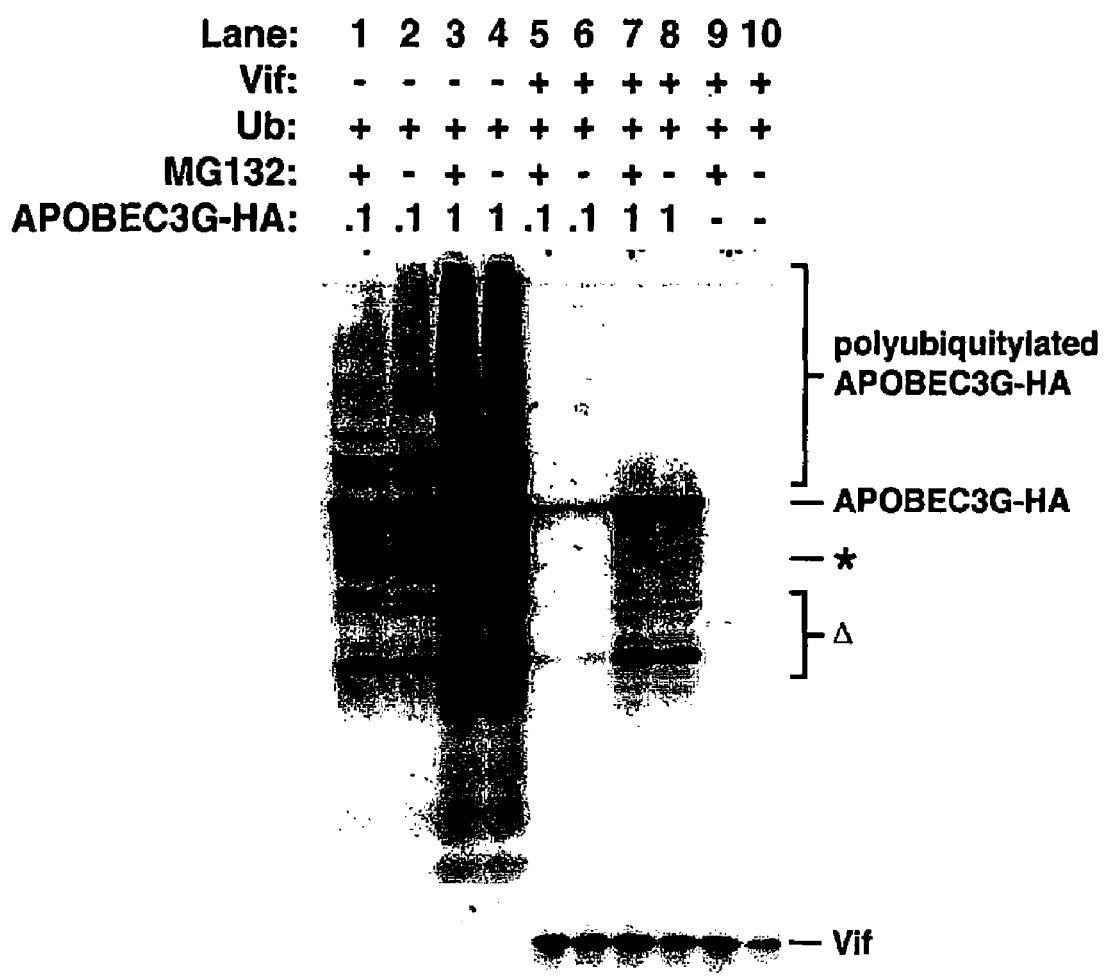

To obtain further insight into the mechanism of Vif-induced degradation of APOBEC3G, it was investigated whether APOBEC3G is modified by ubiquitylation. APOBEC3G and His-ubiquitin expression vectors (Treier et al., 1994) were cotransfected into 293T cells in the presence or absence of Vif expression vector. After 48 hours in culture, cellular lysates were prepared. Subsequent immunoblotting of these proteins with anti-HA antibodies revealed a continuum of polyubiquitylated forms of APOBEC3G-HA (FIG. 7C, lanes 2 and 4). Immunoblotting of lysates prepared in the absence of APOBEC3G-HA confirmed that anti-HA antibodies selectively reacted with modified forms of APOBEC3G (FIG. 7C, lane 10). Coexpression of Vif was associated with a complete loss of these polyubiquitylated APOBEC3G species as well as diminished expression of unmodified APOBEC3G (FIG. 7C, lanes 6 and 8). To investigate whether the 26S proteasome mediated Vif-induced degradation of these polyubiquitylated APOBEC3G protein species, parallel experiments were performed in the presence of the proteasome inhibitor, MG132. This proteasome inhibitor did not block the Vif-dependent disappearance of polyubiquitylated APOBEC3G or increase levels of the unmodified protein (FIG. 7C, lanes 5 and 7). However, MG132 promoted increased accumulation of many polyubiquitylated proteins within these cells, indicating that the inhibitor was biologically active. These findings suggest that Vif-induced degradation of polyubiquitylated APOBEC3G occurs through a mechanism that is not dependent on the function of the 26S proteasome. However, it was also observed in multiple experiments that one of the many APOBEC3G degradation products appearing in Vif-expressing cells increased after the addition of MG132 (FIG. 7C, compare lanes 7 and 8). These findings raise the possibility that Vif action may involve multiple pathways including the targeting of select proteolytic fragments of APOBEC3G for degradation by the 26S proteasome.

FIG. 7. HIV-1 Vif induces degradation of APOBEC3G, and polyubiquitylated forms of APOBEC3G form a major target for Vif induced degradation. (A and B) Vif promotes degradation or extensive proteolysis of APOBEC3G as reflected by the loss of both N- and C-terminal immunoreactive epitopes. Graded amounts of expression vector DNA encoding HA-APOBEC3G or APOBEC3G-HA were co-transfected with and without Vif expression vector DNA into 293T cells.

Cellular lysates prepared from these cultures were analyzed by immunoblotting with anti-HA antibodies. Immunoblotting for α-tubulin expression confirmed comparable loading of these cellular lysates. Note that Vif expression induces a loss of anti-HA immunoreactivity regardless of whether the HA epitope is positioned at the N- or C-terminus of APOBEC3G. (C) APOBEC3G is polyubiquitylated and Vif induces degradation of $(Ub)_n$-APOBEC3G apparently by a proteasome-independent mechanism. 293T cells were cotransfected with APOBEC3G-HA and his-ubiquitin expression vectors in the presence or absence of Vif expression vector. 48 hours later, cellular lysates were prepared. As indicated, select cultures were supplemented with the proteasome inhibitor, MG132, for the final 6 hours of culture. Lysates were analyzed by immunoblotting with anti-HA antibodies. Note that coexpression of Vif resulted in marked loss of polyubiquitylated APOBEC3G-HA proteins and that the disappearance of these modified forms of APOBEC3G-HA was not blocked by addition of the MG132 proteasome inhibitor to the cell cultures. In addition to the polyubiquitylated forms of APOBEC3G-HA, degradation products of APOBEC3G-HA were apparent both in the presence and absence of Vif expression. One of these multiple degradation products of APOBEC3G-HA present in Vif expressing cells increased in quantity in the presence of MG132 (*) suggesting that the degradation likely involved an action of the proteasome.

Vif Induced Depletion of APOBEC3G Involves Disappearance of the Entire Protein

It was investigated whether the apparent loss of APOBEC3G in Vif expressing cells could be explained by proteolytic clipping of the C-terminus, which would result in a loss of the epitope used for immunodetection. When 293T cells were co-transfected with graded doses of HA-APOBEC3G or APOBEC3G-HA expression vector DNA in the presence or absence of Vif expression plasmid DNA, both the N- and C-terminally tagged versions of the APOBEC3G enzyme were diminished in the presence of Vif. These findings indicate that Vif targets the entire APOBEC3G protein for elimination rather than inducing proteolysis only at the C-terminus.

Vif Physically Assembles with APOBEC3G

To evaluate whether HIV-1 Vif physically interacts with APOBEC3G, 293T cells were contransfected with HA-APOBEC3G and GST-Vif or control GST expression plasmid DNA. Cellular lysates were prepared and incubated with glutathione-Sepharose beads. Immunoblotting of proteins bound to these beads demonstrated recovery of HA-APOBEC3G by GST-Vif but not by GST. To assess whether the GST-Vif protein retained biological activity, HA-APOBEC3G levels were monitored in the presence and absence of GST-Vif and observed lower levels of this enzyme in the presence of GST-Vif (FIG. 8D). These findings indicate that Vif is able to assemble with the APOBEC3G protein in living cells and further that the chimeric GST-Vif protein retains the ability to impair intracellular APOBEC3G expression.

Vif Shortens the In Vivo Half-Life of APOBEC3G.

To investigate whether Vif depletes the intracellular levels of APOBEC3G by accelerating its degradation, [$^{35}$S]-methionine/cysteine pulse-chase radiolabeling studies were performed in HEK 293 cells co-transfected with APOBEC3G-HA and HIV-1 Vif or control expression vector DNA. Thirty-six hours after transfection, the cells were incubated in methionine and cysteine-deficient medium for 60 minutes followed by pulse labeling with $^{35}$S-methionine/cysteine for 30 minutes at 37° C. Subsequently, the cultures were chased for up to 12 hours at 37° C. in media containing excess unlabeled methionine and cysteine. APOBEC3G-HA was then immunoprecipitated from lysates of cells harvested at different intervals (FIG. 8A). In the absence of Vif, the radiolabeled APOBEC3G protein decayed with a T1/2 of approximately 10 hrs. However, in the presence of Vif, the radiolabeled APOBEC3G disappeared more rapidly, displaying a T1/2 of approximately 1.9 hrs (FIG. 8A). These findings demonstrate that Vif shortens the half-life of APOBEC3G.

Proteasome Inhibitors Partially Block Vif-Mediated Depletion of APOBEC3G

To investigate whether the 26S proteasome might mediate the Vif-induced degradation of APOBEC3G, H9 cells were infected with HIV-1 wt or were mock-infected. Forty-four hours after infection, the cells were treated for 16 hours with either DMSO (0.1%) or 0.25 µM epoxomicin, which specifically inhibits three proteolytic activities in the proteasome. Whole cell lysates were subsequently prepared by boiling the cells in Laemmli lysis buffer, followed by protein separation by SDS-PAGE and immunoblotting. As expected, APOBEC3G levels were much lower in the infected sample when compared to the uninfected sample (FIG. 8B, lanes 1 and 3). However, APOBEC3G levels were elevated in infected cells treated with epoxomicin when compared to DMSO-treated cells (FIG. 8B, lanes 1 and 2), while epoxomicin did not appear to cause a similar increase in the level of APOBEC3G in the uninfected cultures (FIG. 8B, lanes 3 and 4). Interestingly, epoxomicin also caused an increase in Vif levels.

Figure 8C:

To confirm this finding in a different system, a similar experiment was performed using 293T cells transiently transfected with an APOBEC3G-HA expression vector and either a Vif expression vector or a control vector. Twenty-four hours after transfection the cells were treated with a panel of different proteasome inhibitors for a 15-hour period. It was observed that the broadly acting proteasome inhibitors MG132 (12.5 µM) and ALLN (25 µM) as well as the more specific proteasome inhibitor clasto-Lactacystin-β-Lactone (110 µM, 20 µM) enhanced the levels of APOBEC3G-HA in the presence of Vif when compared to the diluent control sample (0.1% DMSO) (FIG. 8C, lanes 7 through 12). In contrast, Calpain Inhibitor III (50 µM), which inhibits a separate proteolytic pathway (FIG. 8C, lane 12), did not cause an increase in APOBEC3G levels. Taken together, our results indicate that Vif's effect on APOBEC3G is at least partially mediated by the proteasome.

FIG. 8A-C. Vif shortens the half-life of APOBEC3G, and proteasome inhibitors partially block the intracellular depletion of APOBEC3G-HA. (A) Pulse-Chase Radiolabeling. HEK 293 cells transiently transfected with APOBEC3G-HA and Vif or control vector DNA were pulse-labeled for 30 min. The initial pulse-labeled (t=0) samples were harvested, and the remaining samples were incubated with chase media for the indicated time points. After immunoprecipitation with anti-HA antibody, the samples were analyzed by SDS-PAGE and the gels were subjected to autoradiography. The relative intensity of the bands were quantified and the Vif (+) and Vif (−) samples were normalized to 1 and graphed (FIG. 8, right side). The $T_{1/2}$ of APOBEC3G was 1.9 hours in the presence of Vif and 10 hours in the absence of Vif. (B) Proteasome inhibitor studies using infected H9 cells. Mock or HIV-1 wt-infected H9 cells were treated with the broadly active proteasome inhibitor epoxomicin (0.25 µM) or DMSO (0.1%) 44 hours after infection. Sixteen hours following treatment, the cells were harvested; and whole cell lysates were prepared by boiling the cells in Laemmli lysis buffer. Note that Epoxomicin caused an increase in endogenous APOBEC3G levels in the infected sample (compare lane 2 with lane 1). (C) Proteasome inhibitor studies using transiently-transfected 293T cells. Twenty-four hours following transfection of 293T cells with 0.1 µg APOBEC3G and 2 µg Vif or control vector DNA, the cells were treated with the indicated concentration of inhibitor for 15 hours. APOBEC3G-HA levels were elevated in the presence of the proteasome inhibitors MG132, ALLN, and clasto-lactacystin-β-lactone (lanes 8-11), but not in the presence of calpain inhibitor III (lane 12).

Vif Also Impairs Translation of APOBEC3G mRNA

Figure 9A:
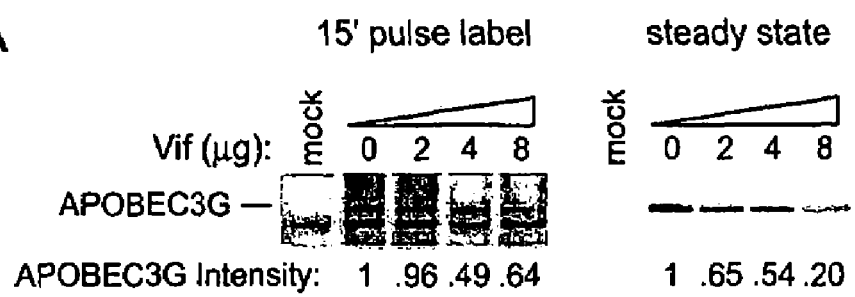
FIGS. 9A-B depict the effect of Vif on APOBEC3G-HA mRNA.

In the course of the in vivo pulse-chase radiolabeling experiments, it was observed that 15-40% less radiolabeled APOBEC3G was recovered after the pulse labeling phase in cells expressing Vif as compared to cells not expressing Vif. These results raised the possibility that Vif might inhibit APOBEC3G expression by impairing the translation of APOBEC3G mRNA. To further investigate this possibility, shorter pulse-labeling experiments (15 minutes) were performed in the presence of increasing amounts of Vif (0-8 µg) (FIG. 9A, left side). These studies revealed that Vif impaired $^{35}$S-methionine/cysteine radiolabeling of APOBEC3G-HA in vivo in a dose-related manner, consistently causing a 30-50% decline in APOBEC3G translation during the pulse-labeling period. Immunoblotting analysis of the same samples revealed an 80% decline in the steady-state levels of APOBEC3G-HA (FIG. 9A, right side). Since a 30-50% decline in translation does not fully explain the 80% decline in the steady-state levels of APOBEC3G-HA, Vif must function both by partially blocking the synthesis of the APOBEC3G protein and by inducing APOBEC3G degradation after translation.

Figure 9B:
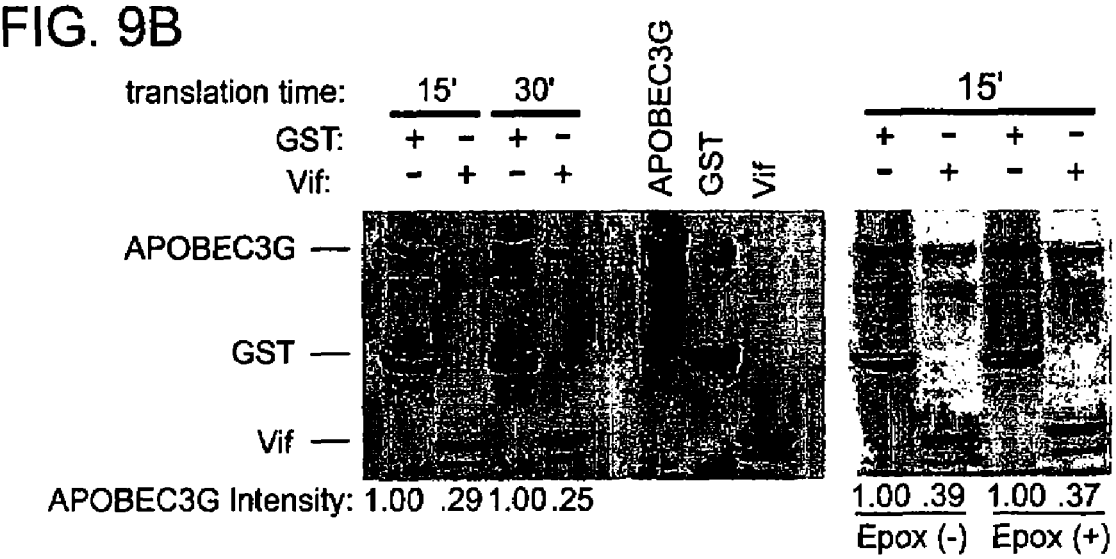
Figure 10:
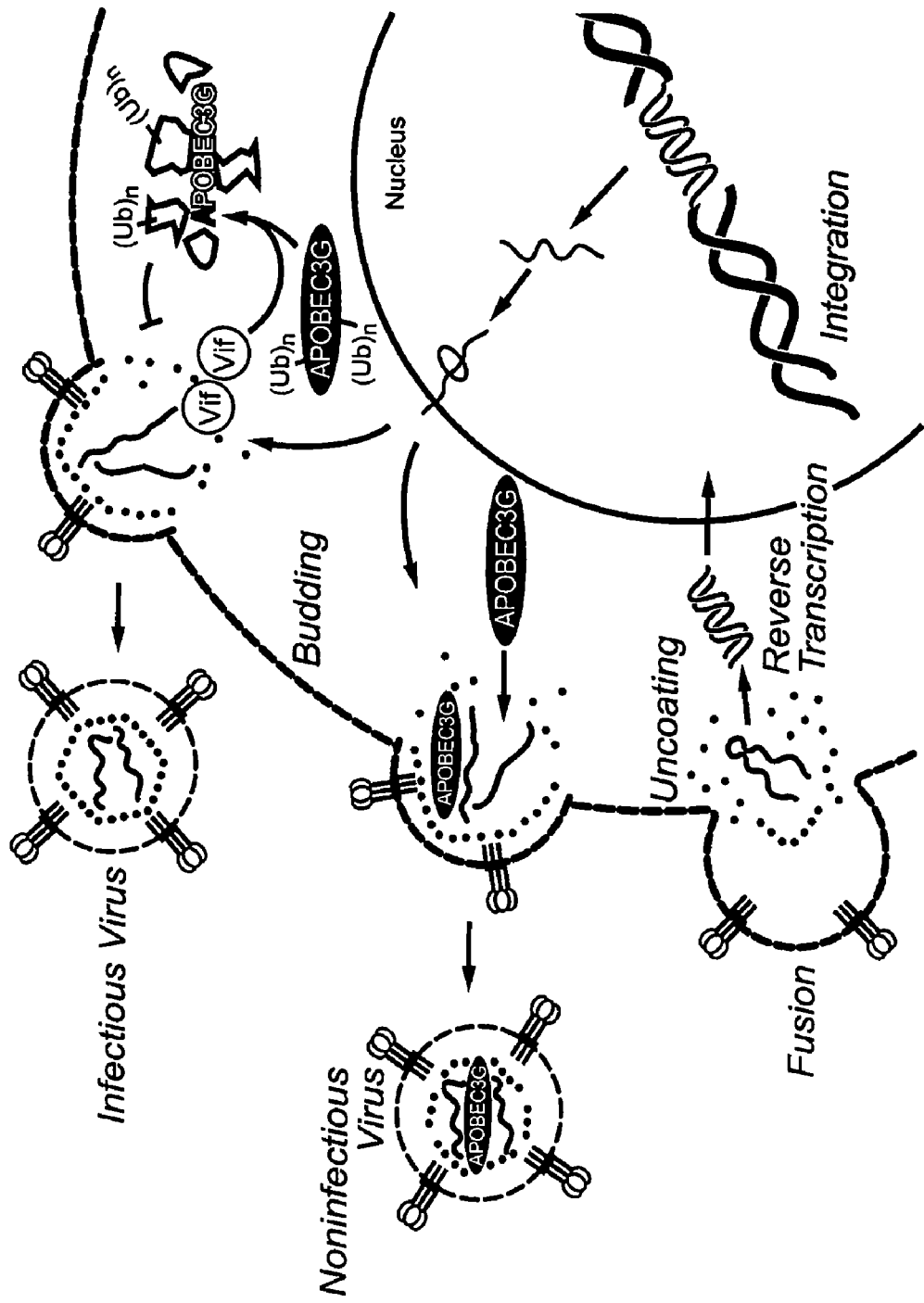
FIG. 10 is a schematic representation depicting how Vif targets ubiquitylated APOBEC3G for degradation in a virus-producing cell, thus blocking virion incorporation of APOBEC3G; and the potent mutagenic action of APOBEC3G's cytidine deaminase activity during viral DNA synthesis.

To further examine the effects of Vif on APOBEC3G mRNA translation, an in vitro coupled transcription/translation system was employed. Rabbit reticulocyte lysates were programmed with APOBEC3G mRNA in the presence of pre-translated Vif or GST control protein (FIG. 9B). In this in vitro system, Vif impaired APOBEC3G translation by approximately 70-75%. These findings indicate that Vif partially blocks the in vitro translation of APOBEC3G mRNA.

Together, these results demonstrate that Vif depletes intracellular APOBEC3G in a bimodal manner by inhibiting translation of APOBEC3G mRNA and by accelerating proteasome-mediated degradation of the APOBEC3G enzyme. In combination, these two mechanisms effectively eliminate the APOBEC3G enzyme in infected T cells.

FIGS. 9A and 9B. Vif impairs the translation of APOBEC3G-HA mRNA. (A) In vivo pulse label studies. HEK 293 cells transiently transfected with 1 µg of APOBEC3G-HA expression vector DNA and 0 to 8 µg Vif expression vector DNA were pulsed with radiolabeled methionine and cysteine for 15 min and then immediately harvested. After immunoprecipitation with anti-HA antibody, the samples were either (1) subjected to SDS-PAGE and analyzed by autoradiography (left panel) or (2) subjected to SDS-PAGE and analyzed by immunoblotting (right panel). Higher concentrations of Vif caused a significant (36%-50%) impairment in the in vivo translation of APOBEC3G-HA (left panel). Vif caused an even greater (80%) reduction in the steady-state levels of APOBEC3G-HA (right panel). (B) In vitro Transcription/Translation Studies. Vif or control GST protein was initially transcribed and translated for 90 min using the Promega TNT T7-coupled Reticulocyte Lysate system according to the manufacturer's instructions. The pre-synthesized Vif or GST was then added to a new transcription/translation mix programmed with APOBEC3G DNA on ice. The reactions were then transferred to a 30° C. water bath and allowed to proceed for 15 or 30 min. The proteins were then separated by SDS-PAGE, and the gel was analyzed by autoradiography. Note that Vif produced a ~70-75% impairment in the in vitro synthesis of APOBEC3G.

Example 2

Characterization of High- and Low-Molecular Weight APOBEC3G Complexes

Human peripheral blood lymphocytes (PBLs) were isolated from blood and then incubated with anti-CD3 antibody (α-CD3), anti-CD28 antibody (α-CD28), IL-9, IL-12, IL-13, IL-15, or IFN-γ for 48 hours. Cells were lysed, the lysates clarified, and the protein concentration of the lysates was quantitated. Equal amounts of proteins in the lysates were separated by SDS-PAGE. After separation of the proteins by SDS-PAGE, the proteins were transferred to a membrane, and antibody to APOBEC3G was used to detect APOBEC3G protein on the membrane. The results are depicted in FIGS. 1-13.

Figure 11:
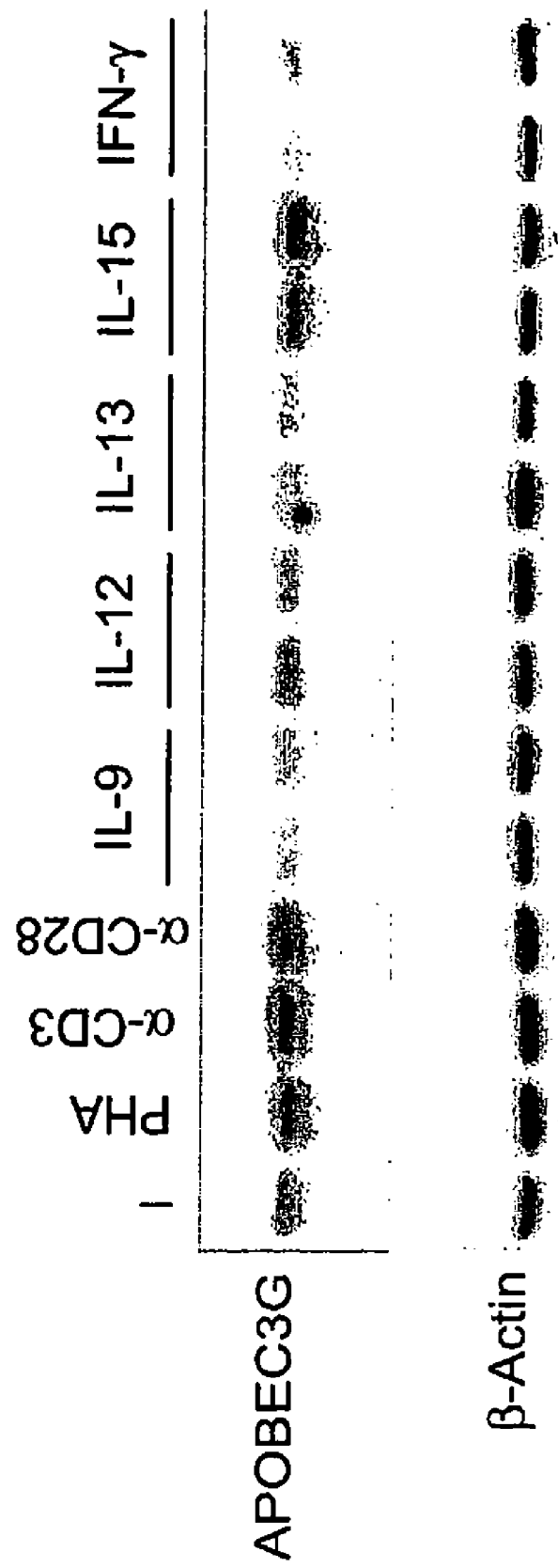
FIG. 11 depicts the effect of phytohemagglutinin (PHA), anti-CD3 antibody, anti-CD28 antibody, and IL-15 on the level of APOBEC3G in peripheral blood lymphocytes (PBL).

FIG. 11 depicts the effect of PHA, anti-CD3 antibody, anti-CD28 antibody, and IL-15 on the level of APOBEC3G in peripheral blood lymphocytes. PBLs treated with PHA, anti-CD3 antibody, anti-CD28 antibody, or IL15 display increased expression of the APOBECG enzyme. Western blot of cell lysates deriving from stimulated and unstimulated peripheral blood lymphocytes. PBLs were isolated from blood and then incubated with the indicated stimulant for 48 hours. Following separation of the proteins by SDS-PAGE, antibody to APOBEC3G was used to detect APOBEC3G protein. As a loading control, anti-β-actin was used to detect β-actin.

Figure 12:
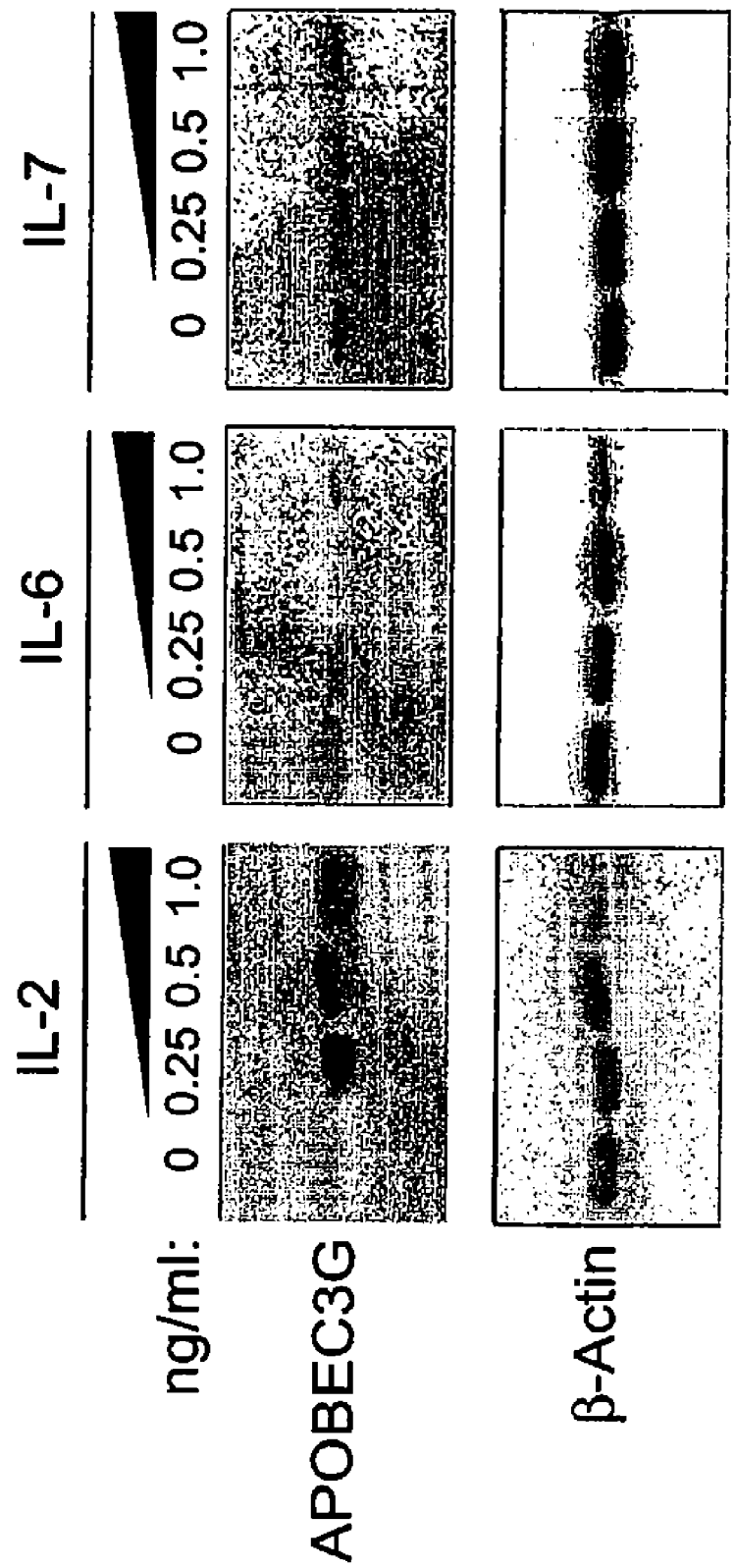
FIG. 12 depicts the effect of IL-2 on APOBEC3G levels in PBL.

FIG. 12 depicts the effect of IL-2 on APOBEC3G levels in PBL. Treatment with IL-2 results in upregulation of the APOBEC3G enzyme in peripheral blood lymphocytes. PBLs were treated with the indicated cytokine and then analyzed as in FIG. 11.

Figure 13:
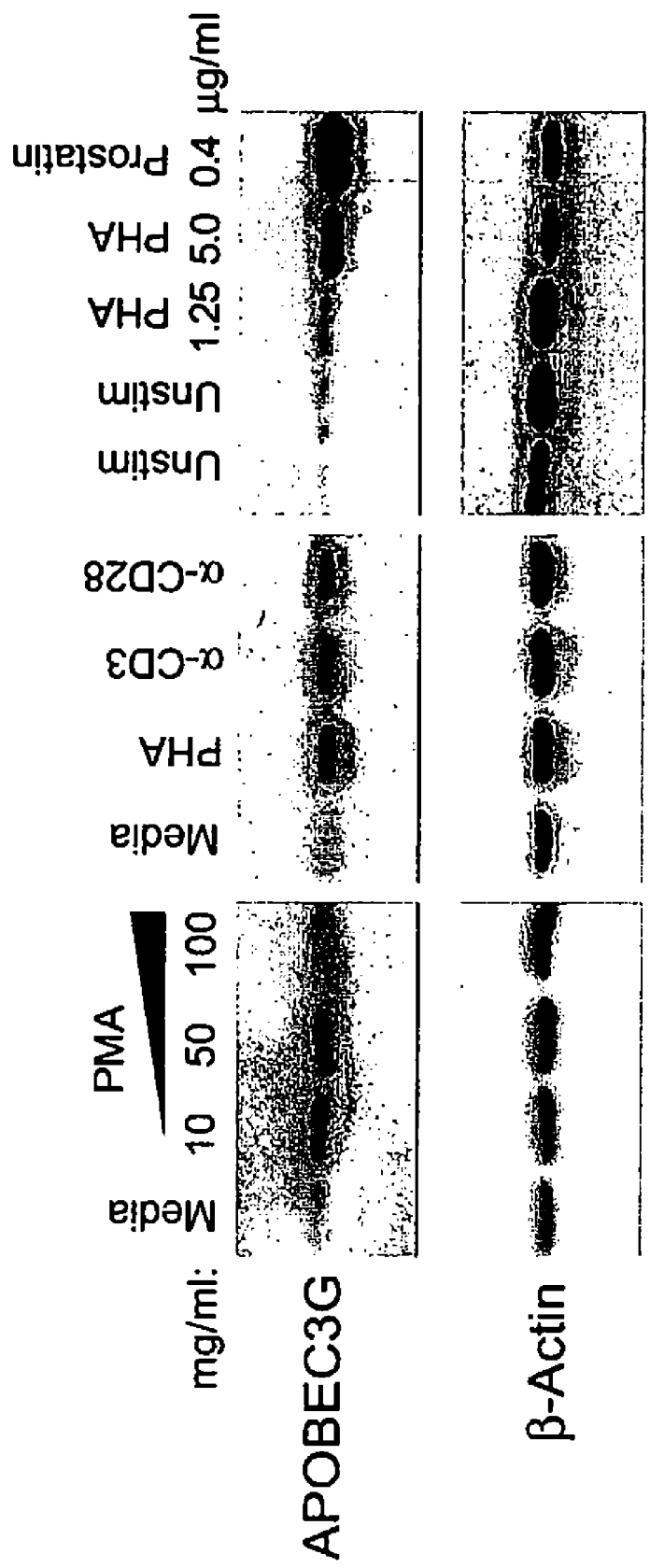
FIG. 13 depicts the effect of phorbol-12-myristate-13-acetate (PMA), PHA, anti-CD3 antibody, anti-CD28 antibody, and prostratin on the level of APOBEC3G in PBL.

FIG. 13 depicts the effect of PMA, PHA, anti-CD3 antibody, anti-CD28 antibody, and prostratin on the level of APOBEC3G in PBL. PMA, PHA, anti-CD3, anti-CD28, and prostratin all cause APOBEC3G to be upregulated in PBLs. PBLs were treated with the indicated mitogen or antibody and then analyzed as in FIGS. 11 and 12.

The assembly of APOBEC3G into low molecular weight or high molecular weight complexes was analyzed in various cells. The enzymatic activity of low molecular weight (LMW) APOBEC3G complexes and high molecular weigh (HMW) APOBEC3G complexes was analyzed.

H9 cells and 293T cells transiently transfected with HA-APOBEC3G DNA were cultured in standard conditions prior to use. CD4$^+$ T cells were isolated from fresh human peripheral blood lymphocytes (PBLs) by MACST microbeads (Miltenyi Biotec, Inc.) sorting and were maintained in complete RPMI media (10% FBS). A portion of the CD4$^+$ T cells was activated with phytohemagglutinin (PHA) (5 µg/ml) for 36 hours and then IL-2 (5 µg/L) for another 24 hours prior to use. Monocytes were isolated from buffy-coat peripheral blood mononuclear cells (PBMC). Immature dendritic cells were obtained by incubating monocytes in complete RPMI medium supplemented with GM-CSF (50 ng/mL) and IL-4 (25 ng/mL) for 6 days. Mature dendritic cells were derived from immature dendritic cells treated with TNF-alpha (5 ng/mL) and Poly IC (25 µg/mL) for 24 hours. Clarified lysates were made from these cells. Total protein in the clarified lysates was quantified and subjected to FPLC analysis with or without prior RNase treatment. Each FPLC fraction was subjected to SDS-PAGE and immunoblotting analysis. HA-APOBEC3G in the high and low molecular weight fractions was immunoprecipitated and subjected to the in vitro cytidine deaminase assay.

Figure 14:
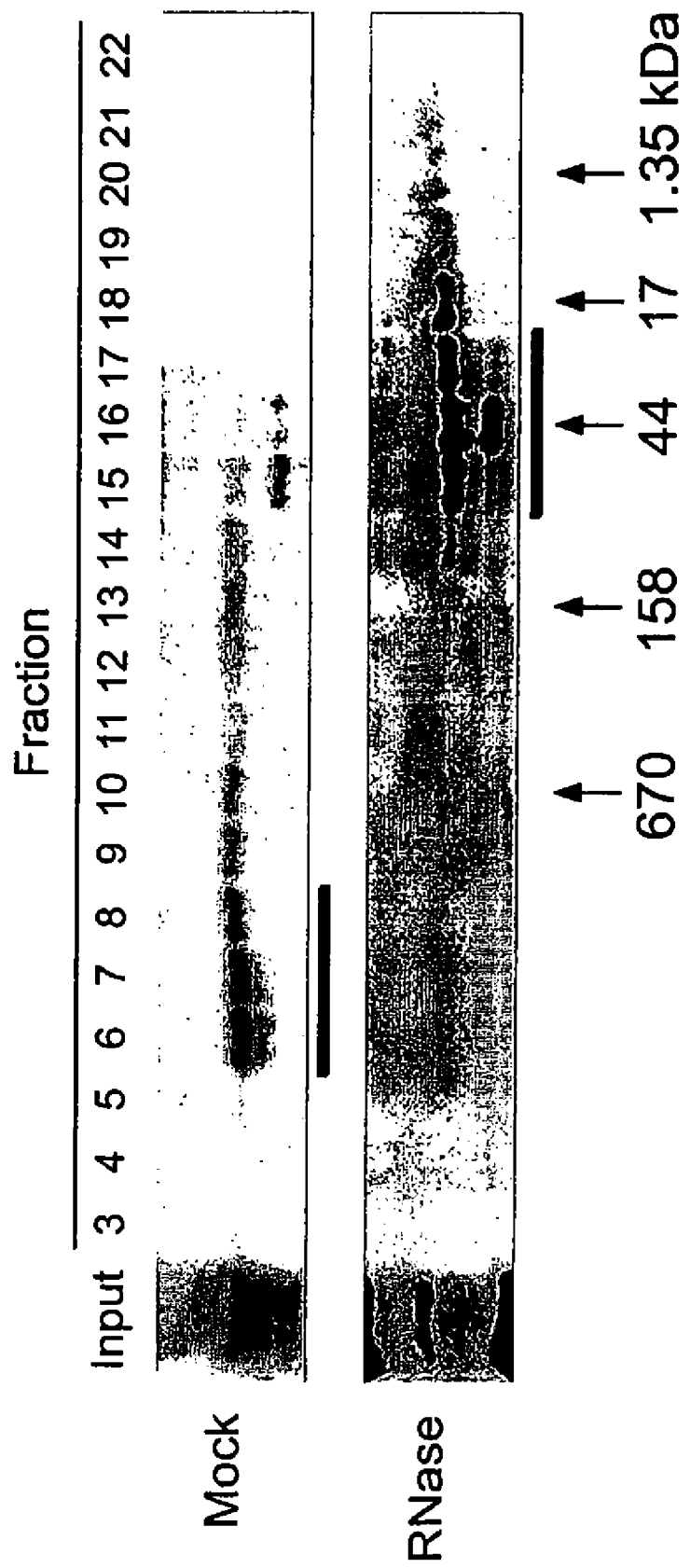
FIG. 14 depicts size-exclusion FPLC analysis of endogenous APOBEC3G. Endogenous APOBEC3G is assembled into a high molecular weight, RNase-sensitive complex in nonpermissive H9 cells.

FIG. 14 depicts results indicating that endogenous APOBEC3G is assembled into a HMW, RNase-sensitive complex in non-permissive H9 cells.

Figure 15:
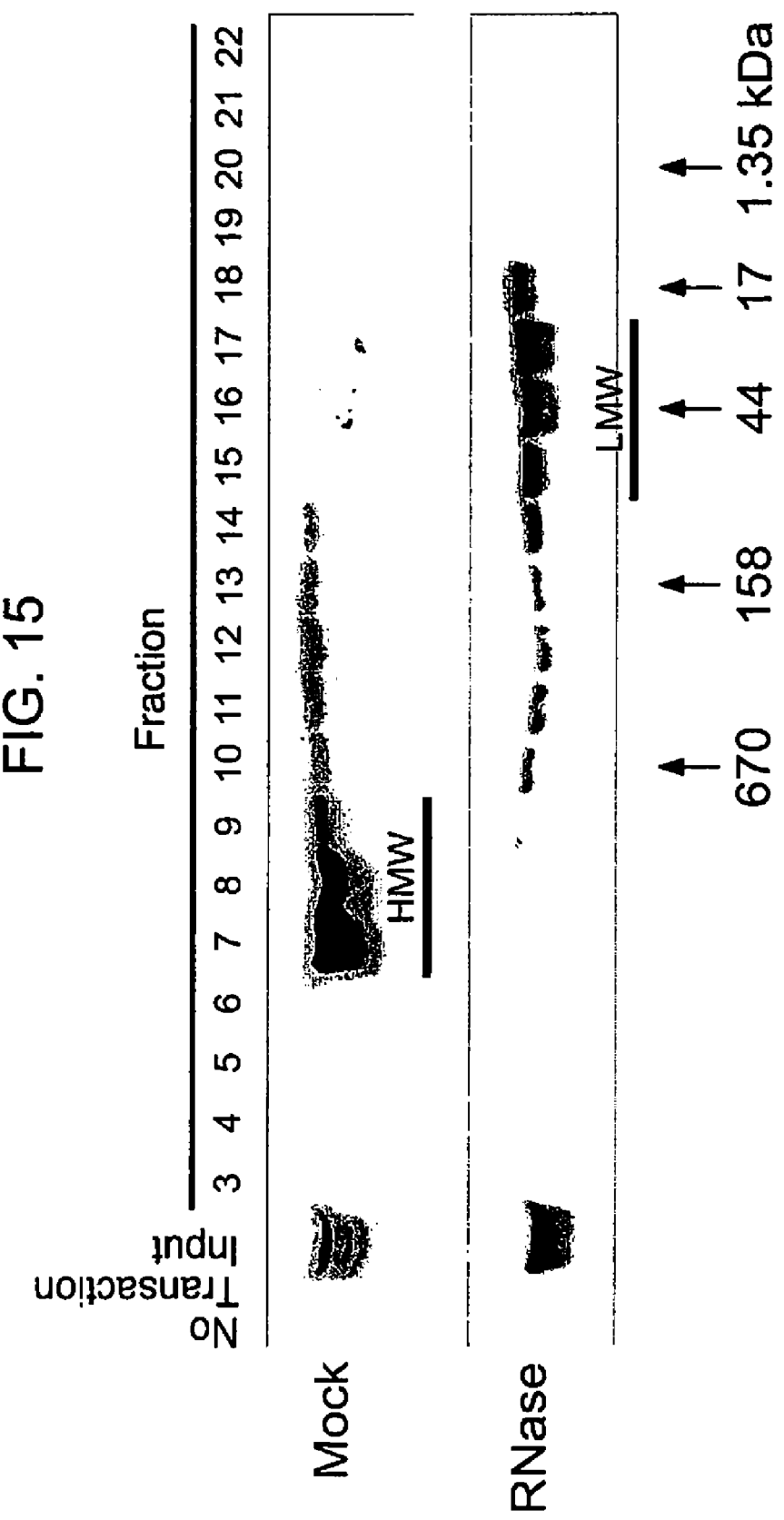
FIG. 15 depicts results showing that transfection of HA-APOBEC3G DNA into permissive cells leads to HMW APOBEC3G complex formation.

FIG. 15 depicts results showing that transfection of HA-APOBEC3G DNA into permissive cells leads to HMW APOBEC3G complex formation. This HMW fraction is RNase-sensitive as a LMW APOBEC3G complex results from RNase treatment of the HMW fraction.

Figure 16:
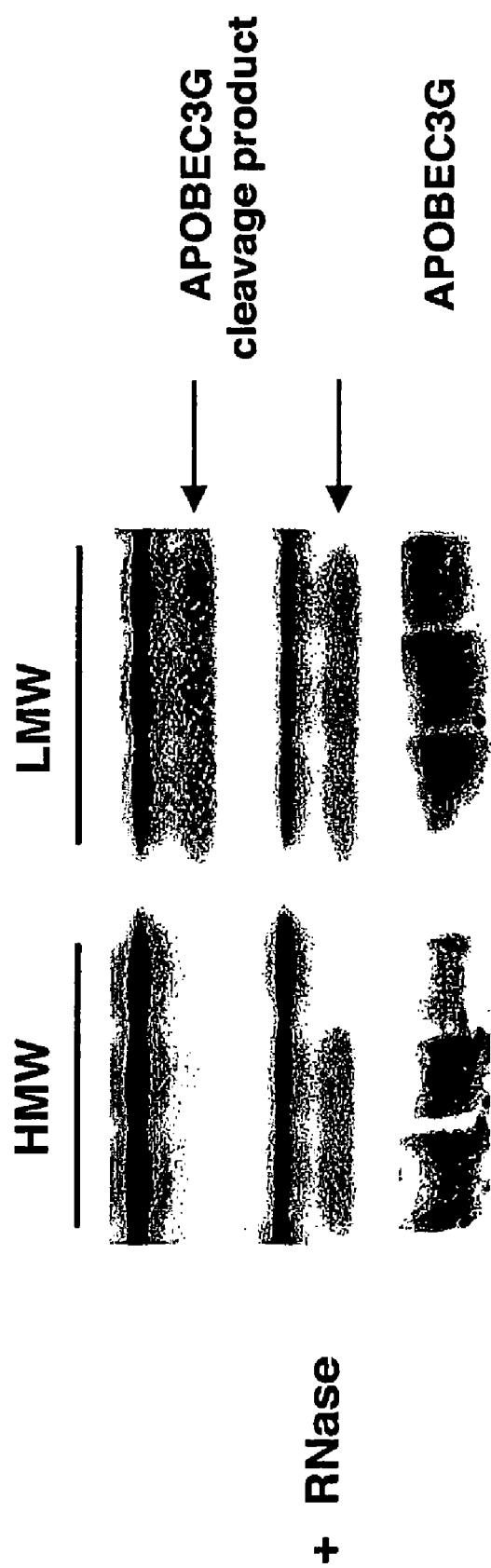
FIG. 16 depicts results showing that the low molecular weight, but not the high molecular weight, APOBEC3G complex exhibits cytidine deaminase activity.

FIG. 16 depicts results indicating that the LMW APOBEC3G complex, but not the HMW APOBEC3G complex, displays cytidine deaminase activity. Thus, APOBEC3G is recruited into a HMW ribonucleoprotein complex that lacks cytidine deaminase activity. Treatment of the HMW APOBEC3G complex with RNase produces a LMW APOBEC3G complex that exhibits high cytidine deaminase activity.

Figure 17:
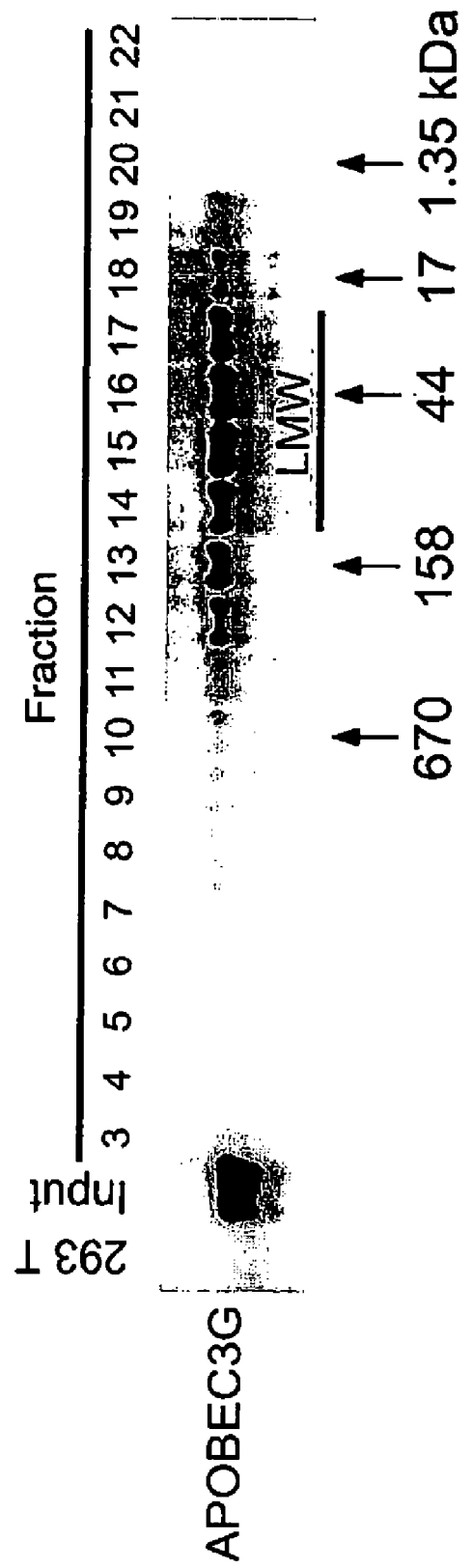
FIG. 17 depicts results showing that APOBEC3G in resting PBL is present in a LMW complex.

FIG. 17 depicts results showing that APOBEC3G in resting PBL is present in a LMW complex.

Figure 18:
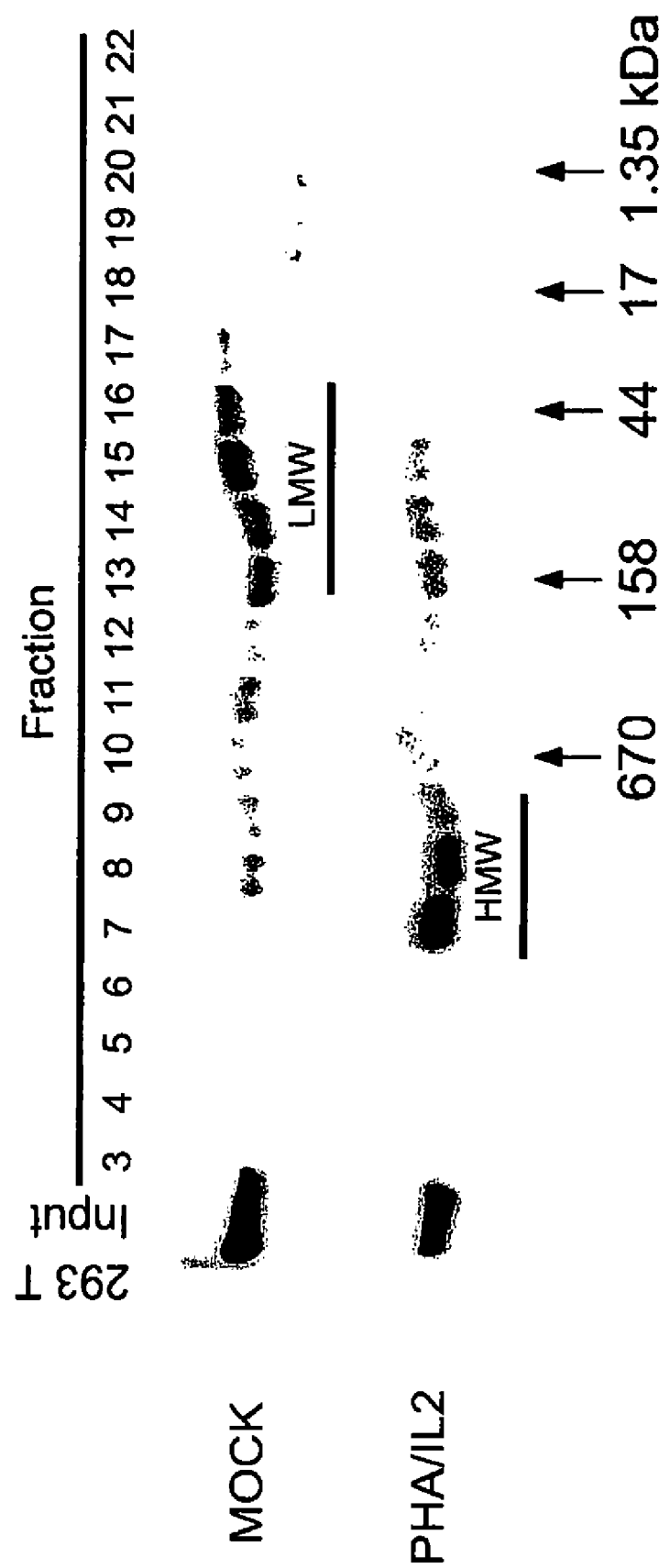
FIG. 18 depicts results showing that PHA/IL-2 stimulation of $CD4^+$ PBL promotes assembly of HMW APOBEC3G complexes.

FIG. 18 depicts results showing that PHA/IL-2 stimulation of CD4+ PBL promotes assembly of HMW APOBEC3G complexes.

Figure 19:
FIG. 19 depicts results showing that APOBEC3G in monocytes is present in a LMW complex.

FIG. 19 depicts results showing that APOBEC3G in monocytes is present in a LMW complex.

Figure 20:
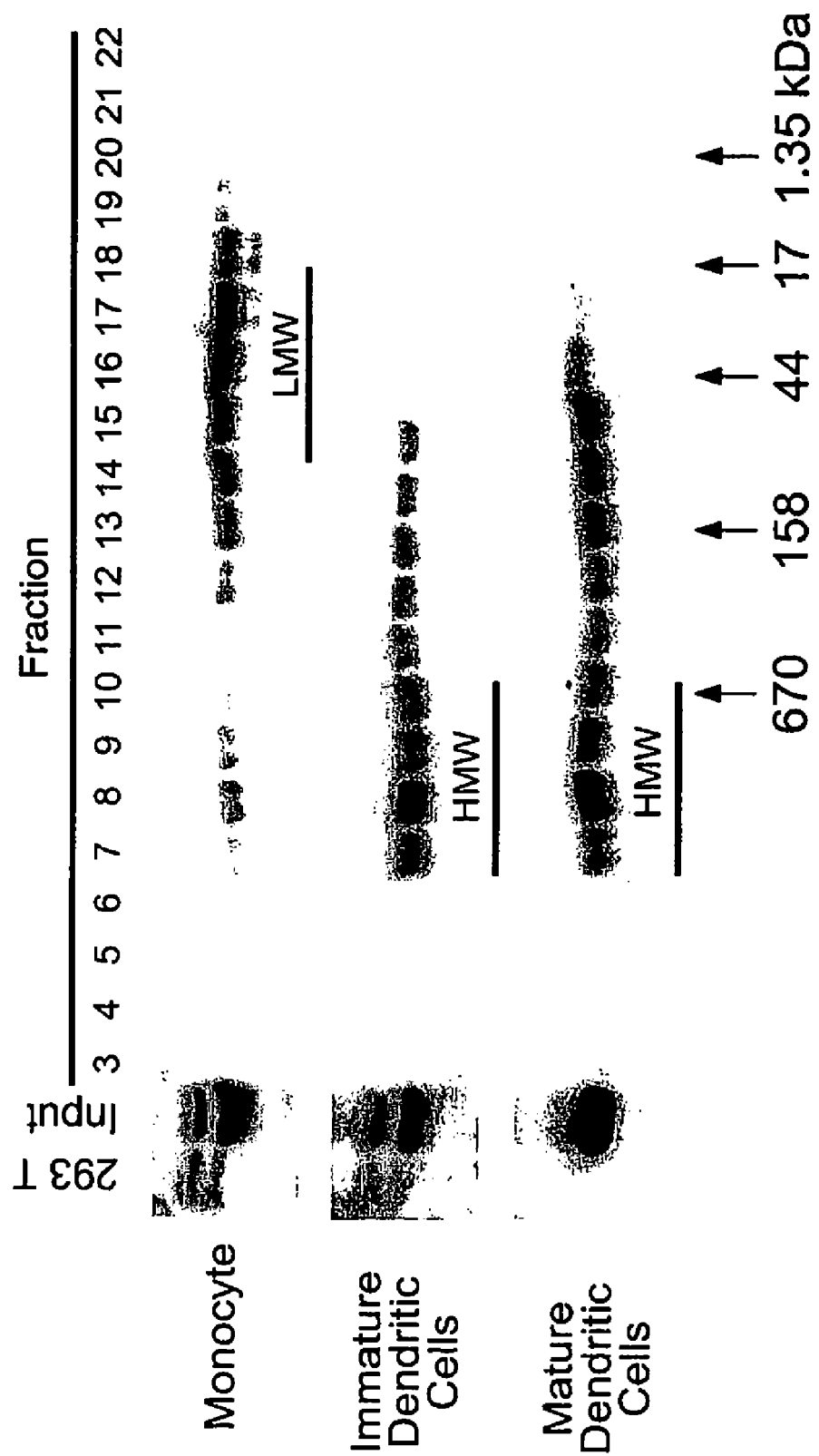
FIG. 20 depicts results showing that differentiation of monocytes promotes assembly of HMW APOBEC3G complexes.

FIG. 20 depicts results showing that differentiation of monocytes promotes assembly of HMW APOBEC3G complexes.

In summary, it was shown that:

1) APOBEC3G is recruited into a HMW ribonucleoprotein complex which lacks cytidine deaminase activity;

2) Treatment of the HMW APOBEC3G complex with RNase produces a LMW complex that exhibits a high level of cytidine deaminase activity.

3) Resting peripheral blood T cells and monocytes display LMW APOBEC3G complexes. Activation and/or differentiation of resting peripheral blood T cells and monocytes promotes the formation of HMW APOBEC3G complexes.

Example 3

The Effect of an N-Terminal Fragment of APOBEC3G on Vif-Induced Degradation of APOBEC3G HEK 293 cells were co-transfected with an HA-APOBEC3G expression vector or with increasing amounts (2 µg or 4 µg) of an HA-(1-104)APOBEC3G expression vector; and either an HIV-1 Vif or a control expression vector. The HA-APOBEC3G expression vector encodes wild-type (e.g., full-length) APOBEC3G fused in-frame to the hemagglutinin-epitope tag at the N-terminus. The HA-(1-104)APOBEC3G expression vector encodes amino acids 1-104 of APOBEC3G fused in-frame to the hemagglutinin-epitope tag. Cell lysates were clarified by centrifugation, and equal amounts of protein separated by SDS-PAGE. The separated proteins were transferred to nitrocellulose membranes, and both HA-APOBEC3G and HA-(1-104)APOBEC3G on the membranes were detected by anti-HA antibody. In cells transfected with the HA-APOBEC3G expression vector (and not co-transfected with the Vif expression vector), HA-APOBEC3G was produced that migrated at about 50 kD. In cells co-transfected with the Vif expression vector and the HA-APOBEC3G expression vector (and not co-transfected with the HA-(1-104)APOBEC3G expression vector), most of the HA-APOBEC3G was degraded. However, in cells co-transfected with the Vif expression vector, the HA-APOBEC3G expression vector, and either 2 µg or 4 µg of the HA-(1-104)APOBEC3G expression vector, the steady-state production of the ~50 kD HA-APOBEC3G fusion protein was significantly restored, in the presence of the HA-(1-104)APOBEC3G protein, to the level found in the absence of Vif co-expression. The results indicate that over-expression of HA-(1-104)APOBEC3G inhibits HIV-1 Vif-mediated degradation of HA-APOBEC3G.

Example 4

Construction of a Vif/luc-APOBEC3G Cell Line

Several cell lines were constructed that could serve as the basis for a high-throughput assay for inhibitors of HIV-1 Vif action. The cell lines produce Vif and an APOBEC3G fusion protein composed of APOBEC3G fused to a heterologous protein that provides a detectable signal. One such cell line was constructed as follows. HeLa cells were co-transfected with both a Vif expression vector and a vector expressing APOBEC3G tagged with *renilla*-luciferase (luc-APOBEC3G), to generate a Vif/luc-APOBEC3G cell line. The Vif expression vector contains a selectable marker that provides for resistance to histidinol. The luc-APOBEC3G expression vector contains a selectable marker that protects transfected cells from neomycin or G418.

The Vif/luc-APOBEC3G cell line was treated with the proteasome inhibitor MG132, an agent capable of blocking Vif-mediated degradation of APOBEC3G, and the cells were subsequently lysed. The cell lysates were clarified, and subjected to a conventional luciferase assay. The level of luc-APOBEC3G was expressed as relative light units (RLU). The RLU emitted from the cell lysate sample of the Vif/luc-APOBEC3G cells treated with MG132 was 203333. However, in the absence of the proteasome inhibitor, the RLU from lysates of the Vif/luc-APOBEC3G cells was 10180, representing about a 20-fold reduction. From these results, it was concluded that the Vif present in the cell line caused an approximately 20-fold reduction in the level of the luc-APOBEC3G protein, and that this activity of Vif was reversed by MG132.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An in vitro method for identifying an agent that inhibits a Vif activity in a cell, the method comprising the steps of:
   (a) contacting a cell that produces a Vif protein and an APOBEC3G protein with a test agent; and
   (b) determining the effect, if any, of the test agent on a Vif activity selected from the group consisting of association of a Vif protein with a high molecular weight complex comprising the APOBEC3G protein and cellular RNA, interference of a Vif protein with translation of APOBEC3G mRNA, and interference of a Vif protein with the intracellular localization of the APOBEC3G protein;
   wherein a higher level of the APOBEC3G protein in the cell contacted with the test agent compared to the level of APOBEC3G protein in a cell not treated with the test agent indicates that the test agent inhibits the Vif activity in the cell.

2. The method of claim 1, further comprising the step of:
   (c) lysing the cell.

3. The method of claim 1, wherein the step of determining the effect, if any, of the test agent on a Vif activity comprises determining an association of the Vif protein with a high molecular weight complex comprising the APOBEC3G protein and cellular RNA.

4. The method of claim 3, wherein determining an association of the Vif protein with the high molecular weight complex comprises detecting co-fractionation of the Vif protein with the high molecular weight complex.

5. The method according to claim 4, wherein co-fractionation comprises analyzing a cell lysate by size-exclusion fast performance liquid chromatography.

6. The method of claim 1, wherein the step of determining the effect, if any, of the test agent on a Vif activity comprises determining the level of newly translated APOBEC3G protein from the APOBEC3G mRNA.

7. The method of claim 6, wherein determining the level of newly translated APOBEC3G protein from the APOBEC3G mRNA comprises pulse-chase labeling.

8. The method of claim 1, wherein the step of determining the effect, if any, of the test agent on a Vif activity comprises determining the intracellular localization of APOBEC3G protein.

9. The method of claim 8, wherein determining the intracellular localization of APOBEC3G protein comprises detecting APOBEC3G protein in the nucleus of the cell or in the cytoplasm of the cell.

10. The method of claim 1, wherein the step of determining the effect, if any, of the test agent on a Vif activity comprises detecting an APOBEC3G protein comprising a label that provides a detectable signal.

11. The method of claim 10, wherein the label is selected from group consisting of a radioisotope, a fluorescer, a chemiluminescer, an epitope tag, an enzyme, a fusion partner, and a binding partner.

12. The method of claim 10, wherein the label is a radioisotope.

13. The method of claim 10, wherein the label is selected from the group consisting of β-galactosidase, luciferase, horse radish peroxidase, glutathione-S-transferase, hemagglutinin (HA), FLAG, c-myc, $(His)_n$, a fluorescent protein from an *Anthozoa* species, a green fluorescent protein (GFP) from *Renilla reniformis*, a GFP from *Renilla mulleri*, a GFP from *Ptilosarcus guernyi*, a GFP from *Aequonia victoria*, and a humanized GFP.

14. The method of claim 1, wherein the step of determining the effect, if any, of the test agent on a Vif activity comprises an immunological assay.

15. The method of claim 14, wherein the immunological assay comprises detecting APOBEC3G protein using an anti-APOBEC3G antibody.

16. The method of claim 15, wherein the anti-APOBEC3G antibody binds to the amino acid sequence of SEQ ID NO:8.

17. The method of claim 14, wherein the immunological assay comprises detecting a detectable fusion partner in the cell that produces an APOBEC3G fusion protein comprising the APOBEC3G protein and the fusion partner.

18. The method of claim 17, wherein the fusion partner is selected from the group consisting of HA, FLAG, c-myc, and $(His)_n$.

19. The method of claim 1, wherein the step of determining the effect, if any, of the test agent on a Vif activity comprises a fluorimetric assay.

20. The method of claim 19, wherein the fluorimetric assay comprises detecting a detectable fusion partner in the cell that produces an APOBEC3G fusion protein comprising the APOBEC3G protein and the fusion partner.

21. The method of claim 20, wherein the fusion partner is a green fluorescent protein (GFP).

22. The method of claim 21, wherein the green fluorescent protein is selected from the group consisting of GFPs from *Renilla reniformis*, *Renilla mulleri*, *Ptilosarcus guernyi*, *Aequonia victoria*, a humanized green fluorescent protein and fluorescent mutants thereof.

23. The method of claim 1, wherein the step of determining the effect, if any, of the test agent on a Vif activity comprises an enzymatic assay.

24. The method of claim 23, wherein the enzymatic assay comprises detecting a detectable fusion partner in the cell that produces an APOBEC3G fusion protein comprising the APOBEC3G protein and the fusion partner.

25. The method of claim 24, wherein the fusion partner is selected from the group consisting of β-galactosidase, luciferase, and horse radish peroxidase.

26. The method of claim 10, wherein the label is detected in the intact cell by flow cytometry.

27. The method of claim 1, wherein the APOBEC3G protein is an endogenous APOBEC3G protein produced in the cell.

28. The method of claim 1, wherein the cell is a cell culture.

29. The method of claim 1, wherein the cell is a eukaryotic cell.

30. The method of claim 29, wherein the cell is a mammalian cell.

31. The method of claim 29, wherein the cell is an immortalized cell.

32. The method of claim 30, wherein the cell is a non-permissive cell to infection with a human immunodeficiency virus.

33. The method of claim 32, wherein the cell is a H9 cell.

34. The method of claim 30, wherein the cell is a permissive cell to infection with a human immunodeficiency virus.

35. The method of claim 34, wherein the cell is selected from a Supt1 cell and a Jurkat cell.

36. The method of claim 1, wherein the cell is genetically modified with a nucleic acid comprising a nucleotide sequence encoding a Vif protein, wherein the Vif protein is produced in the cell.

37. The method of claim 36, wherein Vif is expressed from a vector.

38. The method of claim 37, wherein the Vif protein is expressed from a lentiviral vector.

39. The method of claim 36, wherein the cell is genetically modified with a nucleic acid comprising a nucleotide sequence encoding a Vif protein and a fusion partner, wherein a Vif fusion protein is produced in the cell.

40. The method of claim 39, wherein the Vif fusion protein comprises Vif and glutathione-S-transferase.

41. The method of claim 36, wherein the cell is transiently transfected with the nucleic acid.

42. The method of claim 36, wherein the cell is stably transfected with the nucleic acid.

43. The method of claim 1, wherein the cell is genetically modified with a nucleic acid comprising a nucleotide sequence encoding an APOBEC3G protein, wherein the APOBEC3G protein is produced in the cell.

44. The method of claim 43, wherein APOBEC3G protein is expressed from a vector.

45. The method of claim 44, wherein the APOBEC3G protein is expressed from a lentiviral vector.

46. The method of claim 43, wherein the cell is genetically modified with a nucleic acid comprising a nucleotide sequence encoding an APOBEC3G protein and a fusion partner, wherein an APOBEC3G fusion protein is produced in the cell.

47. The method of claim 43, wherein the cell is transiently transfected with the nucleic acid.

48. The method of claim 43, wherein the cell is stably transfected with the nucleic acid.

49. The method of claim 1, wherein the eukaryotic cell is genetically modified with one or more nucleic acids comprising a nucleotide sequence encoding an APOBEC3G protein and a nucleotide sequence encoding a Vif protein, wherein the APOBEC3G protein and the Vif protein are produced in the cell.

50. The method of claim 49, wherein the APOBEC3G protein and the Vif protein are expressed from a vector.

51. The method of claim 50, wherein the APOBEC3G protein and the Vif protein are expressed from a lentiviral vector.

52. The method of claim 49, wherein the cell is genetically modified with
   (i) a nucleic acid comprising a nucleotide sequence encoding an APOBEC3G protein and a first fusion partner; wherein an APOBEC3G fusion protein is produced in the cell, and
   (ii) a nucleic acid comprising a nucleotide sequence encoding a Vif protein and a second fusion partner; wherein a Vif fusion protein is produced in the cell.

53. The method of claim 49, wherein the cell is transiently transfected with the nucleic acid.

54. The method of claim 49, wherein the cell is stably transfected with the nucleic acid.

55. The method of claim 1, wherein the cell is infected with a lentivirus.

56. The method of claim 55, wherein the lentivirus is selected from the group consisting of human immunodeficiency virus-1 (HIV-1), human immunodeficiency virus-2 (HIV-2), simian immunodeficiency virus and feline immunodeficiency virus.

57. The method of claim 55, wherein the lentivirus is HIV-1 or HIV-2.

58. The method of claim 1, wherein the step of determining the level of APOBEC3G protein in the cell comprises using a high throughput technique.

59. The method of claim 1, wherein the test agent comprises a synthetic, semi-synthetic, or naturally-occurring inorganic or organic molecule.

60. The method of claim 59, wherein the test agent has a molecular weight of more than 50 and less than about 2,500 Daltons.

61. The method of claim 59, wherein the test agent comprises a functional group for structural interaction with a protein.

62. The method of claim 1, wherein the test agent is a biomolecule selected from the group consisting of a peptide, a peptidomimetic, a peptide aptamer, a saccharide, a fatty acid, a steroid, a purine, a pyrimidine, a derivative, a structural analog and a combination thereof.

63. The method of claim 62, wherein the test agent comprises a peptide or peptidomimetic.

64. The method of claim 63, wherein the peptide is conjugated to a decapeptide comprised of arginine residues.

65. The method of claim 1, further comprising the step of:
   (c) contacting the cell with a nucleoside reverse transcriptase inhibitor, a non-nucleoside reverse transcriptase inhibitor, or a protease inhibitor.

* * * * *

SEQUENCE LISTING

<160> NUMBER OF SEQ ID NOS: 8

<210> SEQ ID NO 1
<211> LENGTH: 10
<212> TYPE: PRT
<213> ORGANISM: Artificial Sequence
<220> FEATURE:
<223> OTHER INFORMATION: synthetic protein created in a laboratory

<400> SEQUENCE: 1

Cys Tyr Pro Tyr Asp Val Pro Asp Tyr Ala
 1               5                  10

<210> SEQ ID NO 2
<211> LENGTH: 8
<212> TYPE: PRT
<213> ORGANISM: Artificial Sequence
<220> FEATURE:
<223> OTHER INFORMATION: synthetic protein created in a laboratory

<400> SEQUENCE: 2

Asp Tyr Lys Asp Asp Asp Asp Lys
 1               5

<210> SEQ ID NO 3
<211> LENGTH: 11
<212> TYPE: PRT
<213> ORGANISM: Artificial Sequence
<220> FEATURE:
<223> OTHER INFORMATION: synthetic protein created in a laboratory

<400> SEQUENCE: 3

Cys Glu Gln Lys Leu Ile Ser Glu Glu Asp Leu
 1               5                  10

<210> SEQ ID NO 4
<211> LENGTH: 384
<212> TYPE: PRT
<213> ORGANISM: Homo sapiens

<400> SEQUENCE: 4

Met Lys Pro His Phe Arg Asn Thr Val Glu Arg Met Tyr Arg Asp Thr
 1               5                  10                  15

Phe Ser Tyr Asn Phe Tyr Asn Arg Pro Ile Leu Ser Arg Arg Asn Thr
                20                  25                  30

Val Trp Leu Cys Tyr Glu Val Lys Thr Lys Gly Pro Ser Arg Pro Pro
            35                  40                  45

Leu Asp Ala Lys Ile Phe Arg Gly Gln Val Tyr Ser Glu Leu Lys Tyr
        50                  55                  60

His Pro Glu Met Arg Phe Phe His Trp Phe Ser Lys Trp Arg Lys Leu
65                  70                  75                  80

His Arg Asp Gln Glu Tyr Glu Val Thr Trp Tyr Ile Ser Trp Ser Pro
                85                  90                  95

Cys Thr Lys Cys Thr Arg Asp Met Ala Thr Phe Leu Ala Glu Asp Pro
            100                 105                 110

Lys Val Thr Leu Thr Ile Phe Val Ala Arg Leu Tyr Tyr Phe Trp Asp
        115                 120                 125

Pro Asp Tyr Gln Glu Ala Leu Arg Ser Leu Cys Gln Lys Arg Asp Gly
    130                 135                 140

Pro Arg Ala Thr Met Lys Ile Met Asn Tyr Asp Glu Phe Gln His Cys

```
                145                 150                 155                 160
Trp Ser Lys Phe Val Tyr Ser Gln Arg Glu Leu Phe Glu Pro Trp Asn
                165                 170                 175

Asn Leu Pro Lys Tyr Tyr Ile Leu Leu His Ile Met Leu Gly Glu Ile
                180                 185                 190

Leu Arg His Ser Met Asp Pro Pro Thr Phe Thr Phe Asn Phe Asn Asn
                195                 200                 205

Glu Pro Trp Val Arg Gly Arg His Glu Thr Tyr Leu Cys Tyr Glu Val
                210                 215                 220

Glu Arg Met His Asn Asp Thr Trp Val Leu Leu Asn Gln Arg Arg Gly
225                 230                 235                 240

Phe Leu Cys Asn Gln Ala Pro His Lys His Gly Phe Leu Glu Gly Arg
                245                 250                 255

His Ala Glu Leu Cys Phe Leu Asp Val Ile Pro Phe Trp Lys Leu Asp
                260                 265                 270

Leu Asp Gln Asp Tyr Arg Val Thr Cys Phe Thr Ser Trp Ser Pro Cys
                275                 280                 285

Phe Ser Cys Ala Gln Glu Met Ala Lys Phe Ile Ser Lys Asn Lys His
                290                 295                 300

Val Ser Leu Cys Ile Phe Thr Ala Arg Ile Tyr Asp Asp Gln Gly Arg
305                 310                 315                 320

Cys Gln Glu Gly Leu Arg Thr Leu Ala Glu Ala Gly Ala Lys Ile Ser
                325                 330                 335

Ile Met Thr Tyr Ser Glu Phe Lys His Cys Trp Asp Thr Phe Val Asp
                340                 345                 350

His Gln Gly Cys Pro Phe Gln Pro Trp Asp Gly Leu Asp Glu His Ser
                355                 360                 365

Gln Asp Leu Ser Gly Arg Leu Arg Ala Ile Leu Gln Asn Gln Glu Asn
                370                 375                 380

<210> SEQ ID NO 5
<211> LENGTH: 40
<212> TYPE: PRT
<213> ORGANISM: Artificial Sequence
<220> FEATURE:
<223> OTHER INFORMATION: synthetic protein created in a laboratory

<400> SEQUENCE: 5

Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
                20                  25                  30

Val Trp Leu Cys Tyr Glu Val Lys
            35                  40

<210> SEQ ID NO 6
<211> LENGTH: 29
<212> TYPE: PRT
<213> ORGANISM: Artificial Sequence
<220> FEATURE:
<223> OTHER INFORMATION: synthetic protein created in a laboratory

<400> SEQUENCE: 6

Cys Pro Phe Gln Pro Trp Asp Gly Leu Asp Glu His Ser Gln Asp Leu
1               5                   10                  15

Ser Gly Arg Leu Arg Ala Ile Leu Gln Asn Gln Glu Asn
            20                  25
```

```
<210> SEQ ID NO 7
<211> LENGTH: 104
<212> TYPE: PRT
<213> ORGANISM: Artificial Sequence
<220> FEATURE:
<223> OTHER INFORMATION: synthetic protein created in a laboratory

<400> SEQUENCE: 7

Met Lys Pro His Phe Arg Asn Thr Val Glu Arg Met Tyr Arg Asp Thr
 1               5                  10                  15

Phe Ser Tyr Asn Phe Tyr Asn Arg Pro Ile Leu Ser Arg Arg Asn Thr
             20                  25                  30

Val Trp Leu Cys Tyr Glu Val Lys Thr Lys Gly Pro Ser Arg Pro Pro
         35                  40                  45

Leu Asp Ala Lys Ile Phe Arg Gly Gln Val Tyr Ser Glu Leu Lys Tyr
     50                  55                  60

His Pro Glu Met Arg Phe Phe His Trp Phe Ser Lys Trp Arg Lys Leu
 65                  70                  75                  80

His Arg Asp Gln Glu Tyr Glu Val Thr Trp Tyr Ile Ser Trp Ser Pro
                 85                  90                  95

Cys Thr Lys Cys Thr Arg Asp Met
            100

<210> SEQ ID NO 8
<211> LENGTH: 16
<212> TYPE: PRT
<213> ORGANISM: Artificial Sequence
<220> FEATURE:
<223> OTHER INFORMATION: synthetic protein created in a laboratory

<400> SEQUENCE: 8

Gln Asp Leu Ser Gly Arg Leu Arg Ala Ile Leu Gln Asn Gln Glu Asn
 1               5                  10                  15
```